United States Patent
Park et al.

(10) Patent No.: US 10,988,779 B2
(45) Date of Patent: Apr. 27, 2021

(54) VIRAL DELIVERY OF RNA UTILIZING SELF-CLEAVING RIBOZYMES AND CRISPR-BASED APPLICATIONS THEREOF

(71) Applicant: Icahn School of Medicine at Mount Sinai, New York, NY (US)

(72) Inventors: Arnold Park, New York, NY (US); Benhur Lee, New York, NY (US); Ruth Watkinson, New York, NY (US)

(73) Assignee: Icahn School of Medicine at Mount Sinai, New York, NY (US)

(*) Notice: Subject to any disclaimer, the term of this patent is extended or adjusted under 35 U.S.C. 154(b) by 0 days.

(21) Appl. No.: 16/311,887

(22) PCT Filed: Jun. 22, 2017

(86) PCT No.: PCT/US2017/038780
§ 371 (c)(1),
(2) Date: Dec. 20, 2018

(87) PCT Pub. No.: WO2017/223330
PCT Pub. Date: Dec. 28, 2017

(65) Prior Publication Data
US 2020/0140887 A1    May 7, 2020

Related U.S. Application Data

(60) Provisional application No. 62/353,452, filed on Jun. 22, 2016.

(51) Int. Cl.
| | | |
|---|---|---|
| A61K 39/155 | (2006.01) |
| C07K 14/005 | (2006.01) |
| C12N 15/86 | (2006.01) |
| C12N 15/11 | (2006.01) |
| C12N 7/00 | (2006.01) |
| C12N 9/22 | (2006.01) |
| C12N 15/113 | (2010.01) |

(52) U.S. Cl.
CPC .............. *C12N 15/86* (2013.01); *C12N 7/00* (2013.01); *C12N 9/22* (2013.01); *C12N 15/113* (2013.01); *C12N 2310/121* (2013.01); *C12N 2310/20* (2017.05); *C12N 2760/10121* (2013.01); *C12N 2760/18843* (2013.01); *C12N 2800/80* (2013.01)

(58) Field of Classification Search
CPC .......... C07K 14/005; A61K 2039/5256; A61K 2039/5254; C12N 15/86; C12N 7/00
See application file for complete search history.

(56) References Cited

U.S. PATENT DOCUMENTS

2008/0031855 A1* 2/2008 Okano ............... A61K 35/76 424/93.6
2013/0245094 A1 9/2013 Lee et al.

FOREIGN PATENT DOCUMENTS

| WO | 2012/170431 A2 | 12/2012 |
| WO | 2015/195621 A1 | 12/2015 |
| WO | WO2015195621 | * 12/2015 |

OTHER PUBLICATIONS

Park et al., "Sendai virus, an RNA virus with no risk of genomic integration, delivers CRISPR/Cas9 for efficient gene editing", Molecular Therapy—Methods & Clinical Dev, vol. 3, Aug. 2016, p. 16057.
Extended European Search Report dated Mar. 26, 2020 issued in the corresponding European Patent Application No. 17816216.0.

* cited by examiner

*Primary Examiner* — Barry A Chestnut
(74) *Attorney, Agent, or Firm* — Fox Rothschild LLP

(57) ABSTRACT

The present disclosure relates to viral delivery of RNA utilizing self-cleaving ribozymes and applications of such, including but not limited to CRISPR-Cas related applications.

10 Claims, 28 Drawing Sheets
Specification includes a Sequence Listing.

A

SEQUENCE LISTING

<160> NUMBER OF SEQ ID NOS: 75

<210> SEQ ID NO 1
<211> LENGTH: 442
<212> TYPE: DNA
<213> ORGANISM: Artificial
<220> FEATURE:
<223> OTHER INFORMATION: synthetic

<400> SEQUENCE: 1

```
atcccgggtg aggcatccca ccatcctcag tcacagagag acccaatcta ccatcagcat      60
cagccagtaa agattaagaa aaacttaggg tgaaagaaat ttcacctaac acggcgcagc     120
gatcgcgtgg ccctgatgag tccgtgagga cgaaacggta ggaattccta ccgtcggcca     180
cgagttcgag atcgagtttt agagctagaa atagcaagtt aaaataaggc tagtccgtta     240
tcaacttgaa aaagtggcac cgagtcggtg cacgtatcac cggagtcgac tccggtctga     300
tgagtccgtg aggacgaaat acgtatcccg ggtgaggcat cccaccatcc tcagtcacag     360
agagacccaa tctaccatca gcatcagcca gtaaagatta agaaaaactt agggtgaaag     420
aaatttcacc taacacggcg ca                                              442
```

```
<210> SEQ ID NO 2
<211> LENGTH: 39
<212> TYPE: RNA
<213> ORGANISM: Artificial
<220> FEATURE:
<223> OTHER INFORMATION: synthetic

<400> SEQUENCE: 2
guggcccuga ugagcgaaac gguaggaauu ccuaccguc                         39

<210> SEQ ID NO 3
<211> LENGTH: 47
<212> TYPE: RNA
<213> ORGANISM: Artificial
<220> FEATURE:
<223> OTHER INFORMATION: synthetic

<400> SEQUENCE: 3
caccggaguc gacuccgguc ugaugaguccc gugaggacga aauacgu               47
```

<210> SEQ ID NO 4
<211> LENGTH: 19
<212> TYPE: PRT
<213> ORGANISM: Artificial
<220> FEATURE:
<223> OTHER INFORMATION: synthetic

<400> SEQUENCE: 4

Ala Thr Asn Phe Ser Leu Leu Lys Gln Ala Gly Asp Val Glu Glu Asn
1               5                   10                  15

Pro Gly Pro

```
<210> SEQ ID NO 5
<211> LENGTH: 23
<212> TYPE: DNA
<213> ORGANISM: Artificial
<220> FEATURE:
<223> OTHER INFORMATION: synthetic

<400> SEQUENCE: 5
ggccacgagt tcgagatcga ggg                                          23

<210> SEQ ID NO 6
<211> LENGTH: 23
<212> TYPE: DNA
<213> ORGANISM: Artificial
<220> FEATURE:
<223> OTHER INFORMATION: synthetic

<400> SEQUENCE: 6
caggttggac caagctatgc agg                                          23

<210> SEQ ID NO 7
<211> LENGTH: 23
<212> TYPE: DNA
<213> ORGANISM: Artificial
<220> FEATURE:
<223> OTHER INFORMATION: synthetic

<400> SEQUENCE: 7
cagactggat caagctatgc cag                                          23

<210> SEQ ID NO 8
<211> LENGTH: 23
<212> TYPE: DNA
```

```
<213> ORGANISM: Artificial
<220> FEATURE:
<223> OTHER INFORMATION: synthetic

<400> SEQUENCE: 8
caagttacaa caagctatgc aag                                           23

<210> SEQ ID NO 9
<211> LENGTH: 23
<212> TYPE: DNA
<213> ORGANISM: Artificial
<220> FEATURE:
<223> OTHER INFORMATION: synthetic

<400> SEQUENCE: 9 aaggttttc caagctatgc tag                                            23

<210> SEQ ID NO 10
<211> LENGTH: 23
<212> TYPE: DNA
<213> ORGANISM: Artificial
<220> FEATURE:
<223> OTHER INFORMATION: synthetic

<400> SEQUENCE: 10
caggattcac caagctctgc cag                                           23

<210> SEQ ID NO 11
<211> LENGTH: 23
<212> TYPE: DNA
<213> ORGANISM: Artificial
<220> FEATURE:
<223> OTHER INFORMATION: synthetic

<400> SEQUENCE: 11
cagtttggtt caagctatgt tag                                           23

<210> SEQ ID NO 12
<211> LENGTH: 23
<212> TYPE: DNA
<213> ORGANISM: Artificial
<220> FEATURE:
<223> OTHER INFORMATION: synthetic

<400> SEQUENCE: 12
agaattcagc cctaacctct ggg                                           23

<210> SEQ ID NO 13
<211> LENGTH: 23
<212> TYPE: DNA
<213> ORGANISM: Artificial
<220> FEATURE:
<223> OTHER INFORMATION: synthetic

<400> SEQUENCE: 13
agaattcagg cttaacctct tag                                           23

<210> SEQ ID NO 14
<211> LENGTH: 23
<212> TYPE: DNA
<213> ORGANISM: Artificial
<220> FEATURE:
<223> OTHER INFORMATION: synthetic

<400> SEQUENCE: 14
aaaattcttc cctaacctct aag                                           23
```

<210> SEQ ID NO 15
<211> LENGTH: 23
<212> TYPE: DNA
<213> ORGANISM: Artificial
<220> FEATURE:
<223> OTHER INFORMATION: synthetic

<400> SEQUENCE: 15
acatttcagc tctaacctct ggg                                              23

<210> SEQ ID NO 16
<211> LENGTH: 23
<212> TYPE: DNA
<213> ORGANISM: Artificial
<220> FEATURE:
<223> OTHER INFORMATION: synthetic

<400> SEQUENCE: 16
ataaatcagc cctaacatct gag                                              23

<210> SEQ ID NO 17
<211> LENGTH: 23
<212> TYPE: DNA
<213> ORGANISM: Artificial
<220> FEATURE:
<223> OTHER INFORMATION: synthetic

<400> SEQUENCE: 17
aaaagtttgc cctaacctct cag                                              23

<210> SEQ ID NO 18
<211> LENGTH: 19
<212> TYPE: DNA
<213> ORGANISM: Artificial
<220> FEATURE:
<223> OTHER INFORMATION: synthetic

<400> SEQUENCE: 18
ggcgaggagg ataacatgg                                                   19

<210> SEQ ID NO 19
<211> LENGTH: 21
<212> TYPE: DNA
<213> ORGANISM: Artificial
<220> FEATURE:
<223> OTHER INFORMATION: synthetic

<400> SEQUENCE: 19
cttcagcctc tgcttgatct c                                                21

<210> SEQ ID NO 20
<211> LENGTH: 22
<212> TYPE: DNA
<213> ORGANISM: Artificial
<220> FEATURE:
<223> OTHER INFORMATION: synthetic

<400> SEQUENCE: 20
ttgtcatggt catctgctac tc                                               22

<210> SEQ ID NO 21
<211> LENGTH: 22
<212> TYPE: DNA
<213> ORGANISM: Artificial
<220> FEATURE:

-continued

<223> OTHER INFORMATION: synthetic

<400> SEQUENCE: 21
gtgtcacaag cccacagata tt                                          22

<210> SEQ ID NO 22
<211> LENGTH: 24
<212> TYPE: DNA
<213> ORGANISM: Artificial
<220> FEATURE:
<223> OTHER INFORMATION: synthetic

<400> SEQUENCE: 22
ctccactttc cataacagtc tagg                                        24

<210> SEQ ID NO 23
<211> LENGTH: 23
<212> TYPE: DNA
<213> ORGANISM: Artificial
<220> FEATURE:
<223> OTHER INFORMATION: synthetic

<400> SEQUENCE: 23
ggtccttgga acagtagaga tag                                         23

<210> SEQ ID NO 24
<211> LENGTH: 22
<212> TYPE: DNA
<213> ORGANISM: Artificial
<220> FEATURE:
<223> OTHER INFORMATION: synthetic

<400> SEQUENCE: 24
tgtttgctgt gaggctactt tg                                          22

<210> SEQ ID NO 25
<211> LENGTH: 22
<212> TYPE: DNA
<213> ORGANISM: Artificial
<220> FEATURE:
<223> OTHER INFORMATION: synthetic

<400> SEQUENCE: 25
tcactgtcca atctgcttta cc                                          22

<210> SEQ ID NO 26
<211> LENGTH: 25
<212> TYPE: DNA
<213> ORGANISM: Artificial
<220> FEATURE:
<223> OTHER INFORMATION: synthetic

<400> SEQUENCE: 26
gcagaggcat tataaaccca atatg                                       25

<210> SEQ ID NO 27
<211> LENGTH: 19
<212> TYPE: DNA
<213> ORGANISM: Artificial
<220> FEATURE:
<223> OTHER INFORMATION: synthetic

<400> SEQUENCE: 27
ccaggaggaa ctggcaaat                                              19

<210> SEQ ID NO 28
<211> LENGTH: 22
<212> TYPE: DNA
<213> ORGANISM: Artificial
<220> FEATURE:
<223> OTHER INFORMATION: synthetic

<400> SEQUENCE: 28
aagctccatc ttcttcgttc tt                                              22

<210> SEQ ID NO 29
<211> LENGTH: 25
<212> TYPE: DNA
<213> ORGANISM: Artificial
<220> FEATURE:
<223> OTHER INFORMATION: synthetic

<400> SEQUENCE: 29
agtaggagat ggatttacag gtatt                                           25

<210> SEQ ID NO 30
<211> LENGTH: 20
<212> TYPE: DNA
<213> ORGANISM: Artificial
<220> FEATURE:
<223> OTHER INFORMATION: synthetic

<400> SEQUENCE: 30
cagtgacatg agcacctgaa                                                 20

<210> SEQ ID NO 31
<211> LENGTH: 22
<212> TYPE: DNA
<213> ORGANISM: Artificial
<220> FEATURE:
<223> OTHER INFORMATION: synthetic

<400> SEQUENCE: 31
gcaaggacat cctcatccat aa                                              22

<210> SEQ ID NO 32
<211> LENGTH: 22
<212> TYPE: DNA
<213> ORGANISM: Artificial
<220> FEATURE:
<223> OTHER INFORMATION: synthetic

<400> SEQUENCE: 32
cctggacaag gactggtact at                                              22

<210> SEQ ID NO 33
<211> LENGTH: 20
<212> TYPE: DNA
<213> ORGANISM: Artificial
<220> FEATURE:
<223> OTHER INFORMATION: synthetic

<400> SEQUENCE: 33
tagcacaggg tcccaaattc                                                 20

<210> SEQ ID NO 34
<211> LENGTH: 22
<212> TYPE: DNA
<213> ORGANISM: Artificial
<220> FEATURE:
<223> OTHER INFORMATION: synthetic

<400> SEQUENCE: 34
gcaggctggt aattgatctt tc                                          22

<210> SEQ ID NO 35
<211> LENGTH: 22
<212> TYPE: DNA
<213> ORGANISM: Artificial
<220> FEATURE:
<223> OTHER INFORMATION: synthetic

<400> SEQUENCE: 35
tgatccacag ttggttgaat cc                                          22

<210> SEQ ID NO 36
<211> LENGTH: 22
<212> TYPE: DNA
<213> ORGANISM: Artificial
<220> FEATURE:
<223> OTHER INFORMATION: synthetic

<400> SEQUENCE: 36
ccagaatgtg tcctgggttt ag                                          22

<210> SEQ ID NO 37
<211> LENGTH: 20
<212> TYPE: DNA
<213> ORGANISM: Artificial
<220> FEATURE:
<223> OTHER INFORMATION: synthetic

<400> SEQUENCE: 37
gtgtcagagc gagactttgt                                             20

<210> SEQ ID NO 38
<211> LENGTH: 23
<212> TYPE: DNA
<213> ORGANISM: Artificial
<220> FEATURE:
<223> OTHER INFORMATION: synthetic

<400> SEQUENCE: 38
ggagtatctt cagctgtgag aag                                         23

<210> SEQ ID NO 39
<211> LENGTH: 22
<212> TYPE: DNA
<213> ORGANISM: Artificial
<220> FEATURE:
<223> OTHER INFORMATION: synthetic

<400> SEQUENCE: 39
ctgttacacg ttccttgcta ct                                          22

<210> SEQ ID NO 40
<211> LENGTH: 22
<212> TYPE: DNA
<213> ORGANISM: Artificial
<220> FEATURE:
<223> OTHER INFORMATION: synthetic

<400> SEQUENCE: 40
ctgattgagt gggtcatcag aa                                          22

<210> SEQ ID NO 41
<211> LENGTH: 19

<212> TYPE: DNA
<213> ORGANISM: Artificial
<220> FEATURE:
<223> OTHER INFORMATION: synthetic

<400> SEQUENCE: 41
gctacgtgct ggtgctaaa                                                        19

<210> SEQ ID NO 42
<211> LENGTH: 24
<212> TYPE: DNA
<213> ORGANISM: Artificial
<220> FEATURE:
<223> OTHER INFORMATION: synthetic

<400> SEQUENCE: 42
gtccaggaaa gaaagttgca taag                                                  24

<210> SEQ ID NO 43
<211> LENGTH: 21
<212> TYPE: DNA
<213> ORGANISM: Artificial
<220> FEATURE:
<223> OTHER INFORMATION: synthetic

<400> SEQUENCE: 43
gctgtctgct ggaaagatag t                                                     21

<210> SEQ ID NO 44
<211> LENGTH: 49
<212> TYPE: DNA
<213> ORGANISM: Artificial Sequence
<220> FEATURE:
<223> OTHER INFORMATION: Primer

<400> SEQUENCE: 44
aacggccacg agttcgagat cgagggcgag ggcgagggcc gcccctacg                       49

<210> SEQ ID NO 45
<211> LENGTH: 50
<212> TYPE: DNA
<213> ORGANISM: Artificial Sequence
<220> FEATURE:
<223> OTHER INFORMATION: primer

<400> SEQUENCE: 45
aacggccacg agttcgagat tcgagggcga gggcgagggc cgcccctacg                      50

<210> SEQ ID NO 46
<211> LENGTH: 43
<212> TYPE: DNA
<213> ORGANISM: Artificial Sequence
<220> FEATURE:
<223> OTHER INFORMATION: primer

<400> SEQUENCE: 46
aacggccacg agttcgaggg cgagggcgag ggccgcccct acg                             43

<210> SEQ ID NO 47
<211> LENGTH: 37
<212> TYPE: DNA
<213> ORGANISM: Artificial Sequence
<220> FEATURE:
<223> OTHER INFORMATION: primer

<400> SEQUENCE: 47
aacggccacg agggcgaggg cgagggccgc ccctacg          37

<210> SEQ ID NO 48
<211> LENGTH: 37
<212> TYPE: DNA
<213> ORGANISM: Artificial Sequence
<220> FEATURE:
<223> OTHER INFORMATION: primer

<400> SEQUENCE: 48
aacggccacg agttcgaggg cgagggccgc ccctacg          37

<210> SEQ ID NO 49
<211> LENGTH: 10
<212> TYPE: DNA
<213> ORGANISM: Artificial Sequence
<220> FEATURE:
<223> OTHER INFORMATION: primer

<400> SEQUENCE: 49
aacggccacg                                        10

<210> SEQ ID NO 50
<211> LENGTH: 29
<212> TYPE: DNA
<213> ORGANISM: Artificial Sequence
<220> FEATURE:
<223> OTHER INFORMATION: primer

<400> SEQUENCE: 50
taacaggttg gaccaagcta tgcaggtga                   29

<210> SEQ ID NO 51
<211> LENGTH: 24
<212> TYPE: DNA
<213> ORGANISM: Artificial Sequence
<220> FEATURE:
<223> OTHER INFORMATION: primer

<400> SEQUENCE: 51
taacaggttg gaccaagcag gtga                        24

<210> SEQ ID NO 52
<211> LENGTH: 27
<212> TYPE: DNA
<213> ORGANISM: Artificial Sequence
<220> FEATURE:
<223> OTHER INFORMATION: primer

<400> SEQUENCE: 52
taacaggttg gaccaagctg caggtga                     27

<210> SEQ ID NO 53
<211> LENGTH: 28
<212> TYPE: DNA
<213> ORGANISM: Artificial Sequence
<220> FEATURE:
<223> OTHER INFORMATION: primer

<400> SEQUENCE: 53
taacaggttg gaccaagctt gcaggtga                    28

<210> SEQ ID NO 54
<211> LENGTH: 30
<212> TYPE: DNA
<213> ORGANISM: Artificial Sequence

```
<220> FEATURE:
<223> OTHER INFORMATION: primer

<400> SEQUENCE: 54
taacaggttg gaccaagcta ttgcaggtga                                    30

<210> SEQ ID NO 55
<211> LENGTH: 27
<212> TYPE: DNA
<213> ORGANISM: Artificial Sequence
<220> FEATURE:
<223> OTHER INFORMATION: primer

<400> SEQUENCE: 55
taacaggttg gaccaagcta caggtga                                       27

<210> SEQ ID NO 56
<211> LENGTH: 29
<212> TYPE: DNA
<213> ORGANISM: Artificial Sequence
<220> FEATURE:
<223> OTHER INFORMATION: primer

<400> SEQUENCE: 56
tcaagaattc agccctaacc tctggggtc                                     29

<210> SEQ ID NO 57
<211> LENGTH: 28
<212> TYPE: DNA
<213> ORGANISM: Artificial Sequence
<220> FEATURE:
<223> OTHER INFORMATION: primer

<400> SEQUENCE: 57
tcaagaattc agccctaact ctggggtc                                      28

<210> SEQ ID NO 58
<211> LENGTH: 27
<212> TYPE: DNA
<213> ORGANISM: Artificial Sequence
<220> FEATURE:
<223> OTHER INFORMATION: primer

<400> SEQUENCE: 58
tcaagaattc agccctaacc tggggtc                                       27

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
tcaagaattc agccctaacc ctctggggtc                                    30

<210> SEQ ID NO 60
<211> LENGTH: 27
<212> TYPE: DNA
<213> ORGANISM: Artificial Sequence
<220> FEATURE:
<223> OTHER INFORMATION: primer

<400> SEQUENCE: 60
tcaagaattc agccctaatc tggggtc                                       27
```

<210> SEQ ID NO 61
<211> LENGTH: 30
<212> TYPE: DNA
<213> ORGANISM: Artificial Sequence
<220> FEATURE:
<223> OTHER INFORMATION: primer

<400> SEQUENCE: 61
tcaagaattc agccctaacc ttctggggtc                                        30

<210> SEQ ID NO 62
<211> LENGTH: 29
<212> TYPE: DNA
<213> ORGANISM: Artificial Sequence
<220> FEATURE:
<223> OTHER INFORMATION: primer

<400> SEQUENCE: 62
taacaggttg gaccaagcta tgcaggtga                                         29

<210> SEQ ID NO 63
<211> LENGTH: 28
<212> TYPE: DNA
<213> ORGANISM: Artificial Sequence
<220> FEATURE:
<223> OTHER INFORMATION: primer

<400> SEQUENCE: 63
taacaggttg gaccaagctt gcaggtga                                          28

<210> SEQ ID NO 64
<211> LENGTH: 28
<212> TYPE: DNA
<213> ORGANISM: Artificial Sequence
<220> FEATURE:
<223> OTHER INFORMATION: primer

<400> SEQUENCE: 64
taacaggttg gaccaagcta gcaggtga                                          28

<210> SEQ ID NO 65
<211> LENGTH: 27
<212> TYPE: DNA
<213> ORGANISM: Artificial Sequence
<220> FEATURE:
<223> OTHER INFORMATION: primer

<400> SEQUENCE: 65
taacaggttg gaccaagctg caggtga                                           27

<210> SEQ ID NO 66
<211> LENGTH: 25
<212> TYPE: DNA
<213> ORGANISM: Artificial Sequence
<220> FEATURE:
<223> OTHER INFORMATION: primer

<400> SEQUENCE: 66
taacaggttg gaccaatgca ggtga                                             25

<210> SEQ ID NO 67
<211> LENGTH: 30
<212> TYPE: DNA
<213> ORGANISM: Artificial Sequence
<220> FEATURE:
<223> OTHER INFORMATION: primer

<400> SEQUENCE: 67
taacaggttg gaccaagcta ttgcaggtga                                30

<210> SEQ ID NO 68
<211> LENGTH: 55
<212> TYPE: DNA
<213> ORGANISM: Artificial Sequence
<220> FEATURE:
<223> OTHER INFORMATION: primer

<400> SEQUENCE: 68
aataattgca gtagctctaa caggttggac caagctatgc aggtgacaga gactc       55

<210> SEQ ID NO 69
<211> LENGTH: 56
<212> TYPE: DNA
<213> ORGANISM: Artificial Sequence
<220> FEATURE:
<223> OTHER INFORMATION: primer

<400> SEQUENCE: 69
aataattgca gtagctctaa caggttggac caagctattg caggtgacag agactc      56

<210> SEQ ID NO 70
<211> LENGTH: 56
<212> TYPE: DNA
<213> ORGANISM: Artificial Sequence
<220> FEATURE:
<223> OTHER INFORMATION: primer

<400> SEQUENCE: 70
aataattgca gtagctctaa caggttggac caagctattg caggtgacaa aaactc      56

<210> SEQ ID NO 71
<211> LENGTH: 34
<212> TYPE: DNA
<213> ORGANISM: Artificial Sequence
<220> FEATURE:
<223> OTHER INFORMATION: primer

<400> SEQUENCE: 71
aataattgca gtagctctaa caggttggac caag                              34

<210> SEQ ID NO 72
<211> LENGTH: 34
<212> TYPE: DNA
<213> ORGANISM: Artificial Sequence
<220> FEATURE:
<223> OTHER INFORMATION: primer
<220> FEATURE:
<221> NAME/KEY: n = a, c, g, or t
<222> LOCATION: (32)..(34)
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (34)..(34)
<223> OTHER INFORMATION: n is a, c, g, or t

<400> SEQUENCE: 72
aataattgca ataactctaa caaggtggaa cnan                              34

<210> SEQ ID NO 73
<211> LENGTH: 20

```
<212> TYPE: RNA
<213> ORGANISM: Artificial Sequence
<220> FEATURE:
<223> OTHER INFORMATION: guide sequence

<400> SEQUENCE: 73
ggccacgagu gugcacguau                                                      20

<210> SEQ ID NO 74
<211> LENGTH: 50
<212> TYPE: RNA
<213> ORGANISM: Artificial Sequence
<220> FEATURE:
<223> OTHER INFORMATION: synthetic

<400> SEQUENCE: 74
cguggcccug augaguccgu gaggacgaaa cgguaggaau uccuaccguc                     50

<210> SEQ ID NO 75
<211> LENGTH: 48
<212> TYPE: RNA
<213> ORGANISM: Artificial Sequence
<220> FEATURE:
<223> OTHER INFORMATION: synthetic

<400> SEQUENCE: 75
caccggaguc gacuccgguc ugaugagucc gugaggacga aauacgua                       48
```

VIRAL DELIVERY OF RNA UTILIZING SELF-CLEAVING RIBOZYMES AND CRISPR-BASED APPLICATIONS THEREOF

CROSS-REFERENCE TO RELATED APPLICATIONS

The present application claims priority to U.S. Provisional Patent Application Ser. No. 62/353,452, filed Jun. 22, 2016, the disclosure of which is hereby incorporated by reference in its entirety.

STATEMENT REGARDING FEDERAL FUNDING

This invention was made with government support under grant number R21 AI115226 awarded by the National Institute of Health (NIH). The United States government has certain rights in the invention.

FIELD OF THE INVENTION

The field of the invention generally relates to viral delivery of RNA utilizing self-cleaving ribozymes and CRISPR-based applications thereof.

BACKGROUND OF THE INVENTION

Gene therapies broadly involve the delivery of nucleic acid polymers (e.g. RNA or DNA) into a cell in order to treat an underlying disease or condition. One such gene therapy which has gained much attention over the last several years is CRISPR/Cas9. CRISPR/Cas9 technology promises to revolutionize genomics and modern medicine by allowing for the introduction of point-level mutations into a host genome, e.g. allowing the host genome to be cut at a desired location and then allowing genes to be removed or added. The CRISPR/Cas9 system generally relies on delivery of a specific nuclease, typically Cas9, into a cell, which is guided by guide RNA ("gRNA") to the appropriate section of the genome for cutting. Known viral vector systems for delivery of CRISPR/Cas9, e.g. lentivirus and adeno-associated virus (AAV), have successfully modified cells both ex vivo and in vivo; however, the DNA-based replication of these viruses carries the risk of unwanted integration into the host genome and thus genotoxicity or oncogenesis. Despite much attention to this problem and innovations such as the use of integration-defective lentivirus, undesirable integration remains a carefully monitored risk that may affect the success of future gene therapy trials. These drawbacks are not simply unique to CRISPR/Cas9. Accordingly, there is an urgent need for improved viral vector delivery systems, including for delivery of CRISPR-based technology.

SUMMARY OF THE INVENTION

The present disclosure relates to viral delivery of RNA utilizing self-cleaving ribozymes inserted into the RNA viral genome that are adjacent the target RNA to be delivered into the host cell, and particularly the use of such in CRISPR-based technology. Accordingly, in some embodiments, the present disclosure is directed to a nucleic acid. In some embodiments, the nucleic acid comprises a genome sequence of a single-stranded RNA (ssRNA) virus. In some embodiments, the genome sequence comprises antisense RNA. In some embodiments, the nucleic acid comprises an antigenome sequence. In some embodiments, the antigenome sequence is complementary to the genome sequence. In some embodiments, the antigenome sequence comprises sense RNA. In some embodiments, the antigenome sequence comprises a first region. In some embodiments, the genome sequence comprises a first region. In some embodiments, the first region comprises (i) a target segment and (ii) a first segment comprising a first self-cleaving ribozyme. In some embodiments, the first region further comprises (iii) a second segment encoding a second self-cleaving ribozyme. In some embodiments, the target segment is adjacent to the first segment. In some embodiments, the target segment is immediately upstream of the first segment. In some embodiments, the target segment is immediately downstream of the first segment. In some embodiments, the target segment is immediately upstream of the second segment. In some embodiments, the target segment is immediately downstream of the second segment. In some embodiments, the target segment is immediately upstream of a self-cleaving ribozyme. In some embodiments, the target segment is immediately downstream of a self-cleaving ribozyme. In some embodiments, the target segment is flanked by the first segment and the second segment. In some embodiments, the first self-cleaving ribozyme is a 5' self-cleaving ribozyme. In other embodiments, the first self-cleaving ribozyme is a 3' self-cleaving ribozyme. In some embodiments, the second self-cleaving ribozyme is a 5' self-cleaving ribozyme. In other embodiments, the second self-cleaving ribozyme is a 3' self-cleaving ribozyme. In some embodiments, the target segment is flanked by a 5' self-cleaving ribozyme and a 3' self-cleaving ribozyme. In some embodiments, the first region comprises an RNA expression cassette.

In some embodiments, the 5' self-cleaving ribozyme is a hammerhead ribozyme. In some embodiments, the 3' self-cleaving ribozyme is a hammerhead ribozyme. In some embodiments, both the 5' self-cleaving ribozyme and the 3' self-cleaving ribozyme are hammerhead ribozymes. In some embodiments, neither the 5' self-cleaving ribozyme and the 3' self-cleaving ribozyme are hammerhead ribozymes. In some embodiments, the 5' self-cleaving ribozyme includes SEQ ID NO: 2. In some embodiments, SEQ ID NO: 2 has conservative substitutions. In some embodiments, the 3' self-cleaving ribozyme includes SEQ ID NO: 3. In some embodiments, SEQ ID NO: 3 has conservative substitutions. In some embodiments, the 3' self-cleaving ribozyme is a hepatitis delta virus (HDV) ribozyme. In some embodiments, the 5' self-cleaving ribozyme is a hammerhead ribozyme and the 3' self-cleaving ribozyme is a hepatitis delta virus (HDV) ribozyme. In some embodiments, the 5' self-cleaving ribozyme is a twister ribozyme. In some embodiments, the 3' self-cleaving ribozyme is a twister ribozyme. In some embodiments, both the 5' self-cleaving ribozyme and the 3' self-cleaving ribozyme are twister ribozymes. In some embodiments, the 5' self-cleaving ribozyme is a twister sister ribozyme. In some embodiments, the 3' self-cleaving ribozyme is a twister sister ribozyme. In some embodiments, both the 5' self-cleaving ribozyme and the 3' self-cleaving ribozyme are twister sister ribozymes. In some embodiments, the 5' self-cleaving ribozyme is a pistol ribozyme. In some embodiments, the 3' self-cleaving ribozyme is a pistol ribozyme. In some embodiments, both the 5' self-cleaving ribozyme and the 3' self-cleaving ribozyme are pistol ribozymes. In some embodiments, the 5' self-cleaving ribozyme is a hatchet ribozyme. In some embodiments, the 3' self-cleaving ribozyme is a hatchet ribozyme. In some embodiments, both the 5' self-cleaving ribozyme and the 3' self-cleaving ribozyme are hatchet ribozymes. In some embodiments, the 5' self-cleaving ribozyme is a hairpin ribozyme. In some embodiments, the 3' self-cleaving ribozyme is a hairpin ribozyme. In some embodiments, both the 5' self-cleaving ribozyme and the 3' self-cleaving ribozyme are hairpin ribozymes.

In some embodiments, the antigenome sequence comprises a second region. In some embodiments, the genome sequence comprises a second region. In some embodiments, the first region is upstream of the second region. In some embodiments, the first region is downstream of the second region. In some embodiments, the second region comprises an expression cassette. In some embodiments, the second region comprises a third segment encoding a nuclease. In some embodiments, the nuclease comprises a CRISPR-associated protein ("Cas"). In some embodiments, the nuclease comprises Cas9. In some embodiments, the nuclease comprises Cpf1. In some embodiments, the nuclease comprises a Cas9-like protein or a Cas9-like synthetic protein. In some embodiments, the nuclease comprises a Cfp1-like protein or a Cfp1-like synthetic protein. In some embodiments, the nuclease comprises a C2c1 protein, C2c2 protein, C2c3 protein, or variants and modifications thereof. In some embodiments, the nuclease comprises Class 2 CRISPR-associated nuclease. In some embodiments, the nuclease comprises a Class 2 Type II CRISPR-associated nuclease. In some embodiments, the nuclease comprises a Class 2 Type V CRISPR-associated nuclease. In some embodiments, the second region further comprises a ribosomal skipping sequence. In some embodiments, the ribosomal skipping sequence is a P2A ribosomal skipping sequence. In some embodiments, the second region comprises a fourth segment encoding a reporter molecule. In some embodiments, the reporter molecule includes a protein. In some embodiments, the reporter molecule is green fluorescent protein (GFP). In some embodiments, the reporter molecule is red fluorescent protein (RFP). In some embodiments, the reporter molecule is mCherry. In some embodiments, the target segment comprises target RNA. In some embodiments, the target segment comprises guide RNA (gRNA). In some embodiments, the gRNA has a scaffold sequence and a targeting sequence. In some embodiments, the target segment further comprises trans-activating crRNA (tracrRNA).

In some embodiments, the antigenome sequence comprises a third region. In some embodiments, the genome sequence comprises a third region. In some embodiments, the third region is upstream of the first region. In some embodiments, the third region is downstream of the first region. In some embodiments, the third region is upstream of the second region. In some embodiments, the third region is downstream of the second region. In some embodiments, the third region is upstream of the first region and downstream of the second region. In some embodiments, the third region is downstream of the first region and upstream of the second region. In some embodiments, the third region is flanked by the first region and the second region. In some embodiments, the third region comprises a fifth segment. In some embodiments, the fifth segment comprises a P gene. In some embodiments, the P gene comprises a mutant P gene. In some embodiments, the mutant P gene has one or more of the following mutations: D433A, R434A, K437A, and combinations thereof.

In some embodiments, the antigenome sequence comprises a fourth region. In some embodiments, the genome sequence comprises a fourth region. In some embodiments, the fourth region is upstream of the first region. In some embodiments, the fourth region is downstream of the first region. In some embodiments, the fourth region is upstream of the second region. In some embodiments, the fourth region is downstream of the second region. In some embodiments, the fourth region is upstream of the first region and downstream of the second region. In some embodiments, the fourth region is downstream of the first region and upstream of the second region. In some embodiments, the fourth region is upstream of the first region, second region, and third region. In some embodiments, the fourth region is downstream of the first region, second region, and third region. In some embodiments, the fourth region is downstream of the first region, second region, and upstream of the third region. In some embodiments, the fourth region is upstream of the first region, second region, and downstream of the third region. In some embodiments, the fourth region is upstream of the first region, third region, and downstream of the second region. In some embodiments, the fourth region is downstream of the first region, third region, and upstream of the second region. In some embodiments, the third region comprises a sixth segment. In some embodiments, the sixth segment comprises a L gene. In some embodiments, the L gene comprises a mutant L gene. In some embodiments, the mutant L gene has one or more of the following mutations: N1197S, L15581, K1795E, and combinations thereof.

In some embodiments, the first region is heterologous. In some embodiments, the second region is heterologous. In some embodiments, the third region is heterologous. In some embodiments, the fourth region is heterologous. In some embodiments, the first region and the second region are heterologous. In some embodiments, the first region and the third region are heterologous. In some embodiments, the first region and the fourth region are heterologous. In some embodiments, the second region and the third region are heterologous. In some embodiments, the second region and the fourth region are heterologous. In some embodiments, the first region, second region and the third region are heterologous. In some embodiments, the first region, second region and the fourth region are heterologous. In some embodiments, the first region, second region, third region and the fourth region are heterologous. In some embodiments, the target segment is heterologous. In some embodiments, the first segment is heterologous. In some embodiments, the second segment is heterologous. In some embodiments, the third segment is heterologous. In some embodiments, the fourth segment is heterologous. In some embodiments, the fifth segment is heterologous. In some embodiments, the sixth segment is heterologous.

In some embodiments, the present disclosure is directed to an RNA expression cassette. In some embodiments, the expression cassette comprises a target sequence, a first segment encoding a self-cleaving ribozyme, and a second segment encoding a self-cleaving ribozyme. In some embodiments, the target segment is flanked by the first segment and the second segment. In some embodiments, the first self-cleaving ribozyme is a 5' self-cleaving ribozyme. In other embodiments, the first self-cleaving ribozyme is a 3' self-cleaving ribozyme. In some embodiments, the second self-cleaving ribozyme is a 5' self-cleaving ribozyme. In other embodiments, the second self-cleaving ribozyme is a 3' self-cleaving ribozyme. In some embodiments, the target segment is flanked by a 5' self-cleaving ribozyme and a 3' self-cleaving ribozyme. In some embodiments, the 5' self-cleaving ribozyme and the 3' self-cleaving ribozyme are hammerhead ribozymes. In some embodiments, the 5' self-cleaving ribozyme is a hammerhead ribozyme and the 3' self-cleaving ribozyme is a hepatitis delta virus (HDV) ribozyme. In some embodiments, the target sequence comprises guide RNA (gRNA). In some embodiments, the target sequence further comprises trans-activating crRNA (tracrRNA).

In some embodiments, the present disclosure is directed to a viral particle. In some embodiments, the viral particle comprises a nucleic acid according to any aspect of the present disclosure. In some embodiments, the viral particle is a single-stranded RNA (ssRNA) virus. In some embodiments, the genome of the ssRNA virus is of negative polarity. In some embodiments, the ssRNA virus is within the order mononegavirales. In some embodiments, the ssRNA virus is a Sendai virus. In some embodiments, the ssRNA virus is attenuated. In some embodiments, the first region is inserted between intergenic elements. In some embodiments, the intergenic elements are P and M elements. In some embodiments, the second region is inserted between intergenic elements. In some embodiments, the intergenic elements are N and P elements. In some embodiments, the viral particle comprises an RNA expression cassette according to any aspect of the present disclosure. In some embodiments, the RNA expression cassette is located in the 3' region of the viral genome. In some embodiments, the viral particle comprises a temperature sensitive mutant. In some embodiments, the viral particle comprises a PL mutant. In some embodiments, the PL mutant does not stimulate host interferon production.

In some embodiments, the present disclosure is directed to a method of introducing target RNA into a host cell. In some embodiments, the host cell is a prokaryotic cell. In some embodiments, the prokaryotic cell comprises a bacterial or archaebacterial cell. In some embodiments, the host cell is a eukaryotic cell. In some embodiments, the eukaryotic cell comprises a plant cell, an animal cell, a protist, or a fungal cell. In some embodiments, the animal cell comprises a vertebrate (chordate) cell. In some embodiments, the animal cell comprises an invertebrate cell. In some embodiments, the animal cell comprises a mammalian cell. In some embodiments, the method comprises the steps of (i) contacting the host cell with a viral particle according to any aspect of the present disclosure; and (ii) culturing the host cell under conditions allowing (a) producing a target RNA; and (b) liberating the target RNA, wherein the first self-cleaving ribozyme liberates the target RNA from the transcribed first region. In some embodiments, the host cell is selected from the group consisting of an archaea cell, bacterial cell, and a eukaryotic cell.

In some embodiments, the present disclosure is directed to a method of introducing a site-specific modification to target DNA in a host cell. In some embodiments, the host cell is a prokaryotic cell. In some embodiments, the prokaryotic cell comprises a bacterial or archaebacterial cell. In some embodiments, the host cell is a eukaryotic cell. In some embodiments, the eukaryotic cell comprises a plant cell, an animal cell, a protist, or a fungal cell. In some embodiments, the animal cell comprises a vertebrate (chordate) cell. In some embodiments, the animal cell comprises an invertebrate cell. In some embodiments, the animal cell comprises a mammalian cell. In some embodiments, the method comprises the steps of (i) contacting the host cell with a viral particle according to any aspect of this disclosure where the viral particle has a genome encoding a 5' self-cleaving ribozyme, gRNA, and a nuclease; (ii) culturing the host cell under conditions allowing (a) producing the gRNA flanked by the 5' self-cleaving ribozyme and the nuclease; (b) liberating the gRNA, wherein the 5' self-cleaving ribozyme liberates the gRNA, (c) expressing the nuclease; (d) forming a complex between the nuclease and the gRNA, wherein the scaffold sequence of the gRNA is bound to the nuclease; and (e) contacting the target DNA with the complex, wherein the targeting sequence of the gRNA binds to a sequence on the target DNA adjacent to a protospacer adjacent motif (PAM); and (iii) introducing the site-specific modification to the target DNA. In some embodiments, the site-specific modification is an insertion. In some embodiments, the site-specific modification is a deletion. In some embodiments, the site-specific modification is a frameshift. In some embodiments, the site-specific modification is a point mutation. In some embodiments, the site-specific modification is one of an insertion, a deletion, a frameshift, and a point mutation. In some embodiments, the DNA is genomic. In some embodiments, the DNA is chromosomal. In other embodiments, the DNA is extrachromosomal. In some embodiments, the DNA is mitochondrial DNA. In some embodiments, the DNA is chloroplast DNA. In some embodiments, the DNA is on a plasmid.

In some embodiments, the present disclosure is directed to a vector or vector system. In some embodiments, the vector comprises DNA encoding any nucleic acid of the present disclosure. In some embodiments, the vector is one or more plasmids. In some embodiments, the vector or vector system is one or more cosmids. In some embodiments, at least one plasmid has a T7-driven promoter element. In some embodiments, the present disclosure is directed to a cell transformed with a vector or vector system of any aspect of the present disclosure. In some embodiments, the cell is a bacterial cell. In some embodiments, the cell is *E. coli*. In some embodiments, the cell is *S. pyogenes*. In some embodiments, the cell is a fungal cell. In some embodiments, the cell is *S. cerevisiae* or *S. pombe*. In some embodiments, the cell is *P. pastoris*. In some embodiments, expression of one or more vectors is concomitant. In other embodiments, expression of one or more vectors is separately inducible.

In some embodiments, the present disclosure is directed to a kit. In some embodiments, the kit comprises a vector according to any aspect of the present disclosure. In some embodiments, the kit comprises a pharmaceutically acceptable preservative or carrier. In some embodiments, the kit further comprises reagents for expressing the DNA encoding the genome sequence or the antigenome sequence that is complementary to the genome sequence. In some embodiments, the reagents include polymerase. In some embodiments, the polymerase is T7 RNA polymerase. In some embodiments, the reagents include primers. In some embodiments, the kit further comprises instructions for use.

BRIEF DESCRIPTION OF THE DRAWINGS

FIG. 1A: The negative-sense RNA genome is flanked by virus promoters (the 3' leader (le), which serves as the genomic promoter, and the 5' trailer (tr), which serves as the antigenomic promoter). Shown are the Sendai virus genes N (nucleoprotein), P (phosphoprotein), M (matrix), F (fusion protein), HN (attachment protein), and L (large RNA-dependent RNA polymerase). An EGFP-P2A-Cas9 cassette (5.1 kb) was inserted between N and P, and a guide RNA flanked by self-cleaving ribozymes (rbz 1 and 2) (0.2 kb total) was inserted between P and M. The ribozymes are only functional in the positive-sense, or 5'-to-3', orientation. Genome may be transcribed from 3' to 5' into either full length antigenome or individual capped and polyadenylated mRNAs. These mRNAs are produced in a polar transcriptional gradient, with N mRNAs being the most abundant, and L mRNAs being the least abundant. FIG. 1B: The self-cleaving hammerhead ribozyme sequences (SEQ ID NO:2 and SEQ ID NO:3) and structures are shown. The chimeric guide RNA is shown in orange, corresponding to the orange highlight in FIG. 1A. Arrows indicate sites of cleavage. FIG. 1C: The self-cleavage activity of the ribozymes was assayed by qRT-PCR as described in Materials and Methods. Error bars represent standard deviation from 3 independent experiments. FIG. 1D: rSeV-Cas9 (WT), or rSeV-Cas9 with both ribozymes mutated to abolish self-cleavage (Mut), was rescued from plasmid DNA. As EGFP is only expressed upon conversion of transfected antigenome to genome and subsequent virus mRNA production, rescue efficiency was determined by observing GFP+ cells (rescue events) by flow cytometry at 1-2 days post-transfection (dpt). Error bars represent standard deviation from 3 replicates. ns, not significant. FIG. 1E: BSR-T7 cells were infected at a multiplicity of infection (MOI) of 0.01. Although the ribozymes in rSeV-Cas9 (WT) appear to affect growth compared to the mutant with no self-cleavage (Mut), they both reach the same peak titer of almost $10^8$ IU/mL. FIG. 1F: HEK293 cells in 6-well were transfected with 2 ug px330 (from which the FLAG-tagged Cas9 in rSeV-Cas9 was derived) or infected with rSeV-Cas9 at a MOI of 10. Cell lysates were collected 2 days later and processed via SDS-PAGE and Western blot analysis for detection of the FLAG epitope on Cas9. COX IV represents the loading control.

FIG. 2A: mCherry-inducible HEK293 cells were infected with rSeV-Cas9-control (no guide RNA) or rSeV-Cas9-mCherry (guide RNA targeting mCherry) at MOI 25. Expression of mCherry was induced with doxycycline (dox) after 4 days post-infection, and cells were collected for flow cytometry the following day. Percent knockout (KO) of mCherry fluorescence was determined as $100*(1-(C/(C+D)/(A/(A+B))$. Results from 3 independent experiments are shown. FIG. 2B: Cells treated as in panel FIG. 2A were imaged by fluorescence microscopy. The same exposure was used for each condition. FIG. 2C: rSeV-Cas9-mCherry was mutated to render Rbz 2 (Rbz 2-mut) or both ribozymes (Rbz 1/2-mut) non-functional. An alternative 3' ribozyme, the hepatitis delta virus (HDV) ribozyme, was also tested via replacement of Rbz 2. The experiment was performed as in FIG. 2A. FIG. 2D: HEK293 cells were infected with rSeV-Cas9-control or rSeV-Cas9-mCherry at MOI 25 and collected for deep sequencing of the mCherry locus at 6 days post-infection. Error bars represent Jeffreys 95% confidence intervals. The 5 most abundant species of mutated target (SEQ ID NOs: 44-49, respectively) and their relative abundance percentages are shown. Highlights represent the 20 bp target sequence, the arrowhead represents the Cas9 cleavage site, and the 3 bp PAM motif is shown.

FIG. 3A: Affinofile cells were infected with rSeV-Cas9-control or rSeV-Cas9-CCR5 at MOI 25. CD4/CCR5 overexpression was induced at day 2, and cells were further infected with CCR5-tropic HIV-1 the following day. Flow cytometry for p24 and CCR5 was performed 5 days after infection with rSeV. Data shown is gated on rSeV-infected cells (GFP+).

FIG. 4B: Primary human monocytes from an independent donor were infected as in panel a, and cells were collected at 5 days post-infection for flow cytometry of cell surface CCR5. Data shown is gated on infected cells (GFP+).

FIG. 5A: mCherry-inducible HEK293 cells were infected with rSeV-Cas9-control or rSeV-Cas9-mCherry at MOI 25. mCherry expression was induced with doxycycline at the indicated days post-infection, and cells were collected for flow cytometry the following day. FIG. 5B: Histograms of mCherry expression (gated on infected GFP+ cells) are shown below as an alternative comparison.

FIG. 8A shows a schematic of the specific P and L mutations. FIG. 8B shows the temperature sensitive phenotype of the PL mutants.

FIG. 9A shows the same schematic from FIG. 8A for reference. The gRNA is targeted against CCR5 and is the exact gRNA that was used in Example 1. FIG. 8B shows PL mutant transduction/infection of purified human fetal liver CD34+ and peripheral blood mobilized CD34+ HSCs (>90% GFP+ at 2 days post-infection (dpi) using an MOI of 5; infection performed at 34° C.). FIG. 9C shows time course of infection at 34° C. vs 37° C. CD34+ HSCs were infected at 34° C. for 2 days and then either maintained at 34° C. or shifted to 37° C. at 2 dpi. The GFP+ cells steadily declined. FIG. 9D shows Sanger sequencing data from PL mutant-infected CD34+ HSCs at 2 dpi. 19/24 clones (~80%) showed indels at the targeted CCR5 locus. The wild type and first four clones have SEQ ID NOs: 68-72, respectively.

FIG. 12A represents a schematic of the PL mutant. FIG. 12B represents a schematic of a PL mutant modified to be missing the Fusion protein (ΔF) and a target RNA delivery region modified to deliver two gRNAs; CCR5 and HRPT, both flanked by hammerhead and HDV self-cleaving ribozymes.

DETAILED DESCRIPTION OF THE INVENTION

One embodiment of the present disclosure relates to novel nucleic acids, including but not limited to, RNA expression cassettes. The nucleic acids generally relate to genetically modified genomes or antigenomes complementary to the genomes of ssRNA viruses, e.g. the Sendai virus (SeV). The genome of mononegavirales, including but not limited to paramyxoviruses and SeV, is antisense RNA (i.e. having negative polarity). Thus, when the present specification refers to a nucleic acid comprising a genome sequence of a single-stranded RNA (ssRNA) virus, the genome sequence is understood as being antisense RNA. The antigenome sequence is therefore sense RNA. Accordingly, an RNA antigenome transcribed from the negative polarity genome of, e.g. Sendai virus, will contain sense RNA. mRNA transcribed from the genome of an ssRNA virus will likewise contain sense RNA that can be translated, or in the instance where the mRNA contains a target sequence adjacent to one or more self-cleaving ribozymes (e.g. flanked by self-cleaving ribozymes), the self-cleaving ribozymes will be able to liberate the target sequence. Because the antigenome of the present disclosure is oriented in the 5' to 3' direction, similar to the biologically active mRNA transcribed from the negative polarity genome, elements of the nucleic acids of the present disclosure are typically referred to by their antigenome components. However, the invention as described herein is explicitly not limited to just the antigenome components, as the genomic components, e.g. as contained within the viral particles of the present disclosure (discussed infra) represent novel nucleic acids that may be transcribed in vitro or in vivo into an antigenome or antigenomic elements thereof or transcribed into mRNA fragments which undertake a biologically active role.

Figure 1:
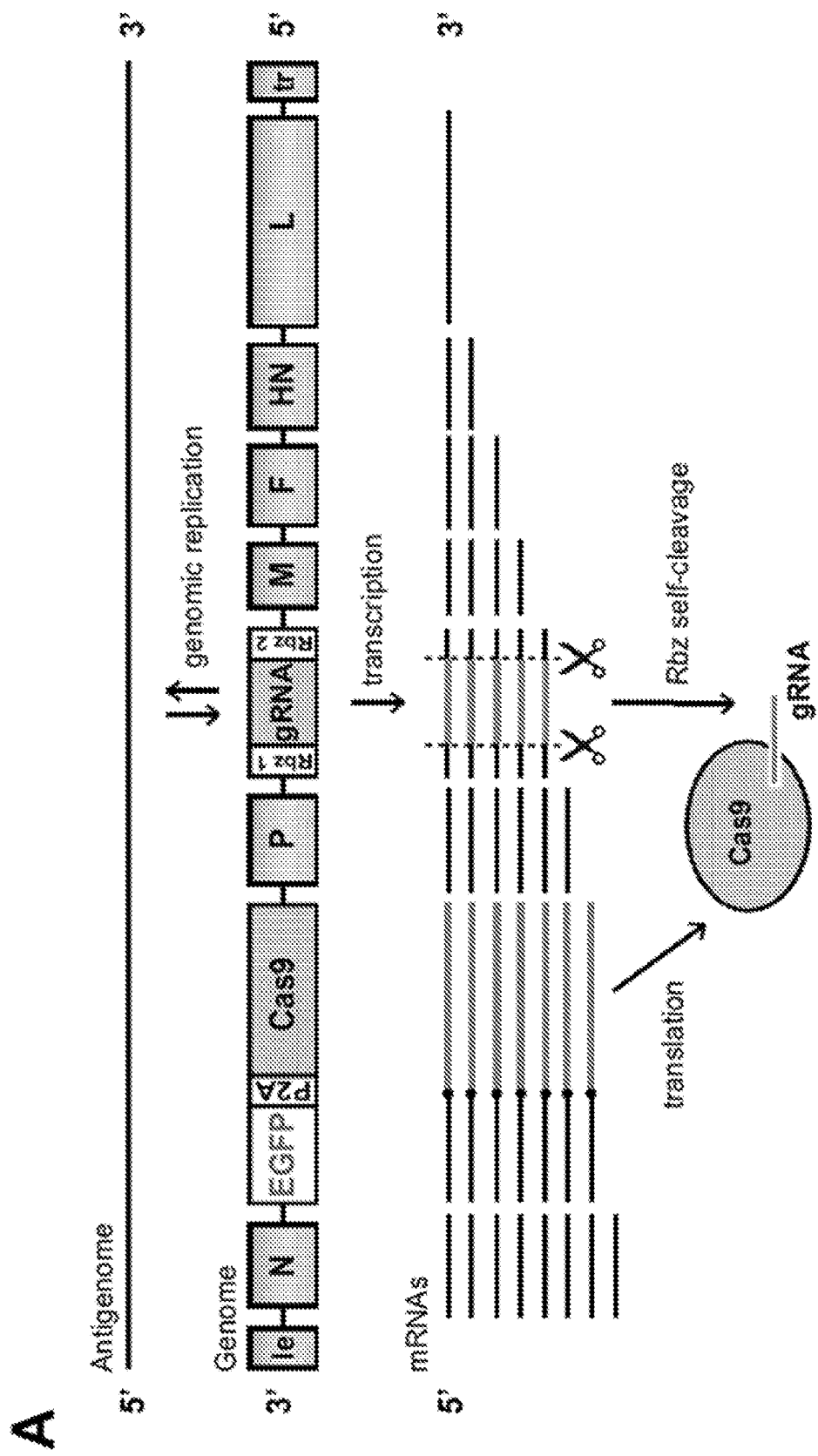
FIG. 1 represents Sendai virus incorporating Cas9 and a guide RNA (gRNA) flanked by self-cleaving ribozymes replicates to high titer.
Figure 1:
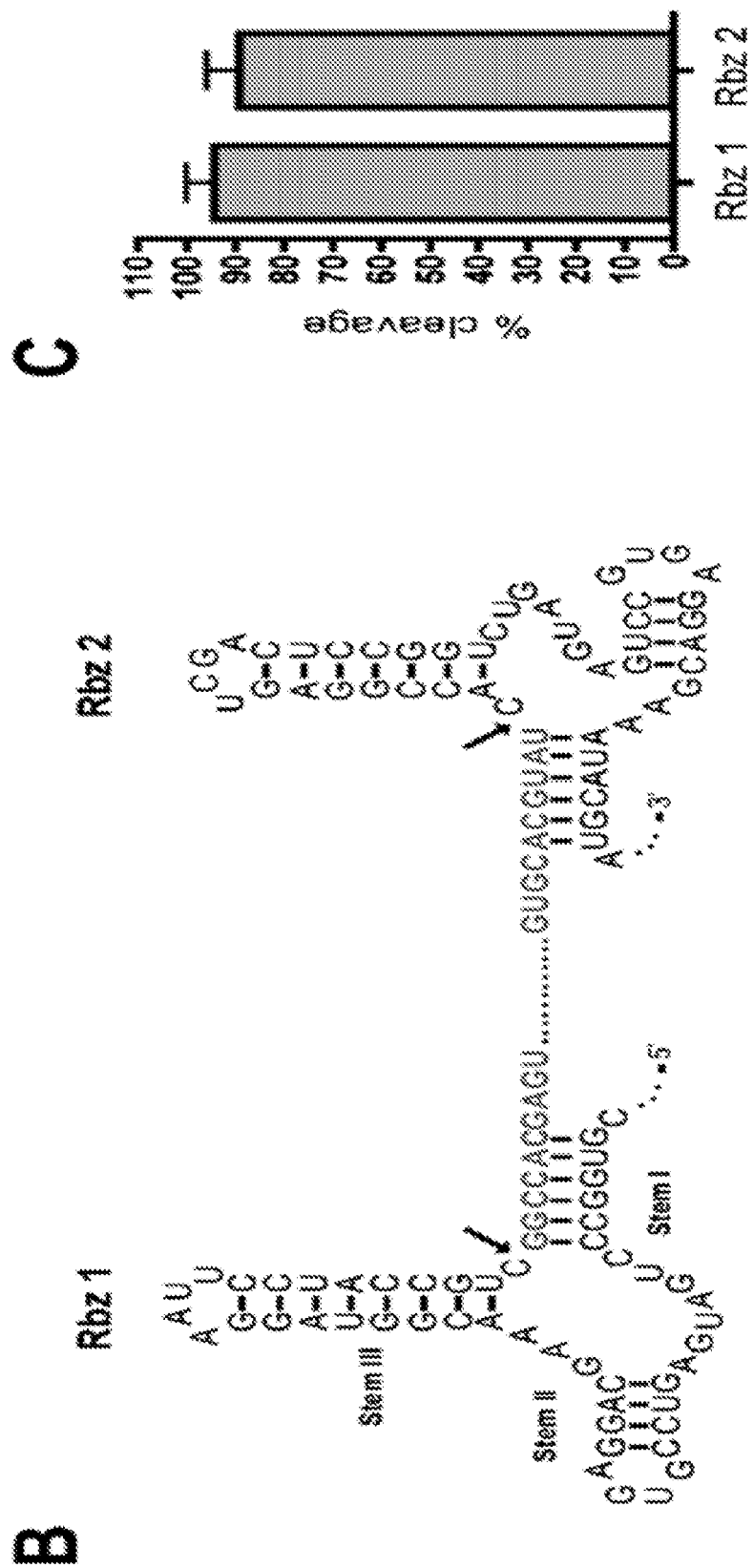
Figure 1:
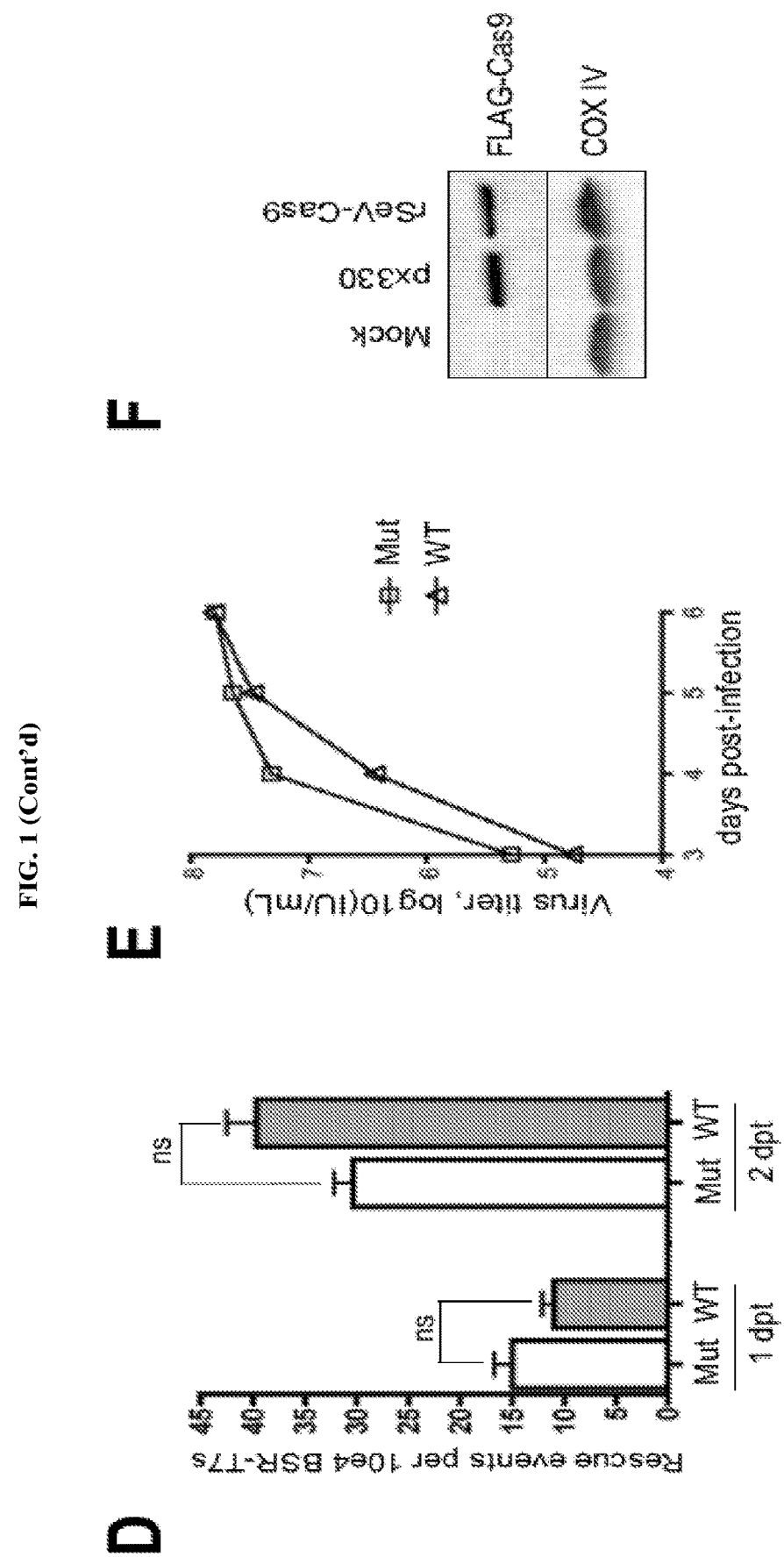
Figure 2:
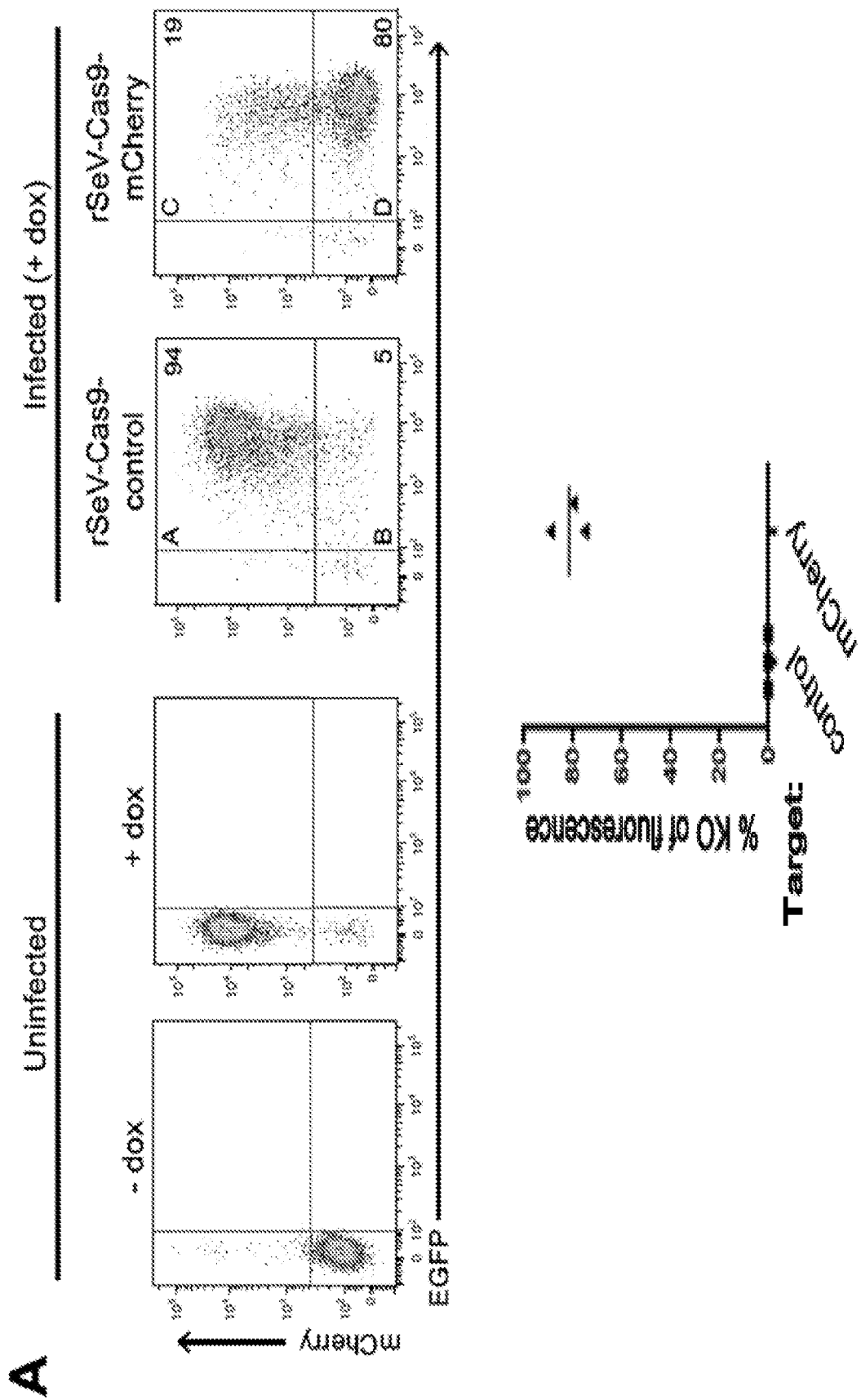
FIG. 2 represents rSeV-Cas9 targeting mCherry gene achieves almost complete mutagenesis of a reporter cell line.
Figure 2:
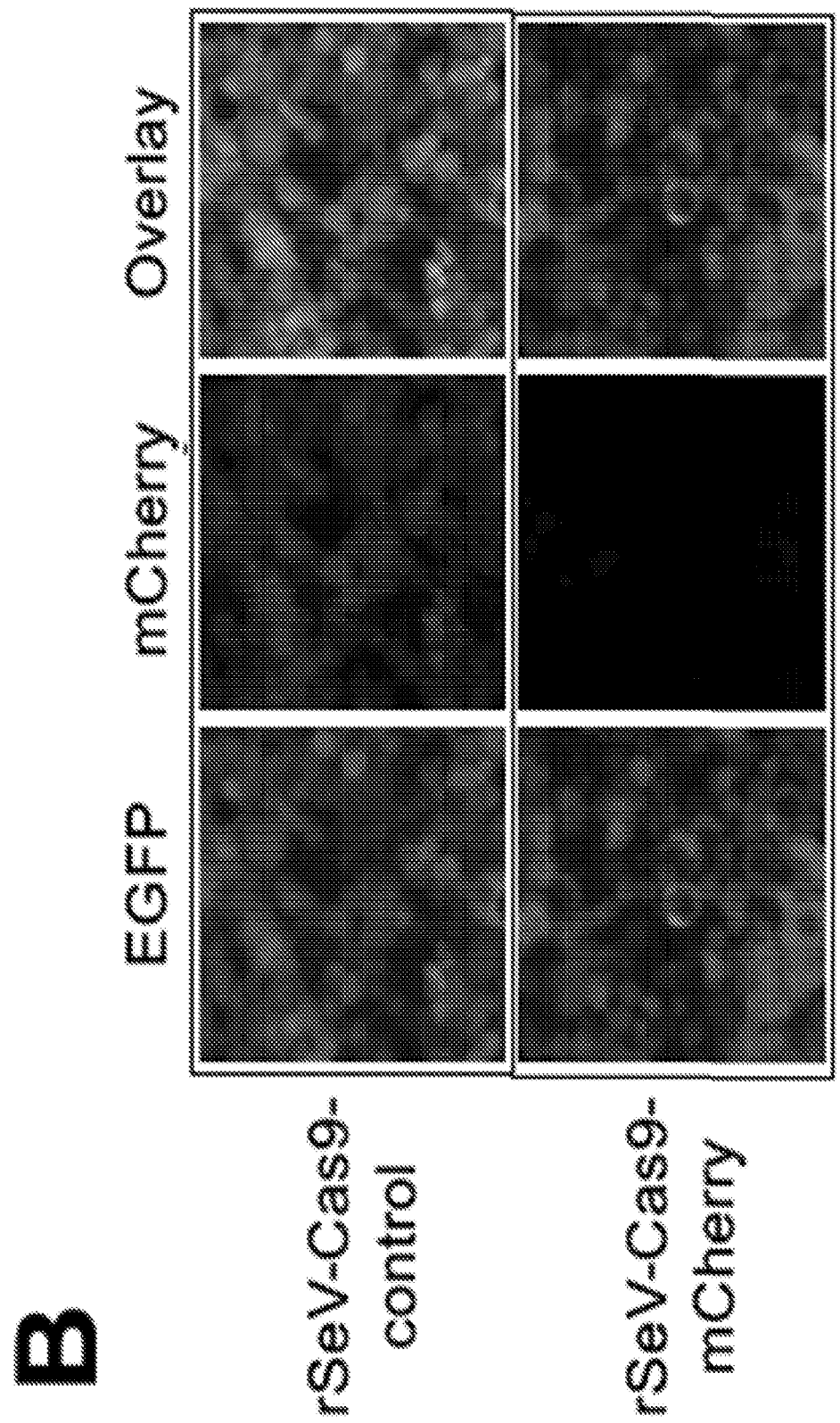
Figure 2:
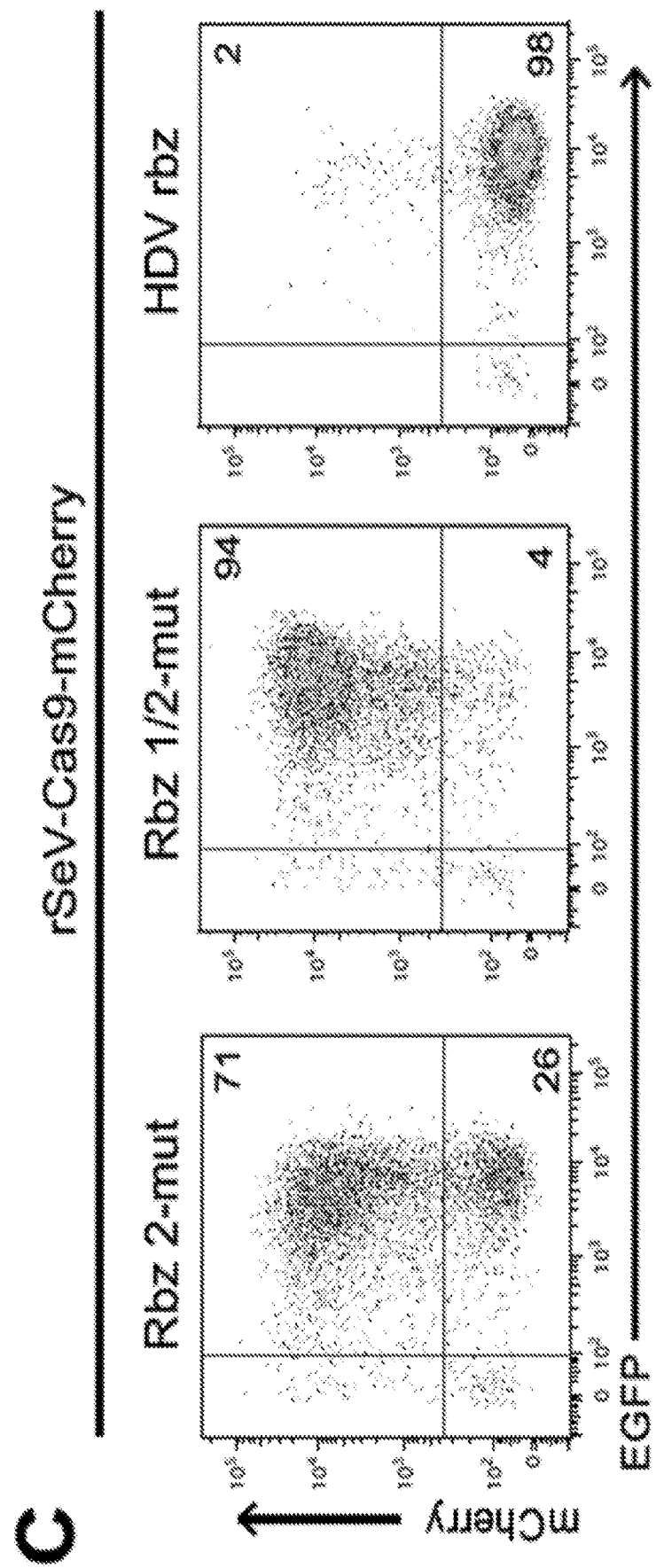
Figure 2:
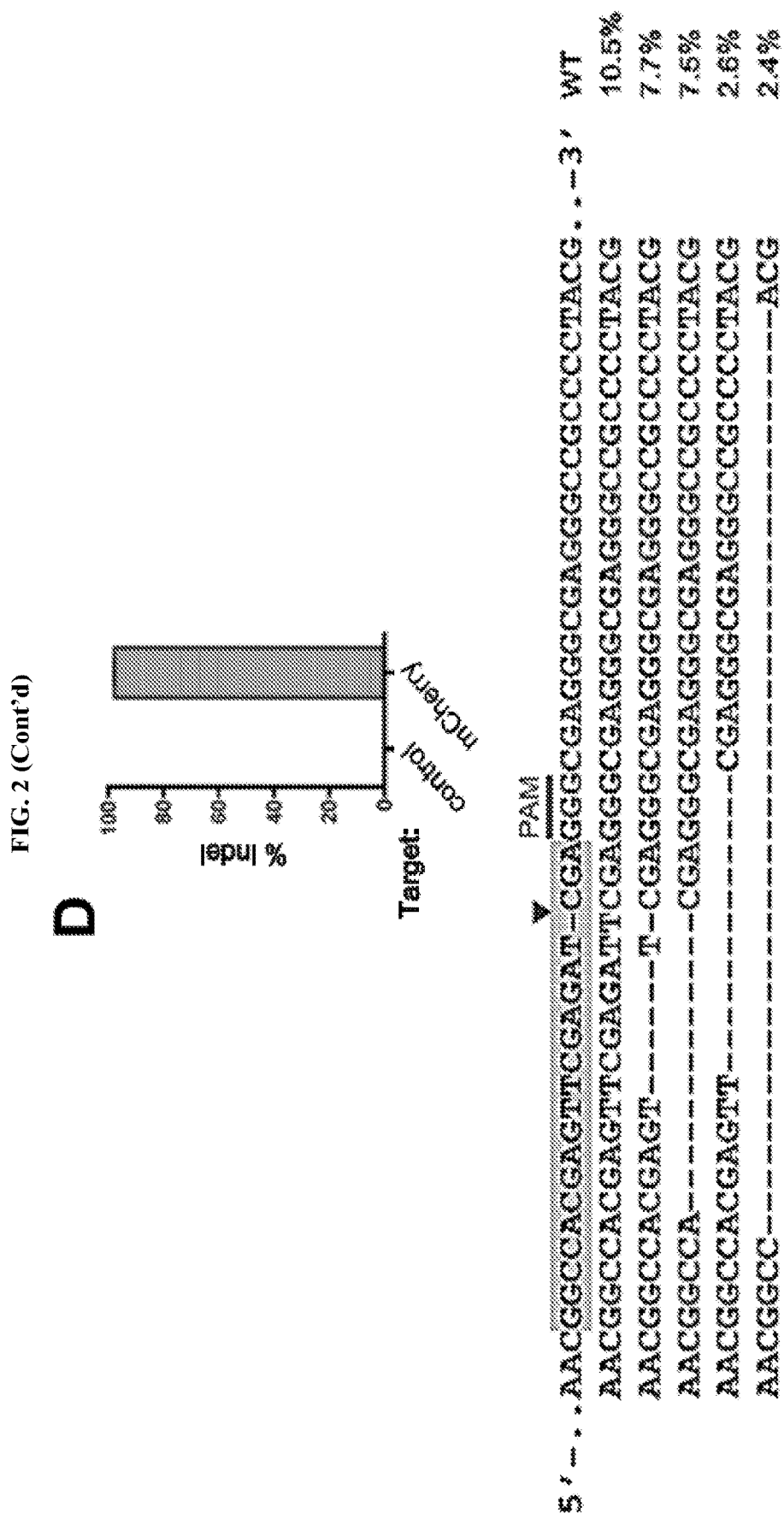

The antigenome sequences of the present disclosure generally comprise a first region comprising (i) a target segment, and (ii) a first segment encoding a first self-cleaving ribozyme. The target segment is to be understood as being a payload, e.g. an RNA payload, that is capable of being liberated from mRNA transcribed from the genome by the one or more self-cleaving ribozymes adjacent to the target segment. This self-cleaving ribozyme may be either a 5' self-cleaving ribozyme or a 3' self-cleaving ribozyme. Preferred embodiments of the present disclosure utilize both a 5' self-cleaving ribozyme and a 3' self-cleaving ribozyme that flank the target segment to be delivered to the cell. FIG. 2C illustrates that while it is preferable to have both 5' and 3' self-cleaving ribozymes present, only one is truly necessary for the invention to work in this aspect. However, while not wishing to be bound by theory, it is believed that for methods involving introduction of site-specific modifications to target DNA (i.e. CRISPR-related applications), at least one 5' self-cleaving ribozyme must be present. This is because the targeting sequence of gRNA is located on the 5' end of the gRNA and small alterations to such may result in a loss of targeting ability. However, for general delivery of target segments, e.g. target RNA to a cell, either a single 5' self-cleaving ribozyme or a 3' self-cleaving ribozyme will be sufficient. The general concept of the present disclosure with respect to this aspect is that the genome and the antigenome sequences can "store" (i.e. encode) one or more self-cleaving ribozymes without being active, as they are only biologically active once transcribed into mRNA from the genome sequences. While not wishing to be bound by theory, it is believed that although the antigenome contains the ribozyme(s) in the same orientation as mRNA transcribed from the genome, the self-cleaving ribozymes are not active in the antigenome. This is believed to be due to co-transcriptional encapsidation of the genomic and antigenomic RNA by the viral nucleocapsid protein. This is significant because if the antigenome was self-cleaving, production of additional full-length genomes from the antigenome would be impossible. Therefore, the ribozymes of the present disclosure are considered only active in the mRNAs transcribed from the genome, which are not encapsidated by the nucleocapsid protein which encapsidates the viral antigenome (represented by N in FIG. 1). Once mRNA is transcribed from the viral genome, the self-cleaving ribozymes activate and cleave themselves and by doing so, liberate the target segment that they are either adjacent to (in the case of a single self-cleaving ribozyme) or flank (in the preferred case of two self-cleaving ribozymes). The target segment is then free to serve any particular utility in the cell which transcribed the viral genome.

The self-cleaving ribozymes of the present disclosure can take a number of forms. The exemplary self-cleaving ribozymes are hammerhead ribozymes, as shown in FIG. 1A. However, other self-cleaving ribozymes may be used, including hepatitis delta virus (HDV) ribozymes. It is important to note that as detailed herein, HDV ribozymes may only be utilized as 3' self-cleaving ribozymes, whereas hammerhead ribozymes may be utilized in both 5' and 3' self-cleaving ribozymes. Other self-cleaving ribozymes which may be utilized include twister (e.g. Twiser from *O. sativa*, env9, and env22), twister-sister, pistol, hatchet, hairpin, *Neurospora* VS, and glmS ribozymes. Self-cleaving ribozymes are generally characterized by distinct active site architectures and divergent, but similar, biochemical properties. The cleavage activities of self-cleaving ribozymes are highly dependent upon divalent cations, pH, and base-specific mutations, which can cause changes in the nucleotide arrangement and/or electrostatic potential around the cleavage site. Self-cleaving ribozymes are detailed in Weinberg et al., 2015, *Nature Chemical Biology*, "New classes of self-cleaving ribozymes revealed by comparative genomics analysis" and Lee et al., 2017, *Molecules*, "Structural and Biochemical Properties of Novel Self-Cleaving Ribozymes," both references hereby incorporated by reference in their entireties. Without wishing to be bound by theory, the mechanism of action of most self-cleaving ribozymes is based in acid-base catalysis of guanine and adenine in close proximity of the cleavage site. Additionally, metal ions are believed to play a structural rather than catalytic role, despite the fact that some crystal structures have shown a direct metal ion coordination to a non-bridging phosphate oxygen at the cleavage site. As new self-cleaving ribozymes arise, they too will be considered to be within the scope of this disclosure, so long as they are capable of self-cleaving and successfully delivering target segments (e.g. RNA payloads) to a target cell when transcribed from a ssRNA viral genome.

As an exemplary method of use of the novel nucleic acids, the target segments may comprise guide RNA (gRNA), and/or tracrRNA. In such embodiments, the nucleic acids may further (but not necessarily) comprise a second region. The second region of the genome may contain a nucleotide sequence that, when transcribed, produces mRNA that is capable of being translated to code for a nuclease, e.g. Cas9, including but not limited to Cas9 homologs, or Cpf1, although other nucleases may be suitable for incorporation into the present disclosure. An exemplary embodiment of this nucleic acid is shown at FIG. 1A. In such embodiments, the first region and the second region may be subcloned into different locations within the ssRNA viral genome. One particular consideration in where to subclone the first region/second region is the rate of transcriptional activity relative to genome location. For example, with SeV, an exemplary ssRNA virus, transcription is more active in the 3' region of the viral genome, thus a region (or expression cassette) that is located in the 3' region of the genome will be overexpressed relative to an region (or expression cassette) located within the 5' region of the viral genome. This trait is common to all paramyxoviruses, which carries with it the strong implication that success achieved with SeV, as shown in Example 1 infra, translates to the other members of the family. Thus there may be various benefits to cloning such regions closer to or farther from the 5' or 3' end of the viral genome. The takeaway is that the location of cloning into the viral genome of the first region and the second region is discretionary, and that the emphasis should be on the composition of the regions themselves, and not the remainder of the viral genome elements.

Another aspect of the present disclosure relates to viral particles that comprise the foregoing nucleic acids discussed in the above section titled "nucleic acids." As mentioned supra, the nucleic acids of the present disclosure relate to modified genomes and antigenomes of ssRNA viruses. Thus, this aspect of the disclosure relates to the modified ssRNA viruses. As previously discussed, any ssRNA virus where the RNA is negative polarity (i.e. antisense) is considered to be within the scope of this disclosure and thus suitable for use. Explicitly, the viruses of the order mononegavirales are considered to be within the scope of this disclosure. This is because viruses of the order mononegavirales have common attributes that lend them suitable to incorporate the nucleic acids of the present disclosure. Mononegavirales possess a linear, single-stranded, non-infectious RNA strand having negative polarity. Mononegavirales have characteristic gene order, produce 5-10 distinct mRNAs via polar sequential transcription, and replicate by synthesizing complete antigenomes.

Families within mononegavirales include bornaviridae, filoviridae, nyamiviridae, paramyxodiridae, and rhabdoviridae. Genera within bornaviridae include bornavirus. Genera within filoviridae include cuevavirus, ebolavirus, and marburgvirus. Genera within nyamiviridae include nyavirus. Genera within paramyxoviridae include aquaparamyxovirus, avulavirus, feravirus, heniparvirus, morbillivirus, respirovirus, rubulavirus, pneumovirus, and metapneumovirus. Genera within rhabdoviridae include alemndravirus, baiavirus, curiovirus, cytorhabdovirus, dichorhavirus, ephemerovirus, hapavirus, ledantevirus, lyssavirus, novirhabdovirus, nuclearhabdovirus, perhabdovirus, sawgravirus, sigmavirus, sprivivirus, tibrovirus, tupavirus, and vesiculovirus. While one of ordinary skill in the art will readily realize that not all of these candidates may be as suitable for incorporation into certain embodiments of the present disclosure as paramyxoviridae, including but not limited to Newcastle disease virus (NDV) and the Sendai virus, each of these viruses possess the necessary features from a compositional standpoint to incorporate the nucleic acids of the present disclosure.

Viral particles of the present disclosure may be generated by routines known to those of ordinary skill in the art. For example, the viral particles of the present disclosure may be generated from packaging cells that are transfected with vectors, e.g. one or more plasmids of the present disclosure, that contain DNA encoding a nucleic acid of the present disclosure, e.g. a viral genome or antigenome of the present disclosure. This allows for scalable production of the viral particles, especially in instances where the viral particles are attenuated, e.g. not replication-competent. Expression of the vectors is induced in the packaging cells and the viruses assemble for harvesting. This process is exemplified in Example 1, where *E. coli* cells were transfected with plasmid containing elements of the rSev-Cas9 recombinant genome/antigenome. Other packaging cells are known to one of ordinary skill in the art and may include, but are explicitly not limited to, HEK293 cells and PA317 cells.

Of the ssRNA viruses suitable for the present disclosure, the Sendai virus (SeV) is of particular interest, and is an exemplary virus used throughout Example 1 infra. The present disclosure has surprisingly shown that certain ssRNA viruses, e.g. paramyxoviruses, exemplified by the Sendai virus, can tolerate self-cleaving ribozymes within the genome. While not wishing to be bound by theory, as discussed supra, this is likely due to co-transcriptional encapsidation of the genomic and antigenomic RNA by the nucleoprotein and thus prevention of ribozyme activity during replication of the full-length RNA. Along with further incorporation of Cas9 expression, the rescued replication-competent virus was able to efficiently induce mutagenesis of the guide RNA target sequence in the genome. For example, although the efficiency of the ccr5-targeting virus is not directly comparable to other studies due to the differing guide RNA sequences and target cells used, rates of ccr5 mutagenesis (75-88%) was achieved similar to or higher than those achieved via lentivirus or AAV CRISPR/Cas9 transduction. Further, because infection with Sendai virus was highly efficient, achieving these high rates of mutagenesis did not require sorting or selection for infected cells, another distinct advantage.

In addition to the advantages of broad tropism, growth to high titers, and robust expression of foreign genes previously mentioned, ssRNA viruses, e.g. Sendai virus, have additional important advantages as a gene therapy vector. First, such viruses are amenable to envelope switching or modification, in which envelope proteins with different cell type specificities can be substituted for the original, or the original attachment or fusion protein itself can be modified to have a different specificity. Second, Sendai virus, like other paramyxoviruses, has a polar transcriptional gradient (FIG. 1A) with reduction of transcript levels as the polymerase complex moves from the 3' to 5' end of the genome.

The efficiency versus the specificity of Cas9 activity appears to be a trade-off, and the optimal levels of Cas9 and guide RNA expression therefore likely must be determined for each CRISPR delivery platform. Thus, for paramyxoviruses in particular, levels of Cas9 and guide RNA expression can be modulated and fine-tuned by shifting the inserted regions of these introduced elements within the genome, or by modifying the strength of gene start signals. Third, paramyxoviruses are not prone to genetic recombination or instability, and no homologous or heterologous recombination has ever been detected for Sendai virus. Fourth, despite a high prevalence of immunity to the related human parainfluenza virus-1, cross-neutralizing anti-Sendai virus titers are low. Thus, Sendai virus, as a mouse pathogen, would not encounter significant pre-existing specific immunity in humans, making Sendai virus in particular a highly attractive target for gene therapy, e.g. delivery of a RNA target to a cell.

Although the disclosure is strictly not limited to Sendai virus (SeV), the Sendai virus has several characteristics that render it surprisingly effective. The Sendai virus has been extensively studied and modified to develop temperature-sensitive, non-cytopathic, and replication-incompetent Sendai viruses that are useful for ex vivo and in vivo gene therapy applications. Mutations and variants of Sendai virus have been characterized that allow replication of Sendai virus at a permissive temperature until a temporary shift to a non-permissive temperature, after which replication is blocked and can no longer be detected. Such control of Sendai viral replication with temperature sensitivity can allow for temporal control of Cas9 and guide RNA expression, which would reduce off-target effects by removing the vector once editing is complete, again speaking to the particular utility of the Sendai virus. Mutations that further confer the ability to avoid triggering innate immune responses and concomitant cytopathogenicity would avoid disturbing sensitive cell types such as hematopoietic stem cells or other primary cells. Finally, the Sendai virus is amenable to single and multiple deletions of the envelope and/or matrix genes such that the virus can only replicate when these viral factors are supplied in trans. Upon infection of target cells in the absence of these exogenously supplied factors, the virus can produce the factors encoded on its genome but cannot amplify via production of subsequent infectious virus.

Example 2 infra illustrates preferred embodiments of the recombinant Sendai viral vectors, having mutant P and L genes, designated as PL mutants. The PL mutants are temperature sensitive, efficiently transfecting at 34° C. but not at 37° C. More surprisingly, however, is that the PL mutants do not induce a host interferon (IFN) response, i.e. do not stimulate production of IFN in a host when infected with the PL mutant vectors. The IFN-silent phenotype is particularly important when applying the viral vectors to sensitive cells like CD34+ hematopoietic stem cells where induction of IFN can drive differentiation and compromise "sternness". Accordingly PL mutants, particularly PL mutants of the Sendai virus, represent a surprisingly effective vehicle for RNA transfection in a host cell, e.g. stem cell.

The viral particles of the present disclosure may be utilized to introduce an RNA payload into a target cell, e.g. a gRNA payload in the case of CRISPR-related applications. Generally, the a host cell is infected with a viral particle of the present disclosure and the host cell is cultured under conditions that allow for the liberation of the target RNA. Cell culturing techniques are known to one of ordinary skill in the art. As detailed supra, transcription of the viral genome or a portion of the viral genome, e.g. transcription of an RNA expression cassette inserted into the viral genome, into mRNA allows for the one or more self-cleaving ribozyme(s) to cleave themselves out of the transcribed mRNA and the target RNA along with it. In such embodiments, there need be only one self-cleaving ribozyme present, e.g. 5' self-cleaving ribozyme or a 3' self-cleaving ribozyme. The self-cleaving ribozyme must be adjacent to or flank the target RNA payload so that it is capable of liberating the payload upon transcription of the viral genome into mRNA.

The target RNA may be, e.g., microRNA (miRNA), gRNA, or any other RNA. The RNA payload does not have to have any particular therapeutic use, but one of ordinary skill in the art can envision many such uses. For example, the target RNA may be involved in RNA silencing. The RNA may be utilized to regulate gene expression, e.g. post-transcriptionally. Some non-limiting examples of a target RNA include siRNA and miRNA, which may or may not have specific therapeutic uses. siRNA may be utilized for RNA interference (RNAi) to promote gene silencing. miRNAs are used for similar therapeutic end means, and may represent a particularly useful therapeutic non-CRISPR related application of the present disclosure. miRNAs are currently being utilized to treat many distinct types of diseases, from autoimmune disease to neurodegenerative disorders to cancer. miRNAs are typically endogenous 17-24 base-long single-stranded, non-coding RNAs that regulate gene expression in a sequence-specific manner in plants and animals. Endogenously, miRNAs are derived from longer RNA transcripts by Drosha and Dicer. The resultant miRNAs bind to their target sequence, typically within the 3' untranslated region (UTR) of mRNA, thus leading to repression of translation. The present disclosure provides an alternative delivery mechanism for miRNA by simply cleaving the miRNA from the transcribed antigenome, e.g. by flanking self-cleaving ribozyme(s). One of ordinary skill in the art will appreciate that the class of miRNAs which can be delivered in this manner are vast, and are not considered to be limited according to the therapeutic use of such, rather they are to be considered within the scope of delivering a target RNA to a cell according to the present disclosure.

An exemplary use of the nucleic acids/viral particles of the present disclosure relates to gene editing via CRISPR-related technology. CRISPR stands for clustered regularly interspaced short palindromic repeats type II system. CRISPR is a bacterial immune system that is modified for genetic engineering purposes. Prior to CRISPR the most common genomic engineering approaches utilized zinc finger nucleases. CRISPR relies on two components, a guide RNA (gRNA) and a non-specific CRISPR-associated endonuclease, e.g. Cas9. The gRNA is a synthetic RNA having a scaffold sequence and a target sequence. The scaffold sequence is necessary for binding to the nuclease, e.g., Cas9. The targeting sequence, often approximately (although explicitly not necessarily) 20 nucleotides in length, defines the genomic target to be modified. Thus, one of ordinary skill in the art can change the genomic target by simply changing the targeting sequence present in the gRNA. The genomic target can be any ~20 nucleotide DNA sequence, provided it meets two conditions: 1) the sequence is unique compared to the rest of the organism's genome and 2) the target is present immediately upstream of a Protospacer Adjacent Motif (PAM). The PAM sequence is dependent upon the exact species from which the nuclease was originally derived from. For example, the PAM for Cas9 derived from *S. pyogenes* is 5'-XGG-3', wherein X is any nucleobase, whereas the PAM for Cfp1 is 5'-TTX-3'. One of ordinary skill in the art will be familiar with different nucleases, e.g. Cas9 and related proteins, and their corresponding PAMs.

Cas9 was originally isolated from *S. pyogenes*, and while that remains an exemplary nuclease in the disclosure, there are many different nucleases, including Cas9 variants, which are suitable for use in this aspect of the disclosure. For example, there are synthetic Cas9 proteins that have artificial PAM recognition sequences, e.g. as described in Kleinstiver B P et al., *Nature,* 2015 Jun. 23; 523(7561):481-5, hereby incorporated by reference in its entirety. There are Cas9 homologs derived from organisms other than *S. pyogenes*, for example, Cas9 from *S. aureus* (SaCas9). SaCas9 is approximately 1 kilobase smaller in size than Cas9 from *S. pyogenes*, which may render it more suitable for incorporation into the viral particles of the present disclosure due to the limited genome size of some viral particles, although this is not an issue for Sendai virus as illustrated in Example 1 infra. One of ordinary skill in the art will appreciate that Cas9 derived from other organisms are only compatible with tracrRNA and crRNA or synthetic gRNA derived from the same host species. Furthermore, there are alternatives to Cas9 derived from *S. pyogenes*, synthetic Cas9, or Cas9 homologs. One such alternative is Cpf1, described in Zetsche B et al., Cell. 2015 Oct. 22; 163(3):759-71 and Kleinstiver B. P. et al., *Nature Methods* 2016 Aug. 30; 714(13), both references incorporated by reference in their entireties. Cpf1 has a PAM of 5'-TTX-3, wherein X is any nucleobase, and is located immediately upstream of the target DNA, instead of the target DNA being immediately upstream of the PAM in the case of Cas9. Furthermore, Cpf1 cleavage results in a 5 nucleotide 5' overhang 18 base pairs from the PAM sequence, whereas Cas9 cutting results in blunt DNA ends 3 base pairs distal to the PAM sequence. Additionally, Cpf1 only requires CRISPR RNA (crRNA) for successful targeting whereas Cas9 requires both crRNA and transactivating crRNA (tracrRNA). Further CRISPR proteins may include C2c1, C2c2, and C2c3 proteins, disclosed in, for example, Shmakov et al., *Molecular Cell* 2015 Oct. 22; 60(3): 385-397, hereby incorporated by reference in its entirety.

CRISPR-Cas gene editing systems have recently been reclassified into two primary classes spanning five types and sixteen subtypes, reviewed in Makarova, K., et al., *Nature Reviews Microbiology* 13:1-15 (2015), hereby incorporated by reference in its entirety. Classification was based upon identifying all cas genes in a CRISPR-Cas locus and subsequently determining key genes in each locus. This lead to a conclusion that currently known CRISPR-Cas systems can classified as either "Class 1" or "Class 2" depending on the genes encoding the proteins involved in the interference stage. A recent sixth CRISPR-Cas system has been identified, described in Abudayyeh O., et al. *Science* 2016, hereby incorporated by reference in its entirety.

"Class 1" systems generally comprise a multi-subunit crRNA-effector complex, whereas "Class 2" systems generally comprise a single protein, such as Cas9, Cpf1, C2c1, C2c2, C2c3, or a crRNA-effector complex. Class 1 systems comprise "Type I," "Type III" and "Type IV" systems. "Class 2" systems comprise "Type II" and "Type V" systems. Class 1 CRISPR-Cas systems are characterized by effector modules consisting of multiple subunits. Class 1 systems comprise about 90% of all CRISPR-Cas loci identified in bacteria and archaea and can target both DNA and RNA, as described in Makarova et al., *Cell* (2017) 168(5), hereby incorporated by reference in its entirety.

Type I systems are characterized by a Cas3 protein that has helicase activity and cleavage activity. Type I systems are further divided into seven specific sub-types (I-A, I-B, I-C, I-D, I-E, I-F, and I-U). Each Type I subtype has a defined combination of signature genes and distinct operon organization. Type I systems additionally have a multiprotein crRNA-effector complex that is involved in the processing and interference stages of the CRISPR-Cas immune system, known as CRISPR-associated complex for antiviral defense ("Cascade"). Sub-type I-A comprises a cas5 gene which encodes a small subunit protein, a cas8 gene that encodes degraded large and small subunits, and a split cas3 gene. *Archaeoglobus fulgidus* is an exemplary organism with a sub-type I-A CRISPR-Cas system. Sub-type I-B has a set cas1-cas2-cas3-cas4-cas5-cas6-cas7-cas8 gene arrangement while lacking a cas5 gene. *Clostridium kluyveri* is an exemplary organism with a sub-type I-B CRISPR-Cas system. Sub-type I-C lacks a cash gene. *Bacillus halodurans* is an exemplary organism with a sub-type I-C CRISPR-Cas system. Sub-type I-D has a cas10d gene instead of a cas8 gene. *Cyanothece* spp. is an exemplary organism with a sub-type I-D CRISPR-Cas system. Sub-type I-E lacks a cas4 gene. *Escherichia coli* is an exemplary organism with a sub-type I-E CRISPR-Cas system. Sub-type I-F lacks a cas4 gene and has a cas2 fused to a cas3. *Yersinia pseudotuberculosis* is an exemplary organism with a sub-type I-F CRISPR-Cas system. *Geobacter sulfurreducens* is an exemplary organism with a sub-type I-U CRISPR-Cas system.

All type III CRISPR-Cas systems have a cas10 gene, which encodes a multidomain protein containing a Palm domain, which is a variant of the RNA recognition motif (RRM), that is homologous to the core domain of numerous nucleic acid polymerases and cyclases and that is the largest subunit of type III crRNA-effector complexes. Type III loci encode the small subunit protein, one Cas5 protein and typically several Cas7 proteins. Type III are further divided into four sub-types, (III-A, III-B, III-C, and III-D). Sub-type III-A has a csm2 gene encoding a small subunit and also has cas1, cas2 and cas6 genes. Staphylococcus epidermidis is an exemplary organism with a sub-type III-A CRISPR-Cas system. Sub-type III-B has a cmr5 gene encoding a small subunit, lacking cas1, cas2 and cas6 genes. *Pyrococcus furiosus* is an exemplary organism with a sub-type III-B CRISPR-Cas system. Sub-type III-C has a Cas10 protein, but with an inactive cyclase-like domain, further lacking a cas1 and cas2 gene. *Methanothermobacter thermautotrophicus* is an exemplary organism with a sub-type III-C CRISPR-Cas system. Sub-type III-D has a Cas10 protein that lacks the HD domain, further lacking a cas1 and cas2 gene, but having a cas5-like gene known as csx10. *Roseiflexus* spp. is an exemplary organism with a sub-type III-D CRISPR-Cas system.

Type IV CRISPR-Cas systems encode a minimal multi-subunit crRNA-effector complex comprising a partially degraded large subunit, Csf1, Cas5, Cas7, and in some cases, a putative small subunit. Type IV systems lack cas1 and cas2 genes. Type IV systems do not have sub-types, however there are two Type IV system variants. One Type IV variant has a DinG family helicase while the other does not, but the other has a gene encoding a small α-helical protein. *Acidithiobacillus ferrooxidans* is an exemplary organism with a Type IV CRISPR-Cas system.

Type II CRISPR-Cas systems have cas1, cas2 and cas9 genes. The cas9 gene encodes the Cas9 protein, a multidomain protein that combines the functions of the crRNA-effector complex with target DNA cleavage. Type II systems also encode a tracrRNA. Type II systems are further divided into three sub-types, sub-types II-A, II-B and II-C. Sub-type II-A comprises the additional gene, csn2. *Streptococcus thermophiles* is an exemplary organism with a sub-type II-A CRISPR-Cas system. Sub-type II-B lacks the csn2 gene, but has the cas4 gene. *Legionella pneumophilai* is an exemplary organism with a sub-type II-B CRISPR-Cas system. Sub-type II-C is the most common Type II system has only three proteins, Cas1, Cas2 and Cas9. *Neisseria lactamica* is an exemplary organism with a sub-type II-C CRISPR-Cas system Type V systems have a cpf1 gene and cas1 and cast genes. The cpf1 gene encodes a protein, Cpf1, that has a RuvC-like nuclease domain that is homologous to the respective domain of Cas9, but lacks the HNH nuclease domain that is present in Cas9 proteins. Type V systems have been identified in several bacteria, including *Parcubacteria bacterium* GWC2011_GWC2_44_17 (PbCpf1), *Lachnospiraceae bacterium* MC2017 (Lb3 Cpf1), *Butyrivibrio proteoclasticus* (BpCpf1), *Peregrinibacteria bacterium* GW2011_GWA 33_10 (PeCpf1), *Acidaminococcus* spp. BV3L6 (AsCpf1), *Porphyromonas macacae* (PmCpf1), *Lachnospiraceae bacterium* ND2006 (LbCpf1), *Porphyromonas crevioricanis* (PeCpf1), *Prevotella disiens* (PdCpf1), *Moraxella bovoculi* 237 (MbCpf1), *Smithella* spp. SC_K08D17 (SsCpf1), *Leptospira inadai* (LiCpf1), *Lachnospiraceae bacterium* MA2020 (Lb2Cpf1), *Franciscella novicida* U112 (FnCpf1), *Candidatus methanoplasma termitum* (CMtCpf1), and *Eubacterium eligens* (EeCpf1). It has also been demonstrated that Cpf1 also has RNase activity and it is responsible for pre-crRNA processing, as disclosed in Fonfara, I et al., Nature 28; 532(7600):517-21 (2016), hereby incorporated by reference in its entirety.

In Class 1 systems, the expression and interference stages involve multisubunit CRISPR RNA (crRNA)-effector complexes. In contrast, in Class 2 systems, the expression and interference stages involve a single large protein, e.g., Cas9, Cpf1, C2c1, C2c1, or C2c3, each of which is explicitly considered within the scope of this invention.

In Class 1 systems, the expression and interference stages involve multisubunit CRISPR RNA (crRNA)-effector complexes. In contrast, in Class 2 systems, the expression and interference stages involve a single large protein, e.g., Cas9, Cpf1, C2c1, C2c1, or C2c3.

In Class 1 systems, pre-crRNA is bound to the multisubunit crRNA-effector complex and processed into a mature crRNA. In Type I and III systems this involves an RNA endonuclease, for example, Cas6. In Class 2 Type II systems, pre-crRNA is bound to Cas9 and processed into a mature crRNA in a step that involves RNase III and a tracrRNA. However, in at least one described Type II CRISPR-Cas system, crRNAs with mature 5'-ends are directly transcribed from internal promoters where crRNA processing does not occur.

In Class 1 systems, the crRNA is associated with the crRNA-effector complex and achieves interference by combining nuclease activity with RNA-binding domains and base pair formation between the crRNA and a target nucleic acid.

In Type I systems, the crRNA and target binding of the crRNA-effector complex involves Cas7, Cas5, and Cas8 fused to a small subunit protein. The target nucleic acid cleavage of Type I systems involves the HD nuclease domain, which is either fused to the superfamily 2 helicase Cas3' or is encoded by a separate gene, cas3.

In Type III systems, the crRNA and target binding of the crRNA-effector complex involves Cas7, Cas5, Cas10 and a small subunit protein. The target nucleic acid cleavage of Type III systems involves the combined action of the Cas7 and Cas10 proteins, with a distinct HD nuclease domain fused to Cas10, which, while not wishing to be bound by theory, is thought to cleave single-strand DNA during interference.

In Class 2 systems, the crRNA is associated with a single protein and achieves interference by combining nuclease activity with RNA-binding domains and base pair formation between the crRNA and a target nucleic acid.

In Type II systems, the crRNA and target binding involves Cas9 as does the target nucleic acid cleavage. In Type II systems, the RuvC-like nuclease (RNase H fold) domain and the HNH (McrA-like) nuclease domain of Cas9 each cleave one of the strands of the target nucleic acid. The Cas9 cleavage activity of Type II systems also requires hybridization of crRNA to tracrRNA to form a duplex that facilitates the crRNA and target binding by the Cas9.

In Type V systems, the crRNA and target binding involves Cpf1 as does the target nucleic acid cleavage. In Type V systems, the RuvC-like nuclease domain of Cpf1 cleaves one strand of the target nucleic acid and a putative nuclease domain cleaves the other strand of the target nucleic acid in a staggered configuration, producing 5' overhangs, which is in contrast to the blunt ends generated by Cas9 cleavage. While not wishing to be bound by theory, these 5' overhangs may facilitate insertion of DNA through non-homologous end-joining methods.

As discussed herein, the Cpf1 cleavage activity of Type V systems also does not require hybridization of crRNA to tracrRNA to form a duplex, rather the crRNA of Type V systems use a single crRNA that has a stem loop structure forming an internal duplex. Cpf1 binds the crRNA in a sequence and structure specific manner, that recognizes the stem loop and sequences adjacent to the stem loop, most notably, the nucleotide 5' of the spacer sequences that hybridizes to the target nucleic acid. This stem loop structure is typically in the range of 15 to 19 nucleotides in length. Substitutions that disrupt this stem loop duplex abolish cleavage activity, whereas other substitutions that do not disrupt the stem loop duplex do not abolish cleavage activity. In Type V systems, the crRNA forms a stem loop structure at the 5' end and the sequence at the 3' end is complementary to a sequence in a target nucleic acid.

Other proteins associated with Type V crRNA and target binding and cleavage include Class 2 candidate 1 (C2c1) and Class 2 candidate 3 (C2c3). C2c1 and C2c3 proteins are similar in length to Cas9 and Cpf1 proteins, ranging from approximately 1,100 amino acids to approximately 1,500 amino acids. C2c1 and C2c3 proteins also contain RuvC-like nuclease domains and have an architecture similar to Cpf1. C2c1 proteins are similar to Cas9 proteins in requiring a crRNA and a tracrRNA for target binding and cleavage, but have an optimal cleavage temperature of 50° C. C2c1 proteins target an AT-rich PAM, which similar to Cpf1, is 5' of the target sequence. In contrast, Class 2 candidate 2 (C2c2) does not share sequence similarity to other CRISPR effector proteins, and was recently identified as a Type VI system. C2c2 proteins have two HEPN domains and demonstrate ssRNA-cleavage activity. C2c2 proteins are similar to Cpf1 proteins in requiring a crRNA for target binding and cleavage, while not requiring tracrRNA. Also like Cpf1, the crRNA for C2c2 proteins forms a stable hairpin, or stem loop structure, that aid in association with the C2c2 protein.

Specifically regarding Class 2 Type II CRISPR Cas systems, a large number of Cas9 orthologs are known in the art as well as their associated polynucleotide components (tracrRNA and crRNA) (see, e.g., Fonfara, I., et al., *Nucleic Acids Research* 42.4 (2014): 2577-2590, and Chylinski K., et al., *Nucleic Acids Research*, 2014; 42(10):6091-6105, both references hereby incorporated by reference in their entireties. Cas9-like synthetic proteins are known in the art (see, e.g., U.S. 2014/0315985 and U.S. 2016/0362667, both references hereby incorporated by reference in their entireties). Aspects of the present disclosure can be practiced by one of ordinary skill in the art following the guidance of the specification to use Type II CRISPR Cas proteins and Cas-protein encoding polynucleotides, including, but not limited to Cas9, Cas9-like, proteins encoded by Cas9 orthologs, Cas9-like synthetic proteins, and variants and modifications thereof. Cognate RNA components of these Cas proteins can be manipulated and modified for use in the practice of the present disclosure.

In CRISPR-Cas related embodiments, the target sequence comprises a gRNA sequence. The target sequence may also further comprise transactivating crRNA (tracrRNA), and may comprise other elements. Furthermore, in such CRISPR-related embodiments, the viral genome and antigenome contains a second region that includes a sequence encoding a nuclease, e.g. Cas9. The second region may or may not contain a sequence encoding a reporter molecule or any other additional sequences. As detailed supra, the second region, like the first region, may be subcloned practically anywhere in the viral genome. However, in the case of paramyxoviruses, e.g. the Sendai virus, one of ordinary skill in the art will take into consideration the relative rates of transcription. FIG. 1 represents an exemplary genome for this embodiment. In such embodiments, once the portion of the viral genome encoding the gRNA and one or more ribozymes is transcribed into mRNA containing the gRNA, the gRNA is liberated by the ribozyme(s). At least a 5' ribozyme must be present, but in preferred embodiments (though not necessarily), a flanking 3' ribozyme is present too. The type of the ribozymes utilized (hammerhead, HDV, etc.) can be according to any of the embodiments discussed herein. Once the gRNA is liberated, and after the mRNA sequence encoding the nuclease is translated, the gRNA binds to the nuclease, e.g. Cas9, through the scaffold sequence. The nuclease undergoes a conformational change once bound to the gRNA through the scaffold sequence which shifts the nuclease from an inactive conformation to an active DNA-binding conformation. Importantly, the targeting sequence of the gRNA remains exposed so that it may interact with the DNA binding site. The gRNA then directs the bound complex to the target DNA sequence, immediately upstream of the PAM, to which the nuclease will cleave. Alterations to the DNA sequence may then be introduced.

One of ordinary skill in the art will be generally familiar with how to introduce an alternation to target DNA after a double-stranded break has been introduced, however for exemplary purposes, the most common pathways utilized are the non-homologous end joining (NHEJ) DNA repair pathway and the homology directed repair (HDR) pathway. These pathways allow for introduction of alterations, most commonly insertions or deletions ("indels") but these alterations may include deletions, additions, substitutions, frameshift mutations, or point insertions. One potential advantage of the NHEJ pathway over the HDR pathway is that, unlike HDR, the NHEJ pathway is active throughout the cell cycle and has a higher capacity for repair, as there is no requirement for a repair template. Furthermore, NHEJ also repairs most types of breaks within minutes, which is significantly faster than HDR. However, HDR is the more accurate mechanisms of the two due to the requirement of higher sequence homology between the damaged and intact donor strands of DNA. HDR can be error-free if the DNA template used for repair is identical to the original DNA sequence at the location of the break. Thus, HDR can introduce very specific mutations into the damaged DNA. The HDR pathway generally follows the following steps. First, the 5'-ended DNA strand is resected at the break to create a 3' overhang. This serves as a substrate for proteins required for strand invasion and a further as a primer for DNA repair synthesis. The invasive strand then displaces a strand of the homologous DNA duplex and pair with another. This results in the formation of hybrid DNA referred to as the displacement loop (D loop). The recombination intermediates are then resolved to complete the DNA repair process. In contrast, the NHEJ pathway generally follows the following steps. First, after a double-stranded break has been introduced, the broken ends are recognized by a heterodimer, e.g. a Ku70/Ku80 heterodimer. The heterodimer will act as a scaffold for recruitment of a kinase, e.g. DNA-PKcs and a ligase, as well as some accessory factors, e.g. PAXX, XLF. This forms a paired end complex, which then ligates the compatible DNA ends together. NHEJ utilizes a number of polymerases, e.g. Polµ and Polλ, nucleases as well as structure specific enzymes, e.g. Tdp2 and Aprataxin. The processing of DNA ends is where mutations are introduced in the NHEJ pathway.

Another aspect of the present disclosure relates to vectors, aside from the viral particles of the present disclosure that comprise the nucleic acids of the present disclosure. The vectors may be DNA or RNA vectors. In an exemplary embodiment, the vectors comprise plasmids that contain DNA encoding both the genome and the antigenome. The plasmids may be induced to generate the viral particles. The vector may include appropriate sequences for amplifying expression. In addition, the expression vector preferably contains one or more selectable marker genes to provide a phenotypic trait for selection of transformed host cells such as dihydrofolate reductase or neomycin resistance for eukaryotic cell cultures, or such as tetracycline or ampicillin resistance in *E. coli*.

Some embodiments of the present disclosure are directed to cells transformed with the plasmids. Any of the procedures known in the art for introducing foreign nucleotide sequences into host cells may be used. Examples include the use of calcium phosphate transfection, polybrene, protoplast fusion, electroporation, nucleofection, liposomes, microinjection, naked DNA, plasmid vectors, viral vectors, both episomal and integrative, and any of the other well-known methods for introducing cloned genomic DNA, cDNA, synthetic DNA or other foreign genetic material into a host cell.

Another aspect of the present disclosure relates to kits comprising the vectors of the present disclosure. The kits may further include reagents. In an exemplary embodiment, the reagents include T7 RNA polymerase. The kits may contain controls. The kits may contain instructions or directions for use. The kit may be comprised of one or more containers and may also include collection equipment, for example, bottles, bags (such as intravenous fluids bags), vials, syringes, and test tubes. Other components may include needles, diluents and buffers. Usefully, the kit may include at least one container comprising a pharmaceutically-acceptable buffer, such as phosphate-buffered saline, Ringer's solution and dextrose solution. Optionally, the kits of the disclosure further include software to expedite the generation, analysis and/or storage of data, and to facilitate access to databases. The software includes logical instructions, instructions sets, or suitable computer programs that can be used in the collection, storage and/or analysis of the data. Comparative and relational analysis of the data is possible using the software provided.

The terms "conservative sequence modifications" or "conservative substitutions" as used herein may refer to nucleotide substitutions that do not significantly affect or alter the activity or characteristics of the self-cleaving ribozymes of the present disclosure.

The term "CRISPR" as used herein may refer to "clustered regularly interspaced short palindromic repeat", which in the scope of the present disclosure is understood to be utilized in conjunction with a nuclease such as Cas9 to edit a target DNA sequence, e.g. CRISPR/Cas9 system. The term "Cas" as used herein may refer to "CRISPR associated protein", and includes but is not limited to the nuclease Cas9 and Cas9 proteins. "Cas9" or "Cas9 protein" as used herein includes Cas9 wild-type protein derived from CRISPR-Cas9 systems, modifications of Cas9 proteins, analogs of Cas9 proteins, variants of Cas9 proteins, proteins expressed by cas9 orthologs, and combinations thereof. Other "Cas" proteins are known in the art and are considered to be within the scope of this disclosure, including Cas9-like synthetic proteins, Cpf1 proteins (including wild-type Cpf1), Cpf1-like synthetic proteins, C2c1 proteins, C2c2 proteins, C2c3 proteins, and variants and modifications thereof "Cpf1" or "Cpf1 proteins" as used herein includes Cpf1 wild-type protein derived from CRISPR-Cpf1 systems, modifications of Cpf1 proteins, variants of Cpf1 proteins, Cpf1 analogs, proteins expressed by cpf1 orthologs, and combinations thereof.

As used herein, the term "guide RNA" or "gRNA" may refer to an RNA molecule that can bind to a nuclease and guide the nuclease to a specific location within a target DNA. A guide RNA can comprise two segments: a "targeting sequence" and a "scaffold sequence". "Targeting sequence" as used herein may refer to a nucleotide sequence that is complementary to, or at least can hybridize to under stringent conditions, a target DNA sequence. The protein-binding segment binds to nuclease, e.g. Cas9, Cpf1, or a related CRISPR associated protein ("Cas") disclosed herein. The targeting sequence and the scaffold sequence can be located in the same RNA molecule or in two or more separate RNA molecules.

The term "heterologous" as used herein may refer to biological elements that are from different sources, e.g. foreign DNA or RNA introduced into an organism. For example, in the present disclosure, a nuclease may be from a first source, e.g. Cas9 from S. pyogenes bacterium. Or, a target sequence, e.g., gRNA may be from a second organism or may be synthetic. One of ordinary skill in the art will appreciate that introduction of foreign genetic material into an organism, e.g. introduction of an expression cassette, may introduce many heterologous elements to the organism.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods.

As used herein, the term "expression" refers to transcription of a polynucleotide from a DNA template, resulting in, for example, an mRNA or other RNA transcript (e.g., non-coding, such as structural or scaffolding RNAs). The term further refers to the process through which transcribed mRNA is translated into peptides, polypeptides, or proteins. Transcripts and encoded polypeptides may be referred to collectively as "gene products." Expression may include splicing the mRNA in a eukaryotic cell, if the polynucleotide is derived from genomic DNA.

The terms "polynucleotide", "nucleotide sequence" or "nucleic acid" as used herein may refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA. Examples of a nucleic acid include and are not limited to mRNA, miRNA, tRNA, rRNA, snRNA, siRNA, dsRNA, cDNA and DNA/RNA hybrids. Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil (U), adenine (A), thymine (T), cytosine (C), guanine (G), and their derivative compounds. Nucleic acids may be obtained by chemical synthesis methods or by recombinant methods. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof.

The term "ribozyme" as used herein refers to RNA molecules that are capable of catalyzing specific biochemical reactions. The activity of a ribozyme is similar to that of a protein enzyme, the chief difference being the composition of the two. The term "self-cleaving ribozyme" as used herein refers to a RNA molecule motif that catalyzes cleavage and related reactions at a specific site within an RNA polymer. Examples of self-cleaving ribozymes include but are not limited to hammerhead ribozymes, hepatitis delta virus (HDV) ribozymes, twister ribozymes, twister sister ribozymes, pistol ribozymes, hairpin ribozymes, and hatchet ribozymes.

The term "treating" or "treatment" of a disease refers to executing a protocol, which may include administering one or more drugs to a patient (human or otherwise), in an effort to alleviate signs or symptoms of the disease. Alleviation can occur prior to signs or symptoms of the disease appearing as well as after their appearance. Thus, "treating" or "treatment" includes "preventing" or "prevention" of disease. The terms "prevent" or "preventing" refer to prophylactic and/or preventative measures, wherein the object is to prevent or slow down the targeted pathologic condition or disorder. In addition, "treating" or "treatment" does not require complete alleviation of signs or symptoms, does not require a cure, and specifically includes protocols that have only a marginal effect on the patient.

As used herein, a "host cell" generally refers to a biological cell. A cell can be the basic structural, functional and/or biological unit of a living organism. A cell can originate from any organism having one or more cells. Examples of host cells include, but are not limited to: a prokaryotic cell, a eukaryotic cell, a bacterial cell, an archaeal cell, a cell of a single-cell eukaryotic organism, a protozoa cell, a cell from a plant, an algal cell, a fungal cell (e.g., a yeast cell), an animal cell, a cell from an invertebrate animal, a cell from a vertebrate animal (e.g., fish, amphibian, reptile, bird, mammal), a cell from a mammal (e.g., a pig, a cow, a goat, a sheep, a rodent, a rat, a mouse, a non-human primate, a human, etc.). A host cell can be a stem cell or progenitor cell.

The term "patient" as used herein may refer to a biological system to which a treatment can be administered. A biological system can include, for example, an individual cell, a set of cells (e.g., a cell culture), an organ, a tissue, or a multi-cellular organism. A "patient" can refer to a human patient or a non-human patient.

The term "protospacer adjacent motif" or "PAM" as used herein refers to the DNA sequence immediately following the target DNA sequence that is targeted by the nuclease in a CRISPR application setting. The PAM is nuclease specific, and the nuclease will not successfully bind to or cleave the target DNA sequence if it is not followed by the PAM. The term "vector" as used herein may refer to a nucleic acid sequence containing an origin of replication. A vector may be a plasmid, bacteriophage, bacterial artificial chromosome, yeast artificial chromosome or a virus. A vector may be a DNA or RNA vector. A vector may be either a self-replicating extrachromosomal vector or a vector which integrates into a host genome. The term "expression vector" refers to a nucleic acid assembly containing a promoter which is capable of directing the expression of a sequence or gene of interest in a cell. Vectors typically contain nucleic acid sequences encoding selectable markers for selection of cells that have been transfected by the vector. Generally, "vector construct," "expression vector," and "gene transfer vector," refer to any nucleic acid construct capable of directing the expression of a gene of interest and which can transfer gene sequences to target cells or host cells.

As used herein and in the appended claims, the singular forms "a", "and" and "the" include plural references unless the context clearly dictates otherwise.

The term "about" refers to a range of values which would not be considered by a person of ordinary skill in the art as substantially different from the baseline values. For example, the term "about" may refer to a value that is within 20%, 15%, 10%, 9%, 8%, 7%, 6%, 5%, 4%, 3%, 2%, 1%, 0.5%, 0.1%, 0.05%, or 0.01% of the stated value, as well as values intervening such stated values.

Publications disclosed herein are provided solely for their disclosure prior to the filing date of the present disclosure.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The following non-limiting examples serve to further illustrate the present disclosure.

EXAMPLES

Example 1

Sendai Virus Delivers CRISPR/Cas9 for Gene Editing

A. Materials and Methods

Cell Lines

Flp-In T-REx HEK293 cells (Invitrogen), Vero cells (ATCC CCL-81), BSR-T7 cells (BHK-based cell line with stable expression of T7 polymerase), and Affinofile cells (HEK293-based cell line with inducible overexpression of CD4 and CCR5) were propagated in Dulbecco's modified Eagle's medium (Invitrogen) supplemented with 10% fetal bovine serum (FBS) (Atlanta Biologicals) and penicillin/streptomycin at 37° C. Flp-In T-REx HEK293 cells were additionally maintained in blasticidin and zeocin according to manufacturer protocol, BSR-T7 cells were additionally maintained in 1 mg/mL G418 to maintain the T7 transgene, and Affinofile cells were additionally maintained in 50 µg/mL blasticidin. To generate the mCherry-inducible cells, the mCherry gene was inserted into pcDNA5/FRT/TO and co-transfected with pOG44 (Flp-recombinase) into parental Flp-In T-REx HEK293 cells. Selection with hygromycin (replacing zeocin) and blasticidin according to manufacturer protocol yielded a stable cell line with doxycycline-inducible expression of mCherry.

Whole human blood was obtained from the New York Blood Center. Peripheral blood mononuclear cells were isolated using Ficoll-Paque (GE Healthcare), and monocytes were further purified using CD14 MicroBeads (Miltenyi Biotec). Monocytes were propagated in RPMI 1640 medium (Invitrogen) supplemented with 10% FBS (Atlanta Biologicals).

Sendai Virus Reverse Genetics Plasmids

The basis for rSeV-Cas9 was a recombinant Sendai virus with an EGFP reporter inserted between the N and P genes via duplication of the N-to-P intergenic region, derived from RGV0, a Fushimi strain SeV with mutations in the F and M genes that allow trypsin-independent growth. All modifications to the plasmid encoding the T7-driven antigenome were performed using standard and overlapping PCRs with Velocity DNA polymerase (Bioline), with subsequent insertion into the construct at unique restriction sites by In-Fusion ligation-independent cloning (Clontech). All cloning was performed with Stbl2 E. coli (Invitrogen) with growth at 30° C. FLAG-tagged codon-optimized S. pyogenes Cas9 was amplified from px330 (Addgene, cat #42230) and inserted into rSeV following the EGFP reporter, linked with a P2A ribosomal skipping sequence (ATNFSLLKQAGDVEENPGP) (SEQ ID NO: 4). The P2A sequence was preceded by a GSG linker to ensure complete ribosomal skipping. An additional two nucleotides were added after the stop codon of Cas9 to maintain the rule of six, by which the genome length of paramyxoviruses must be an exact multiple of six to ensure efficient replication. The Cas9 is flanked by unique NotI and FseI restriction sites to aid in any future modifications. To create the guide RNA and ribozyme cassette, the mCherry-targeting 20 bp sequence was cloned into px330 (discussed supra), and the full chimeric guide RNA cassette (SEQ ID NO: 1, see Table 1 below) was then PCR-amplified. The hammerhead ribozymes were incorporated via overhangs in the synthesized primers in subsequent PCRs. This cassette was inserted between the P and M genes via duplication of the P-to-M intergenic region, with unique AsiSI and SnaBI restriction sites flanking the cassette to aid in future modifications including changing the guide RNA target sequence. The guide RNA target sequences were chosen based on high predicted specificity using a CRISPR design tool available online through MIT.

```
(SEQ ID NO: 1, Guide RNA Cassette)
ATCCCGGGTGAGGCATCCCACCATCCTCAGTCACAGAGAGACCC

AATCTACCATCAGCATCAGCCAGTAAAGATTAAGAAAAACTTAG

GGTGAAAGAAATTTCACCTAACACGGCGCAGCGATCGCGTGGCC

CTGATGAGTCCGTGAGGACGAAACGGTAGGAATTCCTACCGTCG

GCCACGAGTTCGAGATCGAGTTTTAGAGCTAGAAATAGCAAGTT

AAAATAAGGCTAGTCCGTTATCAACTTGAAAAAGTGGCACCCAC

TCGGTGCACGTATCACCGGAGTCGACTCCGGTCTGATGAGTCCG

TGAGGACGAAATACGTATCCCGGGTGAGGCATCCCACCATCCTC

AGTCACAGAGAGACCCAATCTACCATCAGCATCAGCCAGTAAAG

ATTAAGAAAAACTTAGGGTGAAAGAAATTTCACCTAACACGGCGCA
```

TABLE 1

Annotated sequence of gRNA Cassette.

| Nucleotide Positions Within Guide RNA Cassette (SEQ ID NO: 1) | Description |
| --- | --- |
| 1-118, 325-442 | P-to-M intergenic region; guide RNA cassette inserted via duplication of this region in this instance |
| 73-83, 397-407 | Gene stop signal |
| 84-86, 408-410 | Intergenic trinucleotide |
| 87-96, 411-420 | Gene start signal |
| 119-126 | Restriction site, e.g. modified AsiSI restriction site in this instance |
| 127-132, 176-181 | Stem for 5' ribozyme (e.g. rbz 1). Note: 1$^{st}$ part of stem, e.g. GTGGCC in this instance, must be the reverse complement of the beginning of the gRNA targeting sequence. See, e.g., FIG. 1B for stem structure. |
| 133-175 | 5' ribozyme (e.g. rbz 1) |
| 176-195 | Guide RNA (gRNA), e.g. mCherry-targeting sequence in this instance |
| 196-271 | TracrRNA |
| 272-277, 319-324 | Stem for 3' ribozyme (e.g. rbz 2) |
| 278-318 | 3' ribozyme (e.g. rbz 2) |
| 320-325 | Restriction site, e.g. modified SnaBI restriction site in this instance |
| 135 | Mutated to C to abolish 5' ribozyme activity |
| 299 | Mutated to C to abolish 3' ribozyme activity |

Figure 7:
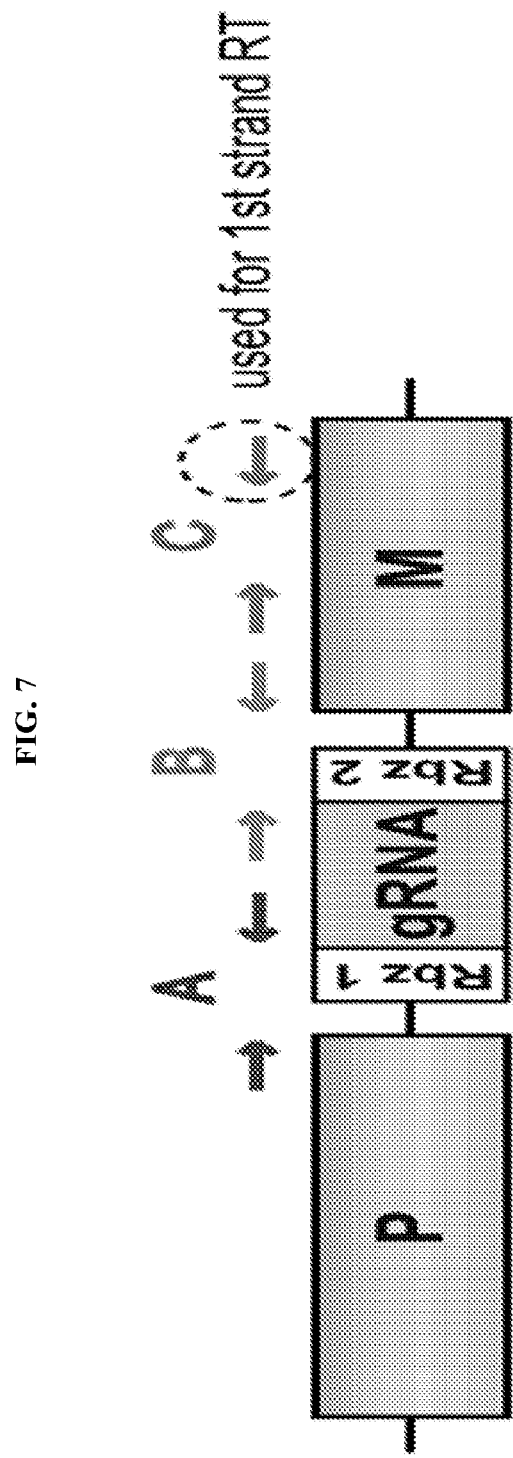
FIG. 7 represents a diagram of qRT-PCR primers used for ribozyme cleavage assay.

Cleavage Assay qRT-PCR primers were designed to flank ribozyme 1 (product A), ribozyme 2 (product B), and within the downstream M gene (product C, representing total RNA) (see FIG. 7). rSeV-Cas9-mCherry T7-driven antigenome plasmid was transfected into T7-expressing BSR-T7 cells for 2 hours before collection in TRIzol (Invitrogen). Samples were treated with DNase (Invitrogen) at 1 mM $MgCl_2$, treated with EDTA, and reverse-transcribed at 1 mM $MgCl_2$ with the SuperScript III First-Strand Synthesis System (Invitrogen). qRT-PCR was performed with the SensiFAST SYBR & Fluorescein kit (Bioline), with copy numbers determined by standard curves using the rSeV-Cas9-mCherry antigenome plasmid as template. Percent ribozyme 1 cleavage was determined as 100*((C−A)/C) and normalized to the construct with both ribozymes mutated, and percent ribozyme 2 cleavage was determined as 100*((C−B)/C) and normalized to the construct with ribozyme 2 mutated.

Viruses and Infections

BSR-T7 cells in 6-well were transfected with 4 ug T7-driven antigenome, 1.44 µg T7-N, 0.77 µg T7-P, 0.07 µg T7-L, and 4 µg codon-optimized T7 polymerase, using Lipofectamine LTX (Invitrogen) according to manufacturer's recommendations. Virus rescue was monitored by appearance and spread of EGFP fluorescence, and rescued virus was further expanded on BSR-T7 cells. Stocks of clarified virus were stored at −80° C. Virus titers were determined by titration on Vero cells, with individual infection events detected and counted by EGFP fluorescence at 24 hours post-infection in an Acumen plate reader (TTP Labtech).

For SeV infection of HEK293-based cell lines, $5 \times 10^4$ cells were mixed with the virus inoculum immediately prior to plating in poly-L-lysine-coated wells. Media was changed the following day and every 2 days thereafter. For induction of mCherry, 100 ng/mL doxycycline was used. For Affinofile cells, 2 µg/mL ponasterone A and 8 ng/mL doxycycline were used to induce CCR5 and CD4, respectively. For further HIV-1 infection of Affinofile cells, JR-FL HIV-1 was spinoculated onto cells at 2000 rpm for 2 hours at 37° C. in the presence of 2 µg/mL polybrene (Sigma).

For SeV infection of monocytes, virus stocks were further purified by ultracentrifugation into a discontinuous 20% to 65% sucrose gradient. The interface was collected, titered on Vero cells, and stored at −80° C. until use. $5 \times 10^5$ cells in serum-free medium were plated for 30 minutes at 37° C. to allow adherence before infection with virus inoculum via spinoculation at 2000 rpm for 2 hours at 37° C. Media was changed to RPMI with 10% FBS following spinoculation and changed every 2 days thereafter. 100 ng/mL GM-CSF (Peprotech) was included in the media following infection to stimulate macrophage differentiation and concomitant upregulation of CCR5.

Flow Cytometry

For CCR5 staining, cells were lifted and blocked in phosphate-buffered saline (PBS) with 2% FBS. Alexa 647-conjugated rat anti-human CCR5 (BioLegend, cat #313712) was added at 1:100 for 30 minutes at 4° C. before washing and resuspension in 2% paraformaldehyde (PFA). For p24 staining (RD1-conjugated mouse anti-p24 clone KC57, Beckman Coulter, cat #6604667, 1:100 dilution), cells were fixed and permeabilized using the Cytofix/Cytoperm kit (BD Biosciences) before blocking. Flow cytometry was performed on a BD LSR II at the Flow Cytometry Core at the Icahn School of Medicine at Mount Sinai.

Characterization of Mutagenesis

Genomic DNA was extracted using the PureLink Genomic DNA Mini Kit (Invitrogen). Specific genomic loci were amplified using Velocity DNA Polymerase (Bioline) and primers as shown in Table 2 below. Off-target loci represent the top predicted off-target sites in the CRISPR Design Tool. For Sanger sequencing of individual alleles, primers contained appropriate overhangs for insertion between the HindIII and XhoI sites of pcDNA3 via In-Fusion ligation-independent cloning (Clontech). PCR products were gel-extracted (NucleoSpin Gel and PCR Clean-up kit, Clontech), transformed into Stellar competent *E. coli* (Clontech), and selected on ampicillin LB agar. Individual colonies were prepped and sequenced. For deep sequencing, the gel-extracted products were pooled and further prepared for sequencing via paired-end 2×300 bp MiSeq (Illumina) sequencing by Genewiz, Inc. Unique sequences were identified and quantified from merged sequenced reads. For each on-target and off-target amplicon reference sequence, 18 bp sequences were selected just beyond 35 bp upstream and downstream from the 20 bp guide RNA target sequence. Unique sequences with exact matches to both of these 18 bp sequences were extracted and collated, with an average of 170,432 reads per amplicon. For each amplicon, sequences with lengths divergent from the reference sequence were identified as having insertions or deletions (indels).

TABLE 2

On-target and off-target genomic locations, sequences, and amplification primers utilized.

| Sequence | Genomic Location | Target + PAM (underlined) | Primer Sequences |
| --- | --- | --- | --- |
| mCherry | n/a | GGCCACGAGTTCGAGATCGAGGG (SEQ ID NO: 5) | Forward: GGCGAGGAGGATAACATGG (SEQ ID NO: 18) Reverse: CTTCAGCCTCTGCTTGATCTC (SEQ ID NO: 19) |
| ccr5 on-target | chr3, +1 46373721 | CAGGTTGGACCAAGCTATGCAGG (SEQ ID NO: 6) | Forward: TTGTCATGGTCATCTGCTACTC (SEQ ID NO: 20) Reverse: GTGTCACAAGCCCACAGATATT (SEQ ID NO: 21) |
| ccr5 off #1 | chr1, -1 179505884 | CAGACTGGATCAAGCTATGCCAG (SEQ ID NO: 7) | Forward: CTCCACTTTCCATAACAGTCTAGG (SEQ ID NO: 22) Reverse: GGTCCTTGGAACAGTAGAGATAG (SEQ ID NO: 23) |
| ccr5 off #2 | chr3, -1 32755718 | CAAGTTACAACAAGCTATGCAAG (SEQ ID NO: 8) | Forward: TGTTTGCTGTGAGGCTACTTTG (SEQ ID NO: 24) Reverse: TCACTGTCCAATCTGCTTTACC (SEQ ID NO: 25) |
| ccr5 off #3 | chr20, -1 17216675 | AAGGTTTTTCCAAGCTATGCTAG (SEQ ID NO: 9) | Forward: GCAGAGGCATTATAAACCCAATATG (SEQ ID NO: 26) Reverse: CCAGGAGGAACTGGCAAAT (SEQ ID NO: 27) |
| ccr5 off #4 | chr2, +1 140172166 | CAGGATTCACCAAGCTCTGCCAG (SEQ ID NO: 10) | Forward: AAGCTCCATCTTCTTCGTTCTT (SEQ ID NO: 28) Reverse: AGTAGGAGATGGATTTACAGGTATT (SEQ ID NO: 29) |
| ccr5 off #5 | chr12, +1 59746621 | CAGTTTGGTTCAAGCTATGTTAG (SEQ ID NO: 11) | Forward: CAGTGACATGAGCACCTGAA (SEQ ID NO: 30) Reverse: GCAAGGACATCCTCATCCATAA (SEQ ID NO: 31) |
| efnb2 on-target | chr13, -1 106512590 | AGAATTCAGCCCTAACCTCTGGG (SEQ ID NO: 12) | Forward: CCTGGACAAGGACTGGTACTAT (SEQ ID NO: 32) Reverse: TAGCACAGGGTCCCAAATTC (SEQ ID NO: 33) |

TABLE 2-continued

On-target and off-target genomic locations, sequences, and amplification primers utilized.

| Sequence | Genomic Location | Target + PAM (underlined) | Primer Sequences |
|---|---|---|---|
| efnb2 off #1 | chr7, -1 136299453 | AGAATTCAGGCTTAACCTCT<u>TAG</u> (SEQ ID NO: 13) | Forward: GCAGGCTGGTAATTGATCTTTC (SEQ ID NO: 34) Reverse: TGATCCACAGTTGGTTGAATCC (SEQ ID NO: 35) |
| efnb2 off #2 | chr2, +1 36596395 | AAAATTCTTCCCTAACCTCT<u>AAG</u> (SEQ ID NO: 14) | Forward: CCAGAATGTGTCCTGGGTTTAG (SEQ ID NO: 36) Reverse: GTGTCAGAGCGAGACTTTGT (SEQ ID NO: 37) |
| efnb2 off #3 | chr7, +1 98992870 | ACATTTCAGCTCTAACCTCT<u>GGG</u> (SEQ ID NO: 15) | Forward: GGAGTATCTTCAGCTGTGAGAAG (SEQ ID NO: 38) Reverse: CTGTTACACGTTCCTTGCTACT (SEQ ID NO: 39) |
| efnb2 off #4 | chr14, +1 98564083 | ATAAATCAGCCCTAACATCT<u>GAG</u> (SEQ ID NO: 16) | Forward: CTGATTGAGTGGGTCATCAGAA (SEQ ID NO: 40) Reverse: GCTACGTGCTGGTGCTAAA (SEQ ID NO: 41) |
| efnb2 off #5 | chr3, -1 6909191 | AAAAGTTTGCCCTAACCTCT<u>CAG</u> (SEQ ID NO: 17) | Forward: GTCCAGGAAAGAAAGTTGCATAAG (SEQ ID NO: 42) Reverse: GCTGTCTGCTGGAAAGATAGT (SEQ ID NO: 43) |

B. Results

Sendai Virus Incorporating Cas9 and a Guide RNA Flanked by Self-Cleaving Ribozymes Replicates to High Titer Paramyxoviruses have a single-stranded, negative-sense RNA genome. During replication, the virus replication complex (nucleoprotein (N), phosphoprotein (P), and large RNA-dependent RNA polymerase (L)) uses the genome as a template for production of both full length antigenome (the reverse complement of the genome) and individual capped and polyadenylated mRNAs (FIG. 1A). The antigenome is further transcribed into genome, thus amplifying the genome for replication. During mRNA production, gene start and gene stop signals within the flanking intergenic regions determine the ends of the mRNA transcript. For this proof-of-principle study, a recombinant SeV (rSeV) with EGFP inserted between the N and P genes via duplication of the N-to-P intergenic region was utilized. S. pyogenes Cas9 was inserted downstream of the EGFP reporter via a P2A ribosomal skipping sequence (FIG. 1A). A chimeric guide RNA (20 bp target sequence and 76 bp trans-activating CRISPR RNA) was inserted as a new cassette between the P and M genes via duplication of the P-to-M intergenic region (FIG. 1A). The guide RNA was flanked by a self-cleaving 5' ribozyme and a self-cleaving 3' ribozyme, e.g. hammerhead ribozymes, to provide precise ends to the guide RNA (FIGS. 1A and 1B). The sequence of the exemplary self-cleaving 5' ribozyme and the self-cleaving 3' ribozyme, are shown in FIG. 1B in their conformational orientation, and in 5' to 3' as follows:

Rbz1:
(SEQ ID NO: 2)
GUGGCCCUGAUGAGCGAAACGGUAGGAAUUCCUACCGUC

Rbz2:
(SEQ ID NO: 3)
CACCGGAGUCGACUCCGGUCUGAUGAGUCCGUGAGGACGAAAUACGU

Figure 5:
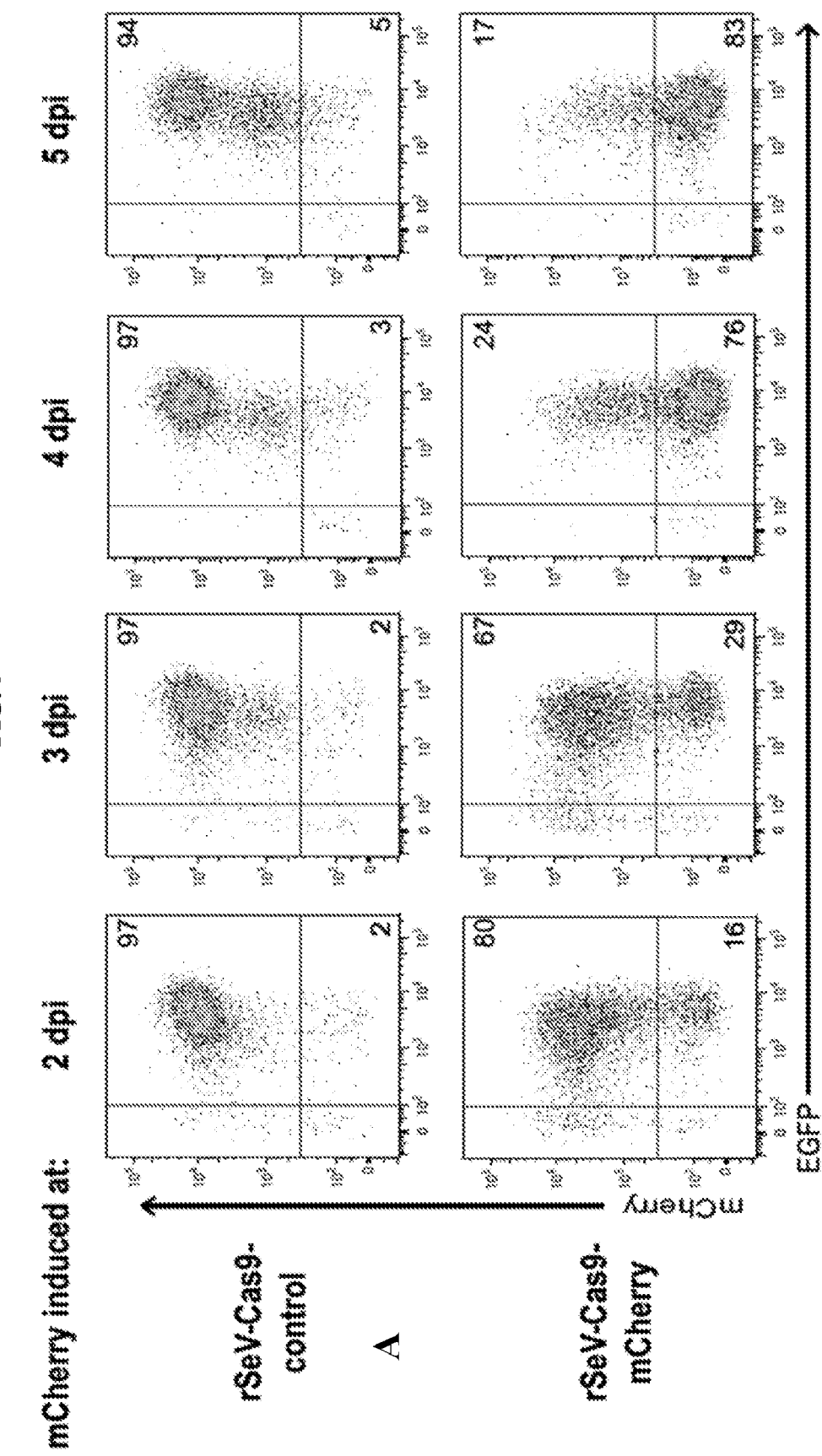
FIG. 5 represents a time course of mCherry fluorescence knockout by rSeV-Cas9-mCherry.
Figure 5:
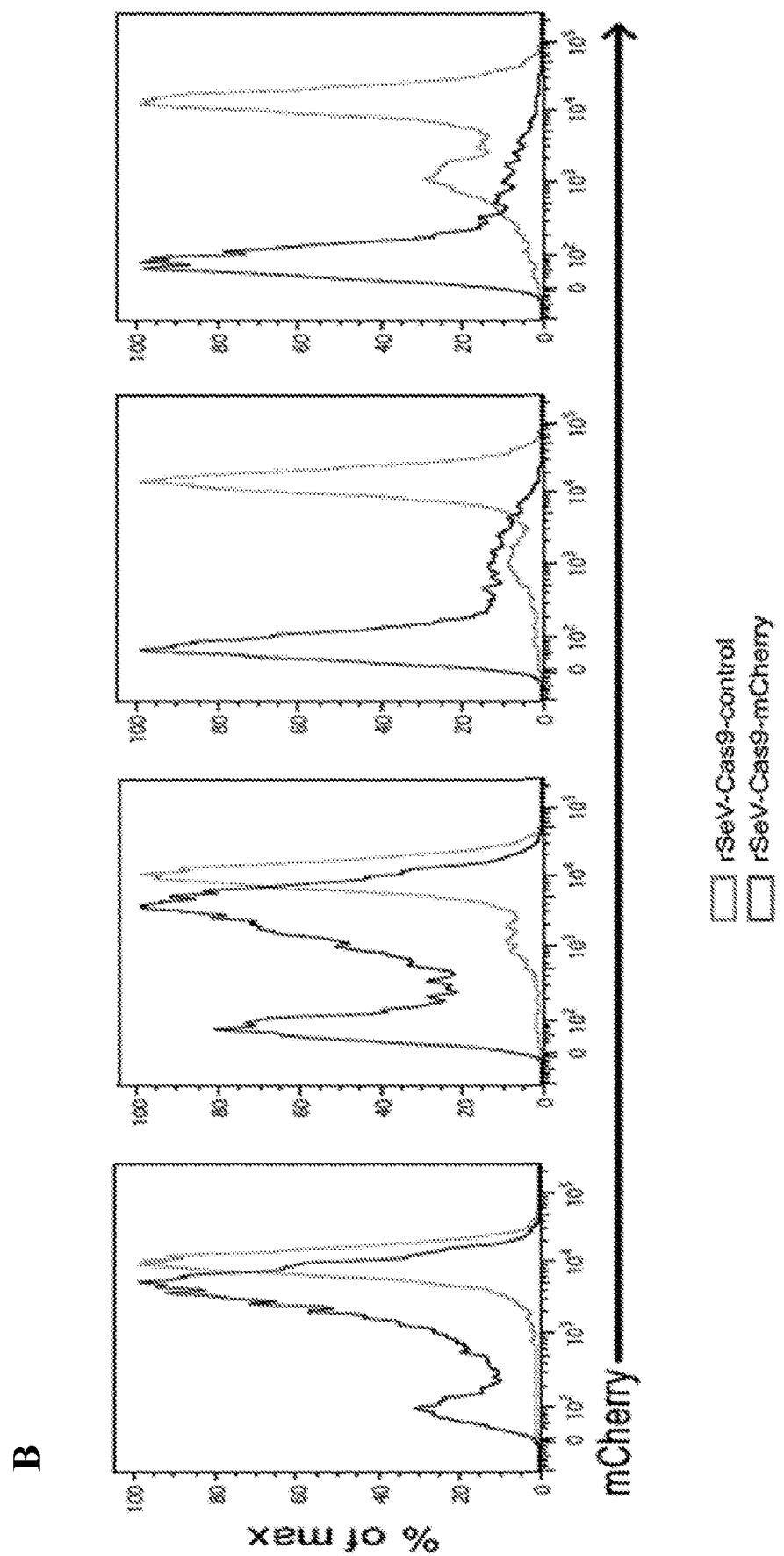

The ribozymes were confirmed as functional for cleavage by transfecting the DNA construct encoding the T7-driven rSeV-Cas9 positive-sense antigenome (the ribozymes are functional in the RNA positive-sense orientation) into BSR-T7 cells (BHK cells stably expressing T7 polymerase). qRT-PCR on T7-transcribed antigenomic RNA extracted from transfected cells showed efficient self-cleavage for both ribozymes (FIG. 1C). Replication-competent rSeV-Cas9 were rescued by co-transfecting the antigenome construct with the accessory SeV-N, -P, and -L expression constructs required for genomic replication and thus virus rescue. Tescue efficiency and/or genomic replication was hypothesize as potentially being impaired or even blocked by the presence of self-cleaving ribozymes in the antigenome. However, it was also hypothesized that nucleoprotein encapsidation of the antigenomic RNA would happen quickly enough to prevent formation of the ribozyme structure and thus self-cleavage of the antigenome; by contrast, mRNAs are not encapsidated, and thus the mRNA encoding the guide RNA would be free to undergo ribozyme cleavage. Unexpectedly and surprisingly, rSeV-Cas9 rescued as efficiently as a corresponding control virus with mutations in the ribozymes to prevent ribozyme activity (FIG. 1D). Although the growth kinetics of rSeV-Cas9 were slower than those of the control virus, consistent with some negative effect of the ribozymes on genomic replication, rSeV-Cas9 still reached the same peak titer of almost $10^8$ IU/mL (FIG. 1E), consistent with standard peak titers for SeV in cell culture. It was further confirmed that rSeV-Cas9 produced the Cas9 protein upon infection. Western blot analysis of HEK293 cells either transfected with a Cas9-expressing plasmid or infected with rSeV-Cas9 showed the expression of Cas9 protein (FIG. 1F).

rSeV-Cas9 Targeting mCherry Gene Achieves Almost Complete Mutagenesis of a Reporter Cell Line The initial rSeV-Cas9 incorporated a guide RNA specific for the mCherry gene (rSeV-Cas9-mCherry). A HEK293-based reporter cell line was generated with inducible mCherry, and this cell line was infected at a multiplicity of infection (MOI) of 25 with either rSeV-Cas9-mCherry or a control virus expressing Cas9 but lacking the guide RNA cassette (rSeV-Cas9-control). Induction of mCherry expression at various days post-infection showed a progression of knockout over time, with knockout appearing more pronounced starting at 4 days post-infection (FIG. 2A and FIG. 5). Quantification of this time point (induction at day 4 and collection for flow cytometry at day 5) showed ~80% knockout of mCherry fluorescence (FIG. 2A). Fluorescence microscopy visually confirmed the strong reduction of mCherry fluorescence upon knockout (FIG. 2B).

The reporter cell line was utilized to confirm the requirement for the ribozymes to preserve guide RNA function. Mutation of the 3' ribozyme (rbz 2) strongly reduced reporter knockout efficiency, while mutation of both the 5' and 3' ribozymes (rbz 1/2) abrogated knockout activity (FIG. 2C, compare to FIG. 2A). An alternative 3' ribozyme was tested, the widely-used hepatitis delta virus ribozyme, in place of the existing hammerhead ribozyme. This version of rSeV-Cas9-mCherry also efficiently knocked out mCherry fluorescence, surprisingly with potentially even greater efficiency (FIG. 2C).

To quantitatively assess the degree of mutagenesis induced by rSeV-Cas9-mCherry, deep sequencing was performed on the mCherry locus amplified from reporter cells collected at day 6 post-infection. 98% of alleles had indels, indicating nearly complete mutagenesis of the reporter (FIG. 2D). These results strongly indicated that the rSeV-Cas9 vector is highly efficient in targeting endogenous alleles.

rSeV-Cas9 Efficiently Mutates Endogenous ccr5 and efnb2

Figure 3:
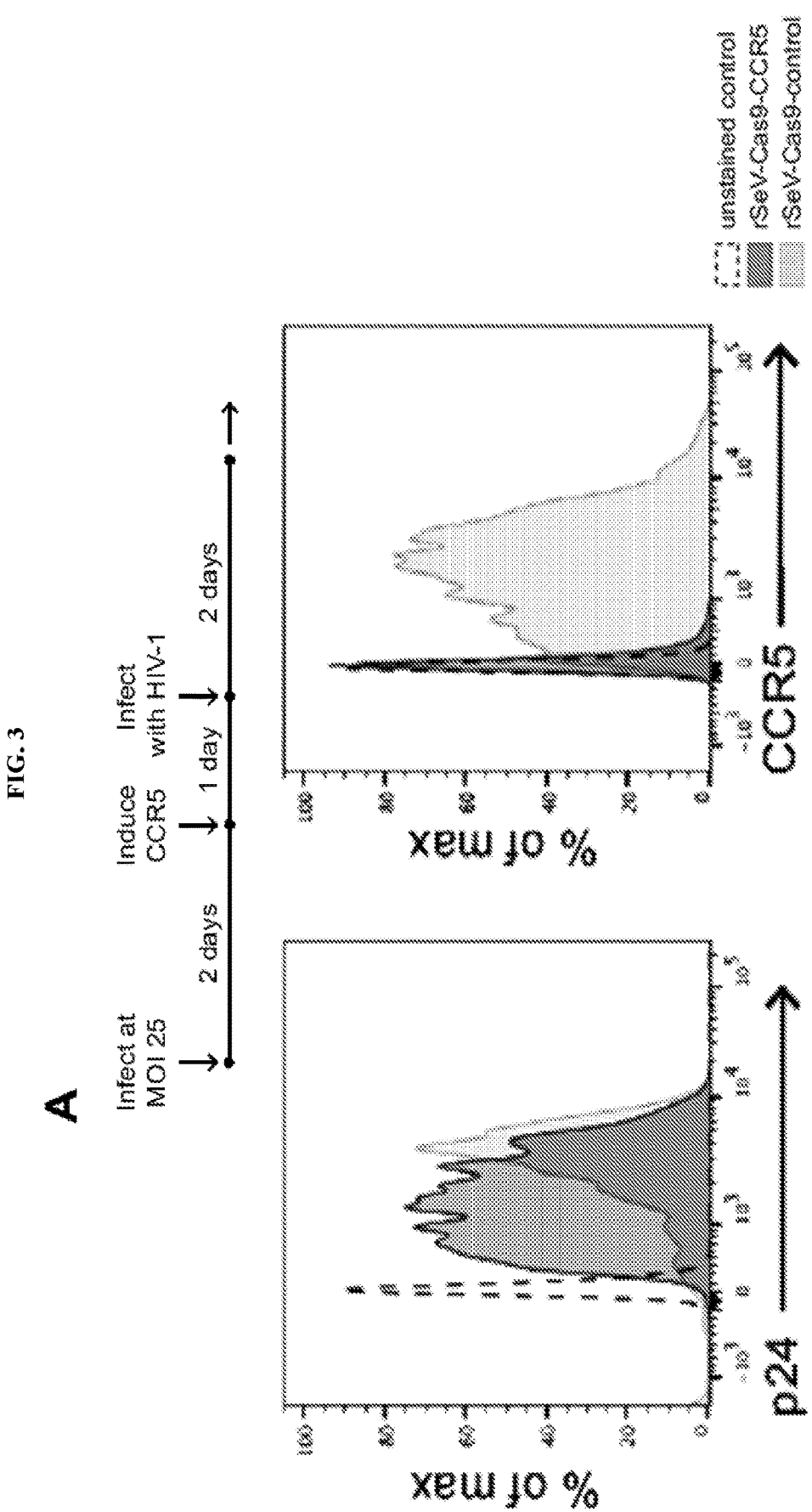
FIG. 3 represents rSeV-Cas9 efficiently mutates endogenous ccr5 and efnb2.
Figure 3:
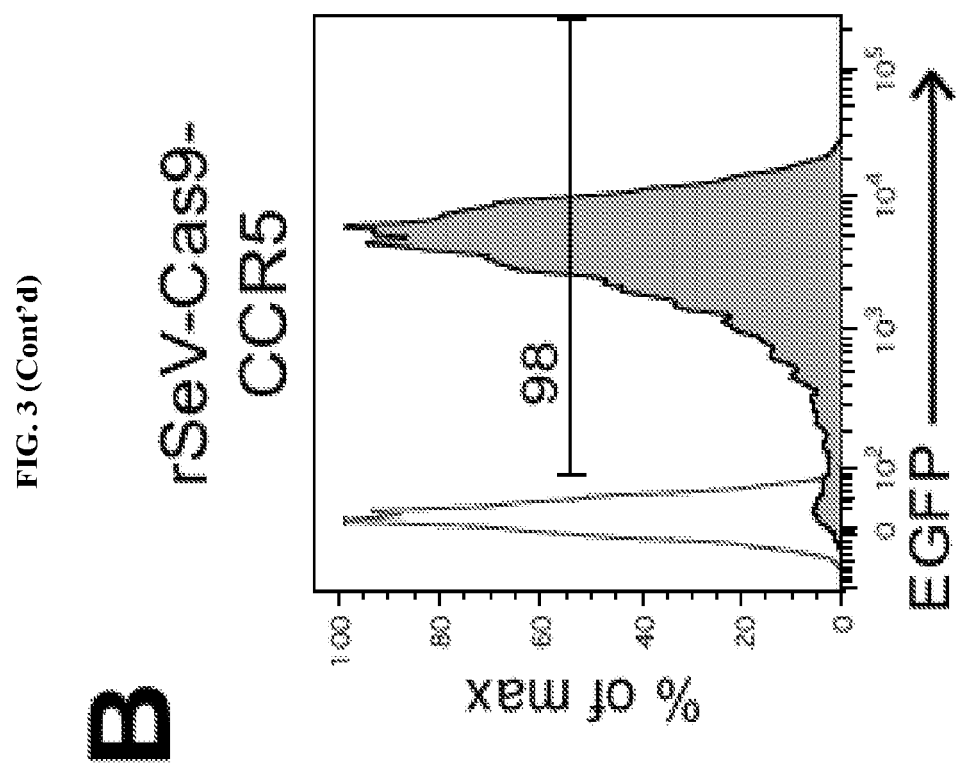

As opposed to the single allele of mCherry in the reporter cell line, there are two or more alleles of most endogenous genes per cell. To test the ability of the Sendai virus vector to target the more abundant endogenous alleles, rSeV-Cas9 viruses were generated targeting coding exons of the human ccr5 and efnb2 genes. A preliminary test of the ability of rSeV-Cas9-CCR5 was performed to induce mutagenesis resulting in functional disruption of ccr5. HEK293 cells were utilized since HEK293 cells express negligble levels of CCR5, which contain inducible CD4 and CCR5 transgenes in addition to their endogenous alleles. CD4 and CCR5 are cell surface receptors required for infection by R5-tropic HIV-1, and Affinofile cells have been used extensively to characterize CCR5-mediated HIV entry. Affinofile cells were infected with rSeV-Cas9-CCR5, and at 2 days post-infection, CD4/CCR5 overexpression was induced, and the cells were further infected with an R5-tropic HIV-1 isolate the following day (FIG. 3A). At this early time point, cells infected with rSeV-Cas9-CCR5 were expected to have lower levels of CCR5 relative to cells infected with rSeV-Cas9-control due to ongoing mutagenesis of the inducible ccr5 transgene and endogenous ccr5 alleles. After an additional 2 days, flow cytometry revealed efficient knockout of the induced CCR5, and p24 staining indicative of HIV-1 infection at the earlier time point had a 43% reduction in geometric mean fluorescence intensity compared to the rSeV-Cas9-control infection (FIG. 3A).

Figure 3B:
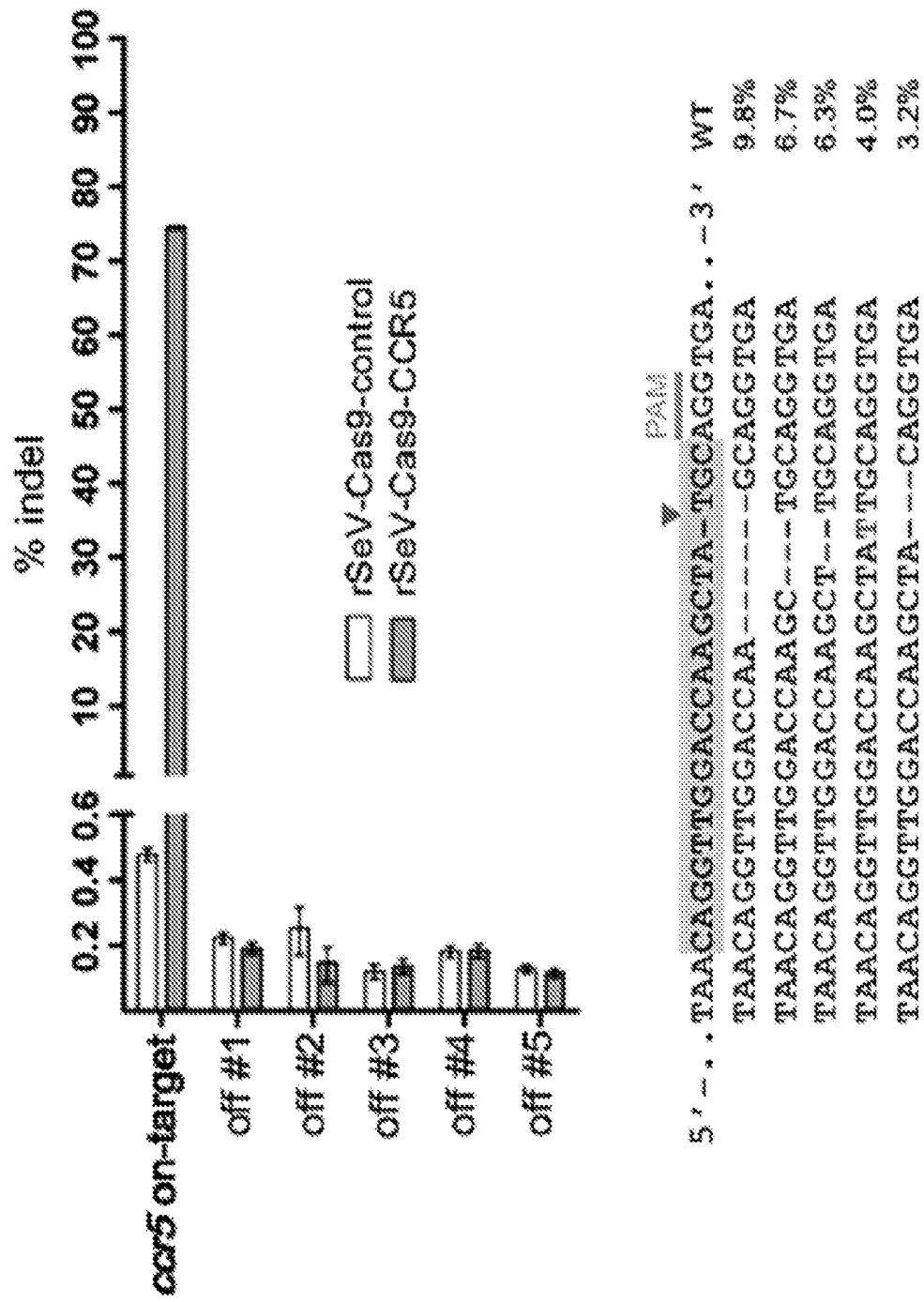
FIG. 3B: HEK293 cells were infected with rSeV-Cas9-control or the targeting viruses rSeV-Cas9-CCR5 or rSeV-Cas9-EFNB2 at MOI 25. Flow cytometry at 2 days post-infection indicated 98% infection. Cells were collected at 6 days post-infection for deep sequencing of target and off-target loci (see Table 2 infra for genomic locations and sequences). Error bars represent Jeffreys 95% confidence intervals. For each target, the 5 most abundant species of mutated target (SEQ ID NOs: 50-61, respectively) and their relative abundance percentages are shown.
Figure 3B:
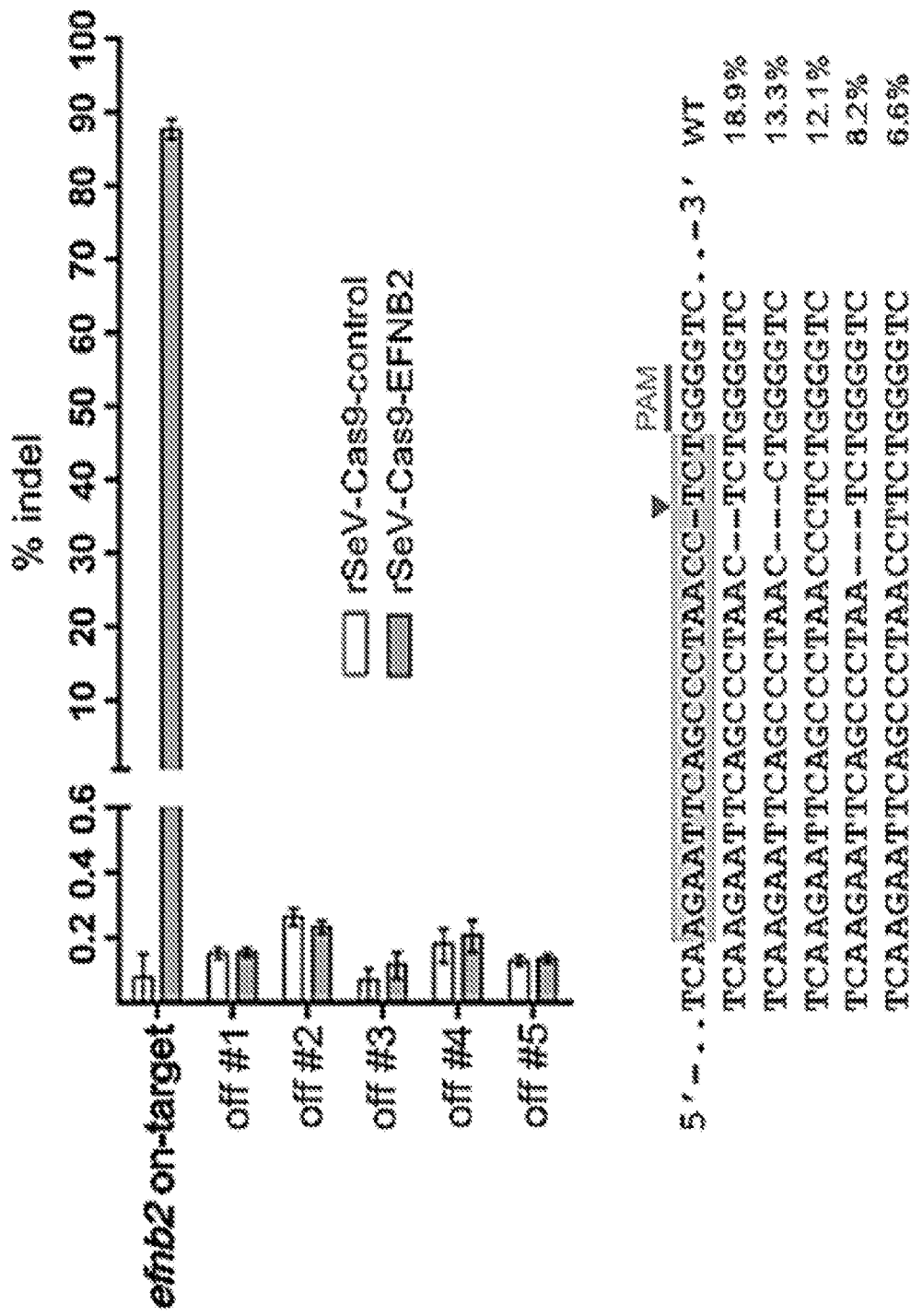

To examine mutagenesis of endogenous alleles, HEK293 cells were infected with the ccr5- and efnb2-targeting rSeV-Cas9 viruses at a MOI of 25 and were collected at 6 days post-infection. The on-target loci as well as the top five predicted off-target sites were PCR amplified. HEK293 cells are known to generally have 3 copies of chromosome 3 (encoding ccr5) and 2-3 copies of chromosome 13 (encoding efnb2). Deep sequencing revealed high rates of on-target mutagenesis (75% and 88% for ccr5 and efnb2, respectively) (FIG. 3B), once again strongly suggesting that rSeV-Cas9 is effective. Off-target mutagenesis was unremarkable for this first-generation Cas9 without modifications to increase specificity, ranging from no detectable increase to 0.05% above the non-targeting control (FIG. 3B). These results confirmed that Sendai virus delivery of CRISPR/Cas9 can efficiently target endogenous genes.

Ccr5-Targeting rSeV-Cas9 Edits Primary Human Monocytes at High Frequency

Figure 4:
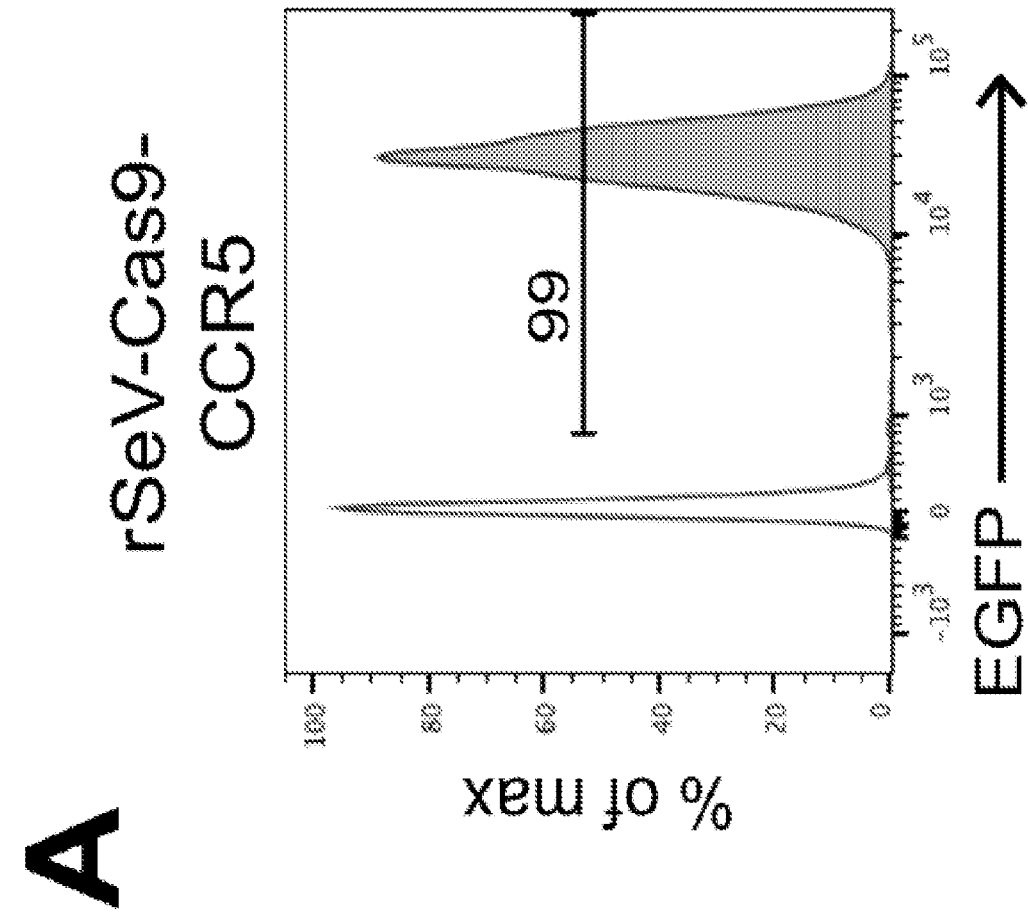
FIG. 4 represents Ccr5-targeting rSeV-Cas9 edits primary human monocytes at high frequency.
Figure 4A:
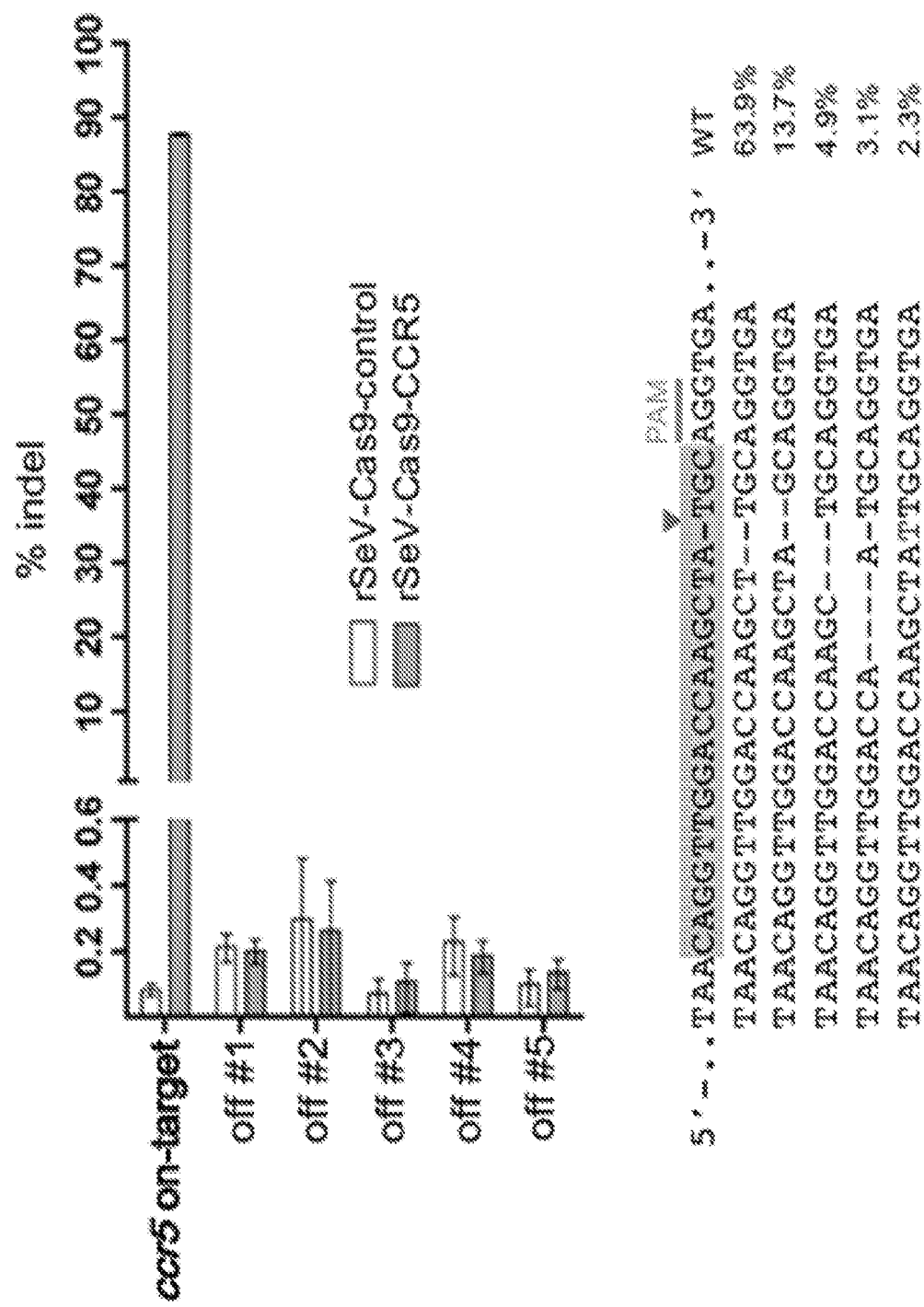
FIG. 4A: Primary human monocytes were infected with rSeV-Cas9-control or rSeV-Cas9-CCR5 at MOI 50 with simultaneous stimulation with GM-CSF and collected at 5 days post-infection for deep sequencing of on-target and off-target loci. Flow cytometry showed 98% infection. Error bars represent Jeffreys 95% confidence intervals. For each target, the 5 most abundant species of mutated target (SEQ ID NOs: 62-67, respectively) and their relative abundance percentages are shown.
Figure 4:
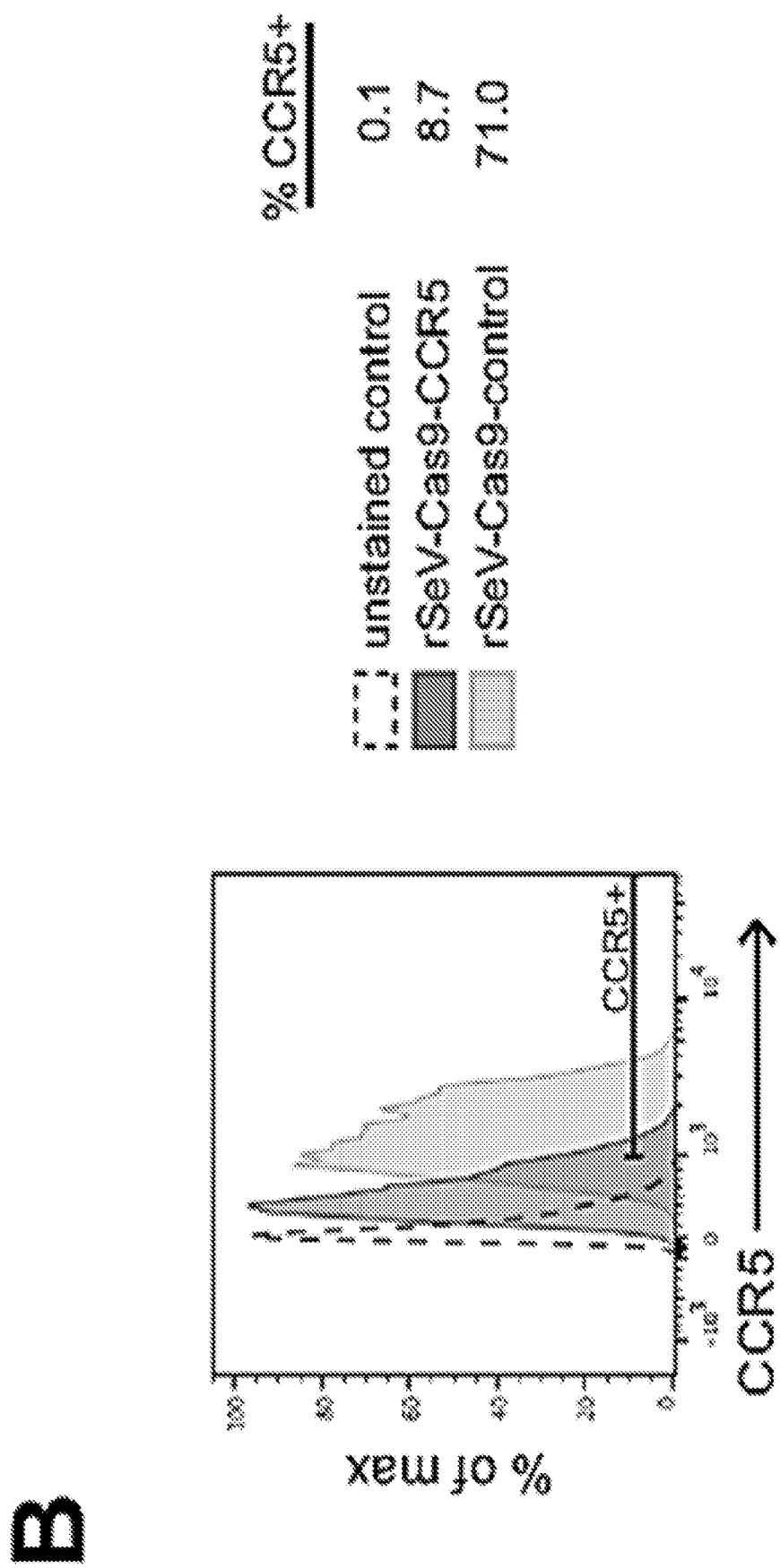
Figure 6:
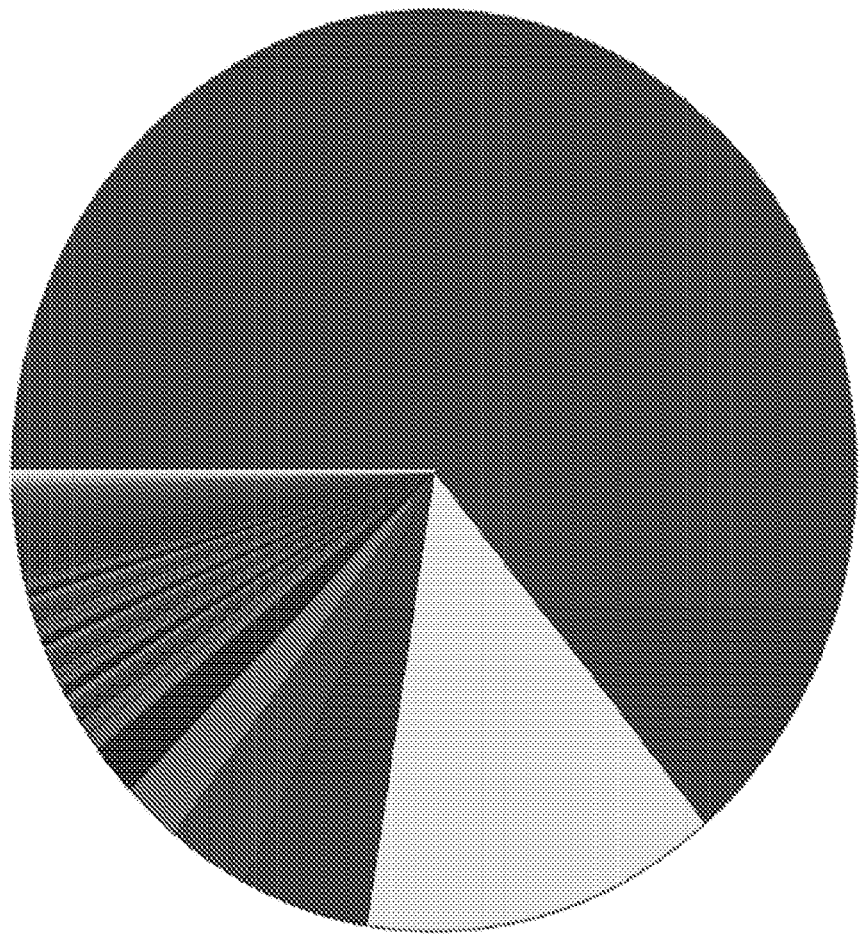
FIG. 6 represents abundance of ccr5 mutation variants in monocytes (FIG. 6A) and HEK293s (FIG. 6B). The relative abundance of all mutation variants for ccr5 are shown in the pie charts. These specific variants are also highlighted in the HEK293 pie chart. The distributions of variant abundance for the 100 most abundant variants for either monocytes or HEK293s are shown at right.
Figure 6A:
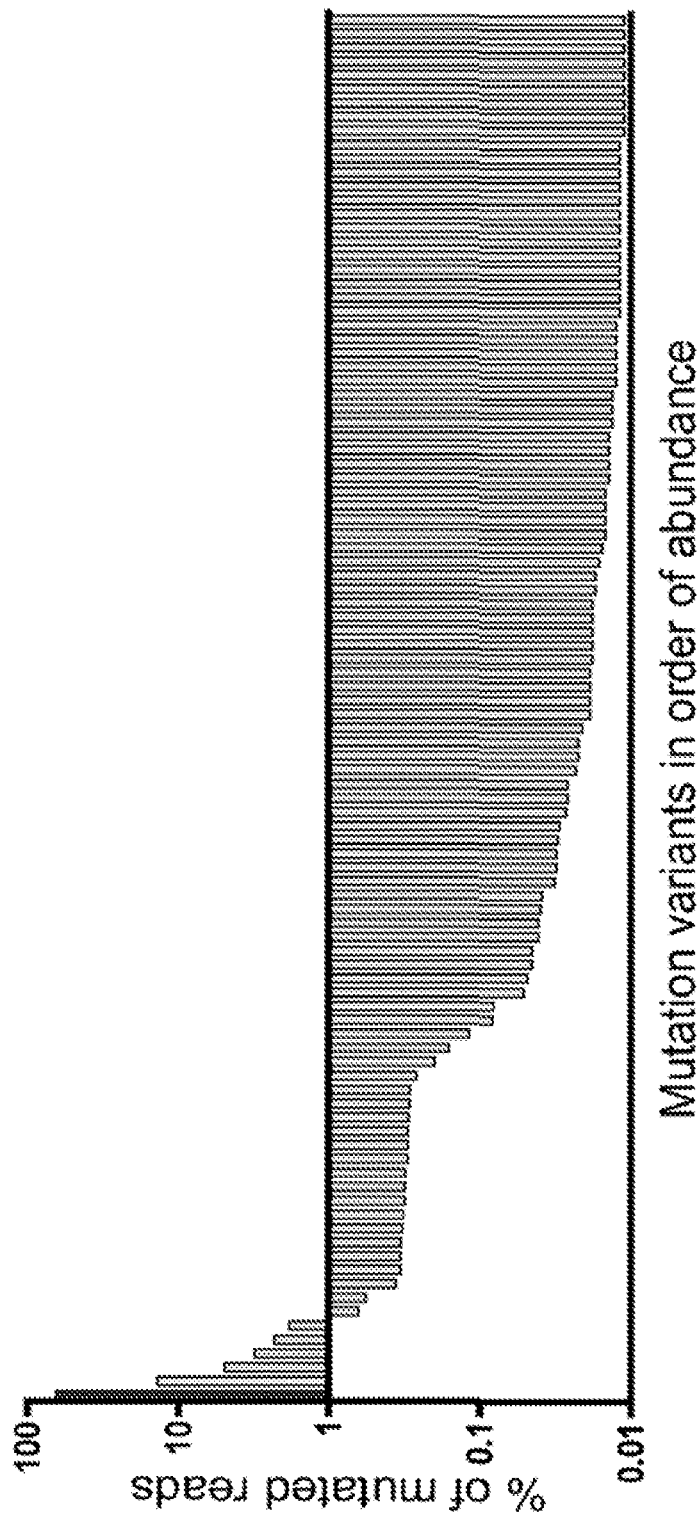
Figure 6:
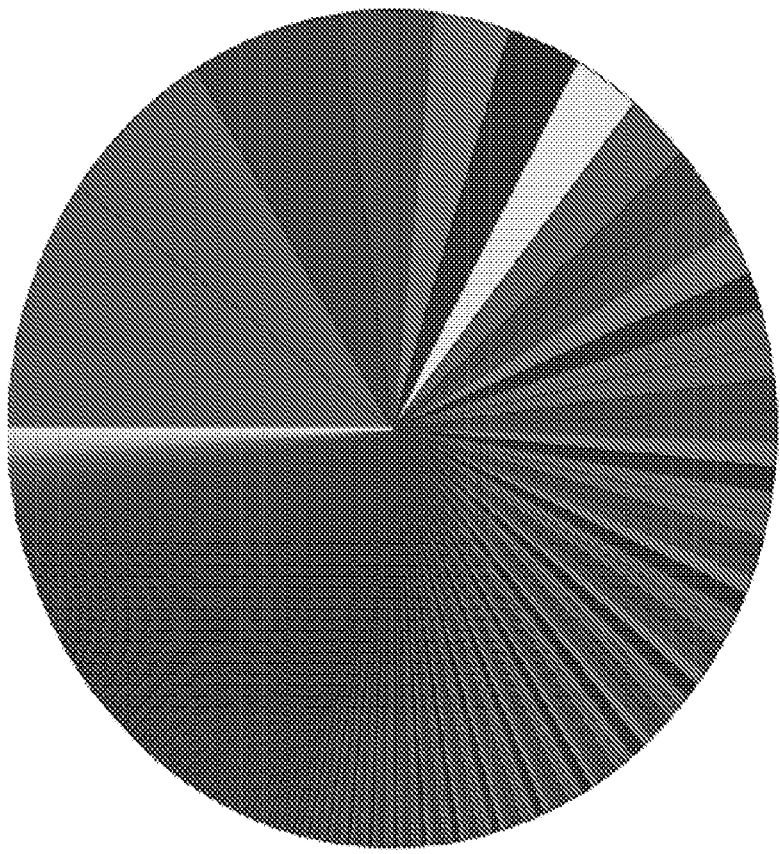
Figure 6B:
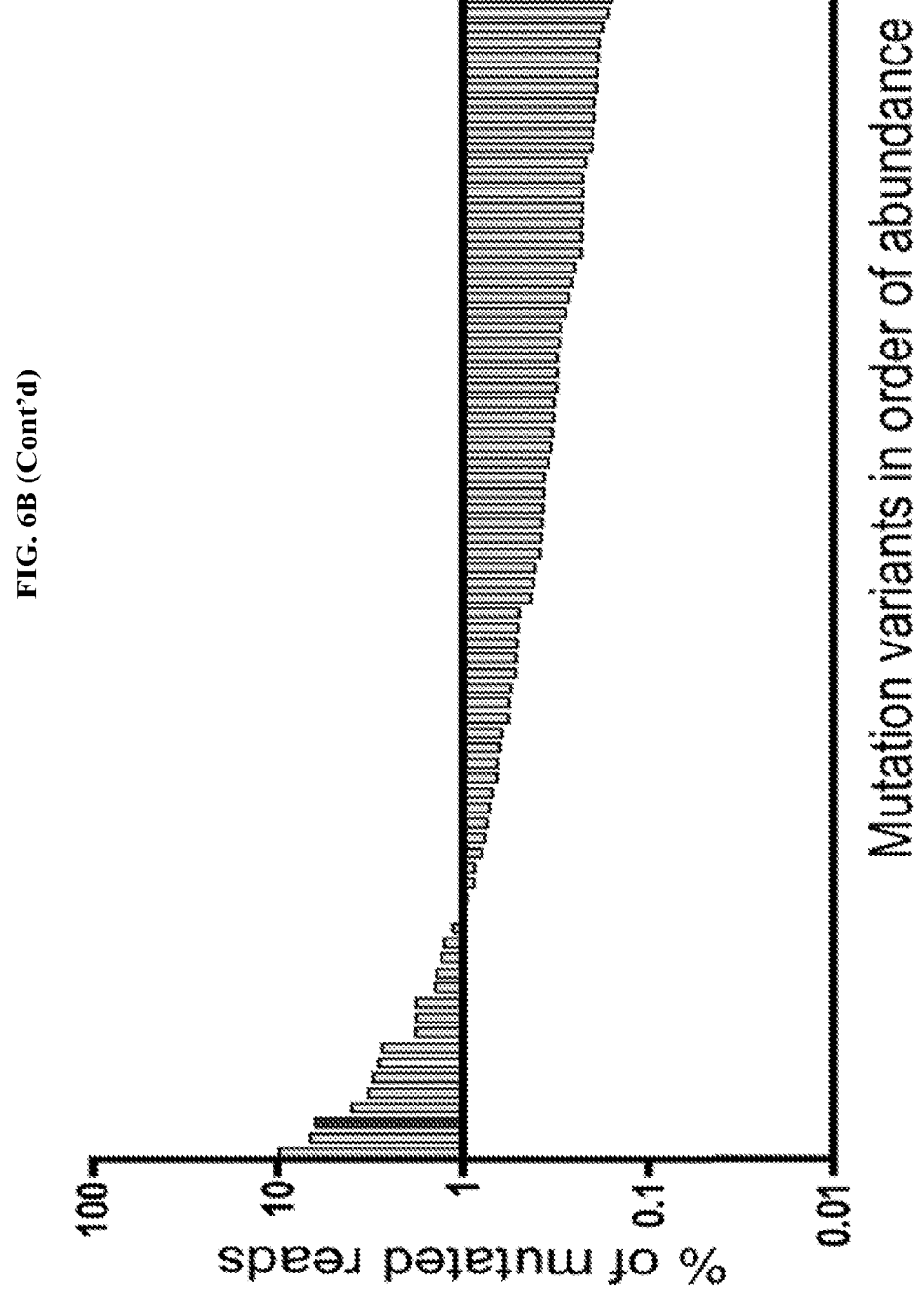

Primary human CD14+ monocytes were infected with rSev-Cas9, which are normally resistant to lentiviral transduction, at a MOI of 50. To better visualize reduction in CCR5 expression upon mutagenesis, monocytes were also stimulated with GM-CSF to induce macrophage differentiation with concomitant upregulation of CCR5. Cells were collected at 5 days post-infection, and deep sequencing revealed 88% on-target mutagenesis (FIG. 4A). Surprisingly, the two single nucleotide deletions flanking the cleavage site together comprised 78% of all detected indels (FIG. 4A and FIG. 6); by contrast, in HEK293 cells the same deletions together comprised 9% of detected indels, and no single mutation comprised more than 10% of the total (FIG. 3B and FIG. 6). Infection of monocytes from an independent donor showed a similar result, with the above deletions comprising ~50% of mutant alleles (19/38 mutations via Sanger sequencing), indicating that this may represent a cell type-specific phenomenon. When single specific mutations comprise such a large proportion of the total indels, mismatch-based assays such as the T7E1 endonuclease assay, which relies on highly variable mutagenesis to detect mutations, may strongly underestimate the degree of on-target mutagenesis. As with the HEK293 cells, detected mutagenesis of predicted off-target loci in the monocytes was negligible (FIG. 4A). Flow cytometry of infected monocytes from an independent donor confirmed knockout of cell surface CCR5 at the same time point (FIG. 4B).

Example 2

Temperature Sensitive Mutants of rSeV-Cas9 Vector

Figure 8:
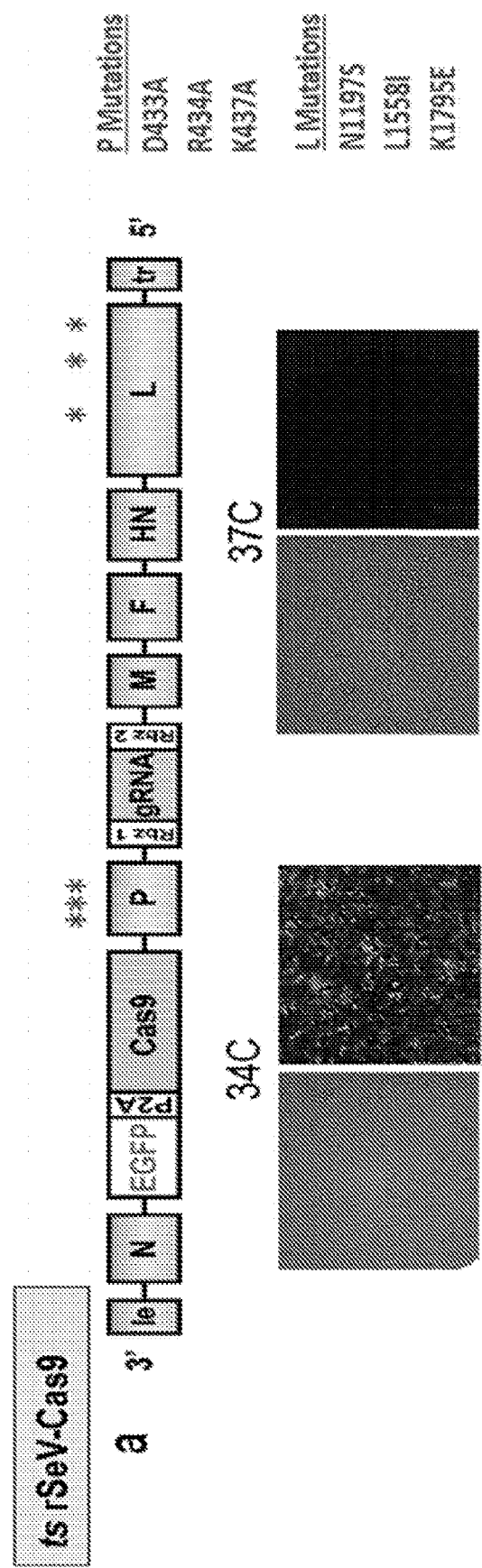
FIG. 8 represents a schematic of the PL mutant generated in Example 2.
Figure 8:
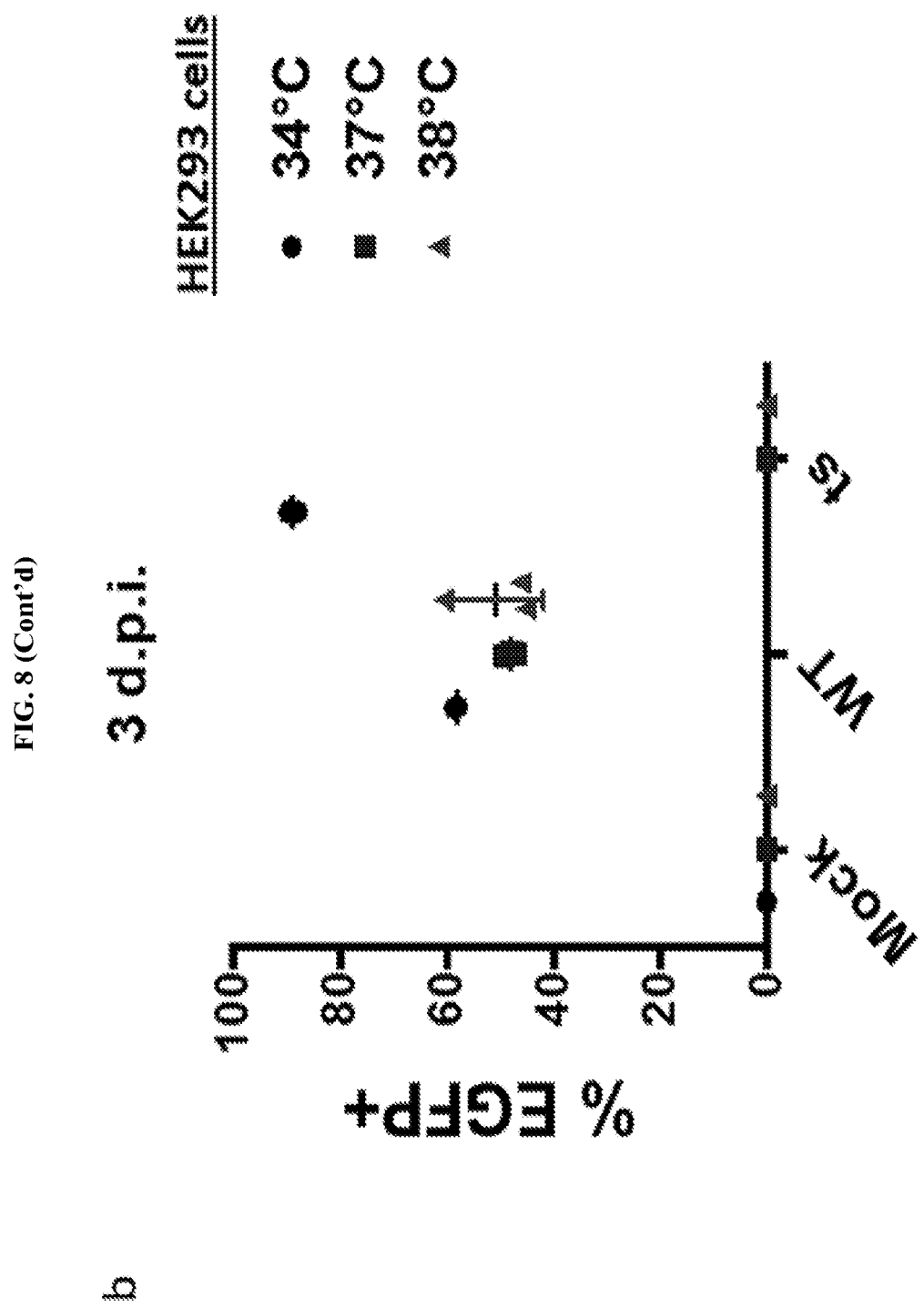
Figure 9:
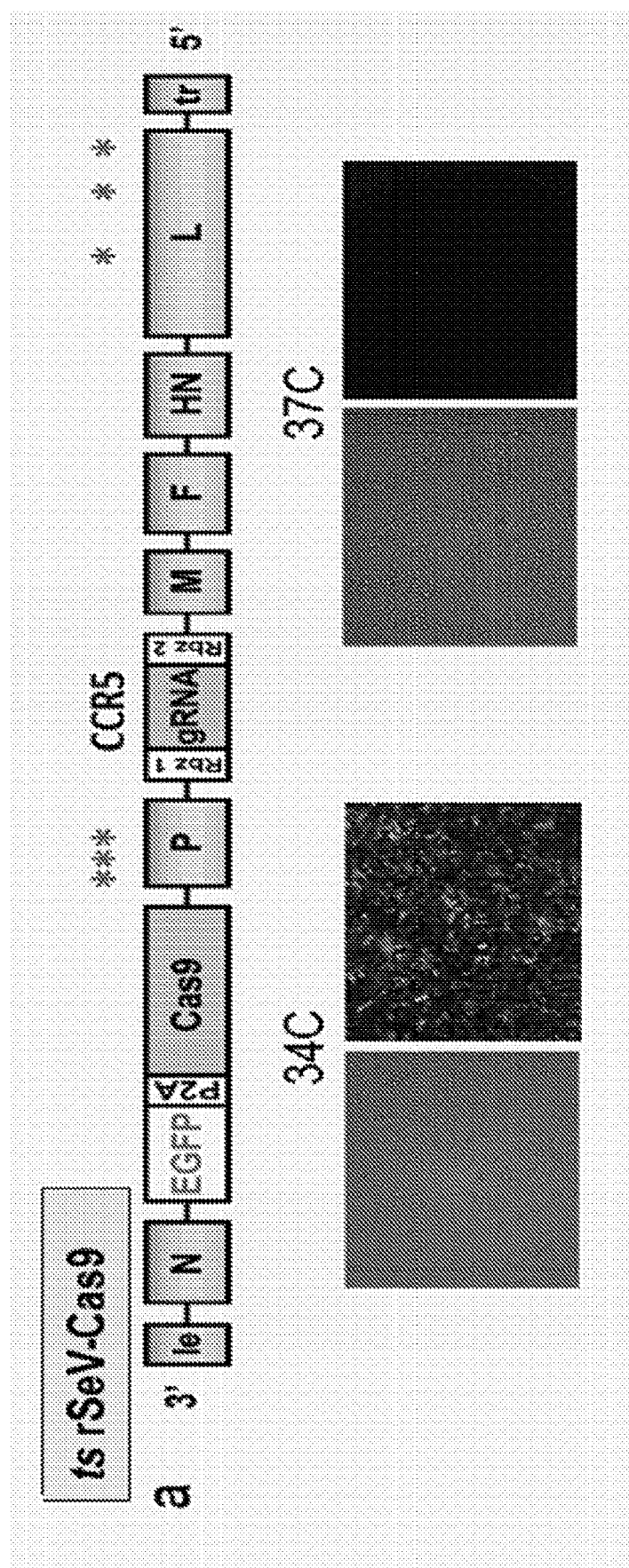
FIG. 9 represents the PL mutant's (ts rSeV-Cas9-CCR5 vector) ability to infect human CD34+ hematopoietic stem cells (HSCs) from both human fetal liver and peripheral blood.
Figure 9:
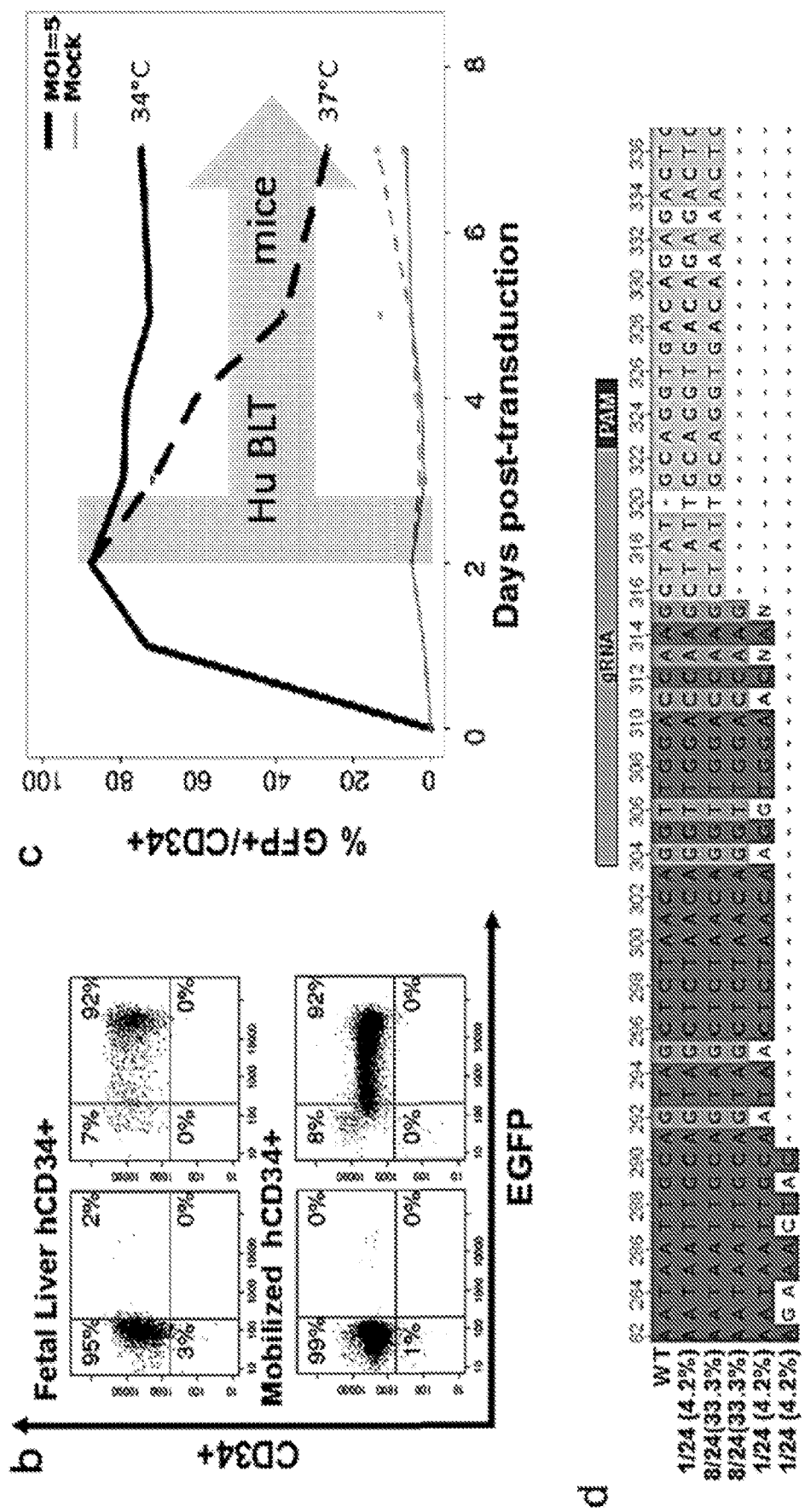

A temperature sensitive (ts) mutant of the rSev-Cas9 vector described in Example 1 above was created. This mutant was made by introducing several mutations into the P (D433A, R434A, K437A) and L (L15581, N1197S, K1795E) genes of the recombinant Sendai virus vector, referred to herein as the "PL mutant." The PL mutant efficiently edits at permissive temperatures, for example, temperatures up to and around 34° C., but is eliminated upon shifting to non-permissive temperatures, for example, temperatures above 37° C. and above. PL mutants of the Sendai virus have been previously reported in literature, but not for purposes of CRISPR-Cas gene editing. Generation of PL mutants can be found at, for example, Ban H. et al. PNAS 2011 Aug. 23; 108(34): 14234-14239, hereby incorporated by reference in its entirety. The PL mutant generated in Ban H. et al. was a Z strain of Sendai virus, whereas the present rSev-Cas9 vector used was a Fushimi F1R strain. A schematic of the ts mutations adapted from Ban H. et al. in the rSev-Cas9 vector (PL mutant) is illustrated in FIGS. 8A and 9A. The temperature sensitive phenotype of the PL mutant is shown in FIG. 8B.

The PL mutant has been shown to be capable of infecting human CD34+ hematopoietic stem cells (HSCs) from both human fetal liver and peripheral blood mobilized CD34+ HSCs at 80-90% efficiency. Furthermore, editing frequency in these HSCs at about 80%. For example, as shown in FIG. 9B, the PL mutants (ts rSeV-Cas9-CCR5 vectors) successfully infected and transduced purified human fetal liver CD34+ and peripheral blood mobilized CD34+ HSCs. Time course of infection is shown in FIG. 9C. Sanger sequencing data, from ts rSeV-Cas9-CCR5 infected CD34+ HSCs at 2 dpi. 19/24 clones (~80%), shown in FIG. 9D, showed indels at the targeted CCR5 locus.

Figure 10:
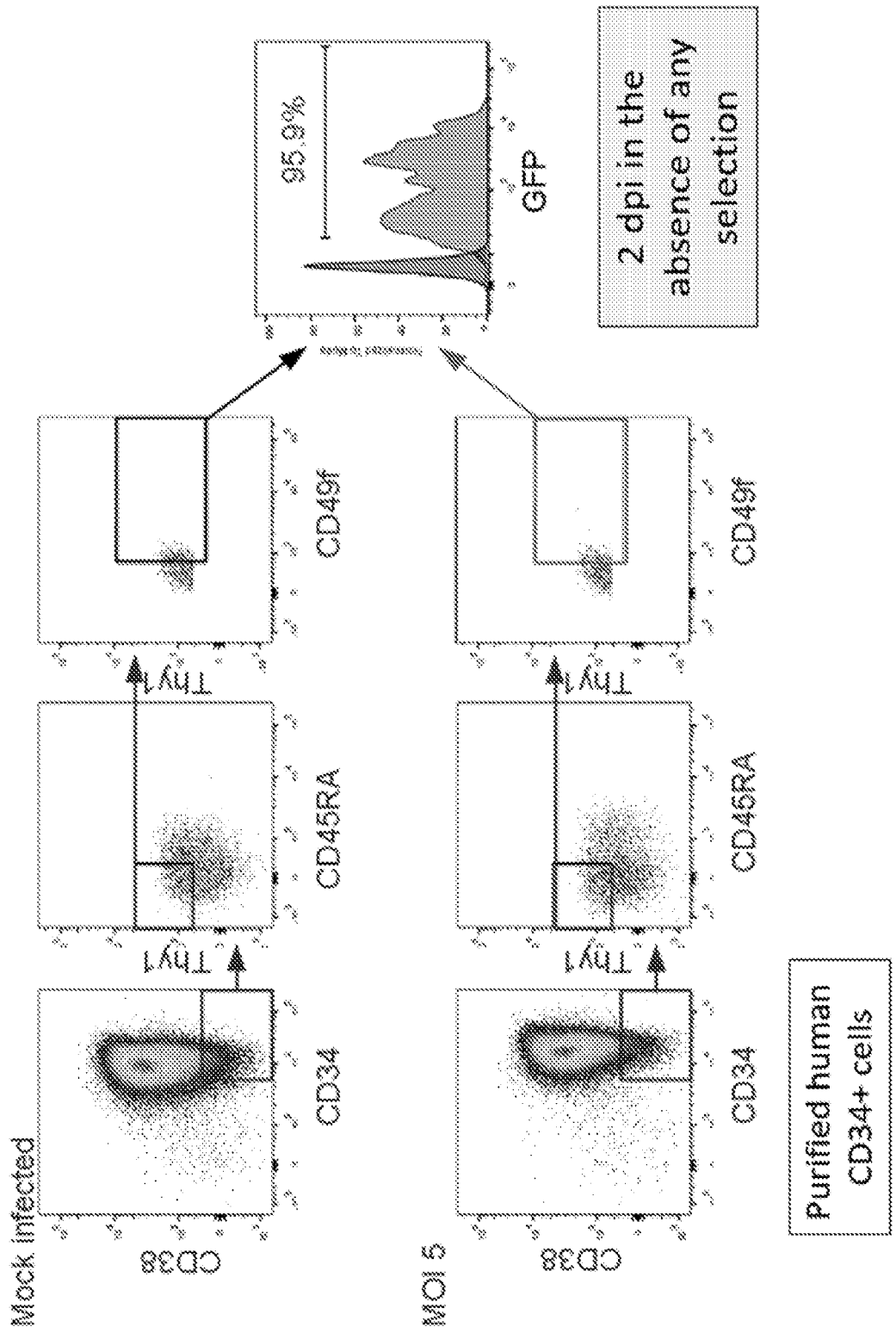
FIG. 10 represents the PL mutant (ts rSeV-Cas9-CCR5 vector) efficiently transduces human CD34+/CD38−/CD45RA−/CD90+ (Thy1+)/CD49f high cells (LT-HSC, SCID-Repopulating Cells). Phenotyping of infected CD34+ HSCs showed that the PL mutants can infect >90% of CD34+/CD38−/CD45RA−/CD90+(Thy1+)/CD49f-high cells which are known in the literature as long-term-HSC or SCID-repopulating cells, capable of reconstituting SCID (immunodeficient) mice at a single cell level (i.e. "true" stem cells.)

Infected CD34+ HSCs have been transplanted into immunodeficient SCID-Hu mice (n=9 for each group). All except one mice remained healthy at 10 weeks post-transplant. This illustrated that the PL mutants did not revert in vivo to a pathogenic virus, as wild type Sendai virus is highly pathogenic even in wild-type immunocompetent mice, and likely would have killed the immunodeficient SCID-Hu mice. Phenotyping of infected CD34+ HSCs (FIG. 10) illustrated that the PL mutants can infect >90% of CD34+/CD38−/CD45RA−/CD90+(Thy1+)/CD49f-high cells which are known as long-term-HSC or SCID-re-populating cells, capable of reconstituting SCID-Hu mice at a single cell level.

Figure 11:
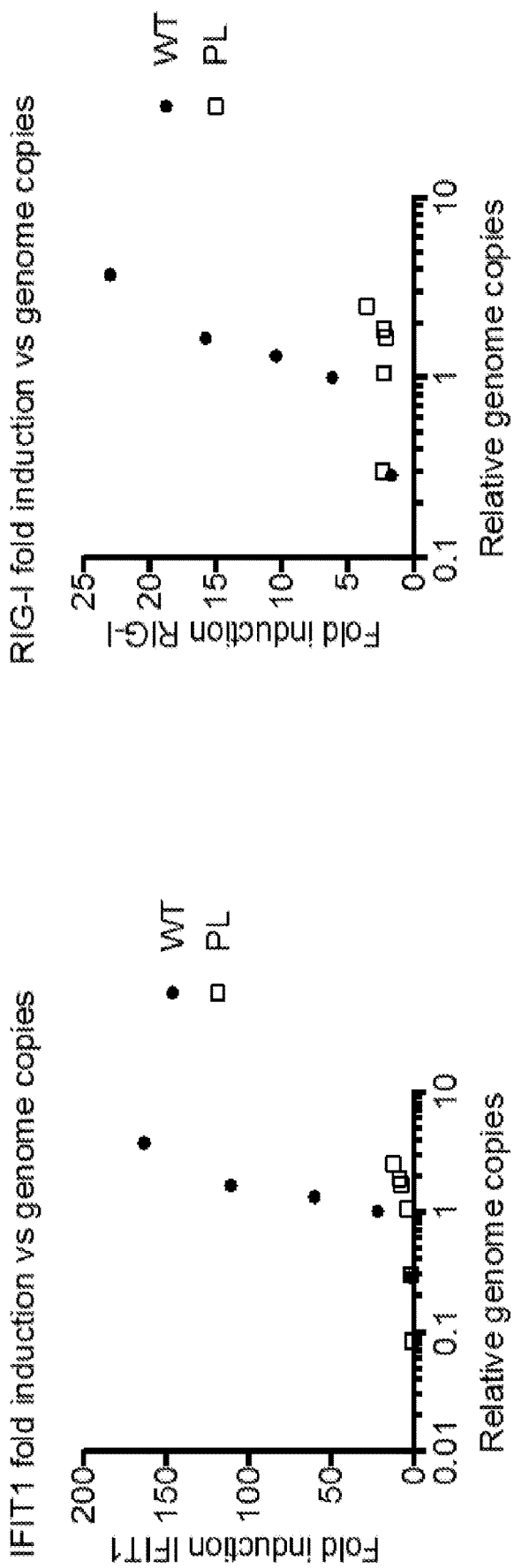
FIG. 11 represents the fold induction of 2 representative ISGs (interferon stimulated genes) in 293T cells infected with either the "wild type" rSeV-Cas9 vector or the PL mutants across a wide range of viral inoculum. IFIT1 fold induction is represented in FIG. 11A. RIG-1 fold induction is represented in FIG. 11B. Viral replication and ISG induction was measured by qRT-PCR. Eveb at high viral genome copies, the PL mutant virus was markedly deficient in inducing ISGs. This remained true regardless of the gRNA contained (mCherry or CCR5). Data is shown for the CCR5 gRNA virus.

Additionally, the PL mutants generated were essentially silent in inducing the IFN response compared to the non PL-mutants (i.e. non-temperature sensitive rSeV-Cas9 vectors). This is a highly surprising but important phenotype. Furthermore, the PL mutants generated in Ban H. et al. did not mention the effect (positive or negative) of the PL mutants on the interferon response. There is additionally no present indication why the PL mutant generated in this Example possesses an "IFN-silent" phenotype, as Sendai virus infection is known to induce the production of IFN. FIGS. 11A and 11B show the fold induction of 2 representative interferon stimulated genes (ISGs) in 293T cells infected with either the rSeV-Cas9 vector of Example 1 or the temperature sensitive PL mutant vector across a wide range of viral inoculum, as measured by qRT-PCR. At high viral genome copies, the PL mutant vector is markedly deficient in inducing ISGs compared to the rSeV-Cas9 vector of Example 1. This remained true regardless of the gRNA contained, either mCherry or CCR5.

Example 3

Additional Modifications to the rSeV-Cas9 Vectors

Figure 12:
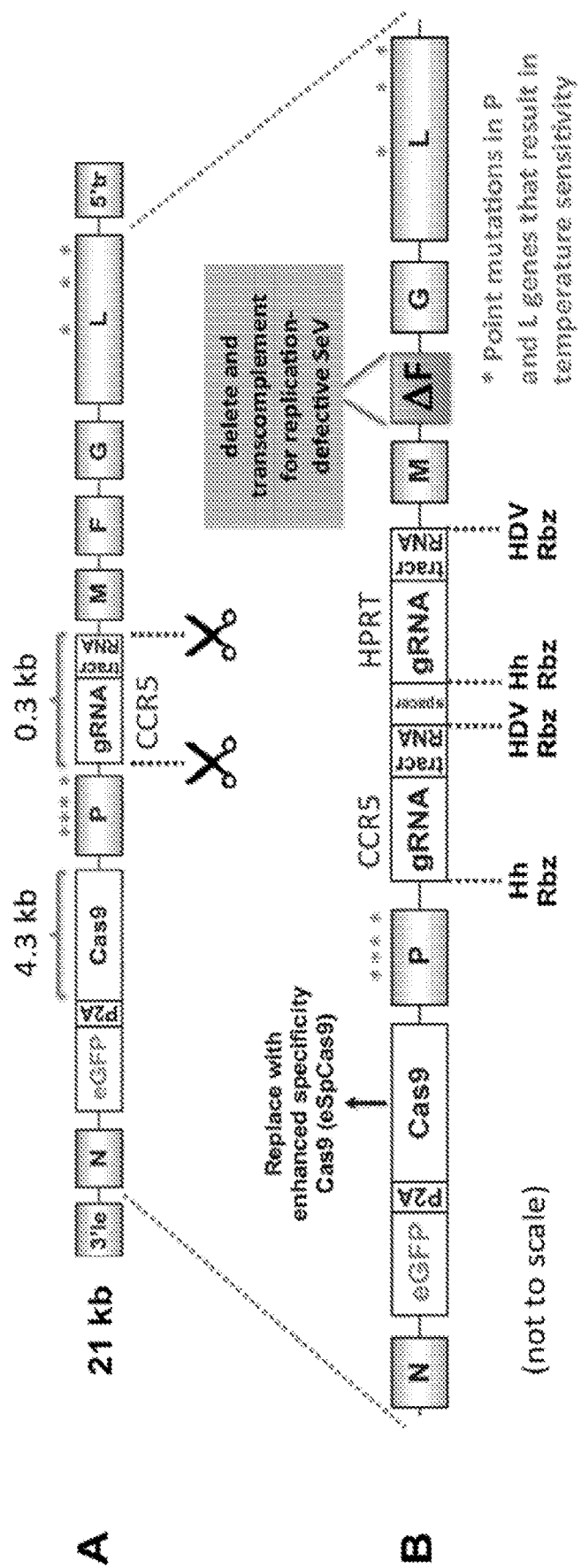
FIG. 12 represents a schematic diagram of an rSeV vector that can deliver two gRNAs, e.g. CCR5 gRNA and HRPT gRNA.

An additional deletion mutant of the rSeV-Cas9 vector described in Example 1 was created, missing the Fusion protein (i.e. ΔF mutants). These are only capable of growing in an F-complementing cell line. The temperature sensitive PL mutants of Example 2 are generated to be ΔF mutants. rSev-Cas9 vectors that can deliver two gRNAs are generated and illustrated in FIG. 12.

The foregoing examples and description of the preferred embodiments should be taken as illustrating, rather than as limiting the present disclosure as defined by the claims. As will be readily appreciated, numerous variations and combinations of the features set forth above can be utilized without departing from the present disclosure as set forth in the claims. Such variations are not regarded as a departure from the scope of the disclosure, and all such variations are intended to be included within the scope of the following claims. All references cited herein are incorporated by reference in their entireties.

The invention claimed is:

1. A nucleic acid comprising a genome sequence of a single-stranded RNA (ssRNA) virus or antigenome sequence that is complementary to the genome sequence, the antigenome sequence comprising a first region comprising
   (i) a target segment,
   (ii) a first segment encoding a first self-cleaving ribozyme, and
   (iii) a second segment encoding a second self-cleaving ribozyme,
wherein the target segment is adjacent to the first segment and wherein the target segment is flanked by the first segment and the second segment.

2. The nucleic acid of claim 1, wherein the first self-cleaving ribozyme is a 3' self-cleaving ribozyme or a 5' self-cleaving ribozyme.

3. The nucleic acid of claim 1, wherein the antigenome sequence further comprises a second region comprising a third segment encoding a nuclease.

4. The nucleic acid of claim 3, wherein the second region further comprises a fourth segment encoding a reporter molecule.

5. The nucleic acid of claim 1, wherein the target segment comprises guide RNA (gRNA), wherein the gRNA has a scaffold sequence and a targeting sequence.

6. The nucleic acid of claim 3, wherein the nuclease comprises Cas9 or Cpf1.

7. The nucleic acid of claim 1, wherein the first self-cleaving ribozyme comprises a hammerhead ribozyme.

8. The nucleic acid of claim 2, wherein the first self-cleaving ribozyme comprises one of a hammerhead ribozyme and a hepatitis delta virus (HDV) ribozyme.

9. The nucleic acid of claim 1, further comprising a third region comprising a fifth segment, wherein the fifth segment comprises a mutant P gene.

10. The nucleic acid of claim 1, further comprising a fourth region comprising a fourth region comprising a sixth segment, wherein the sixth segment comprises a mutant L gene.

* * * * *